US007888479B2

(12) United States Patent
De Fougerolles et al.

(10) Patent No.: US 7,888,479 B2
(45) Date of Patent: *Feb. 15, 2011

(54) HUMANIZED ANTIBODIES AGAINST MONOCYTE CHEMOTACTRIC PROTEINS

(75) Inventors: Antonin R. De Fougerolles, Brookline, MA (US); Victor E. Kotelianski, Boston, MA (US); Ellen Garber, Cambridge, MA (US); Carl Reid, Mattapan, MA (US); Jose W. Saldanha, Middlesex (GB); Herman Van Vlijmen, Mechelen (BE)

(73) Assignee: Biogen Idec Ma Inc., Cambridge, MA (US)

( * ) Notice: Subject to any disclaimer, the term of this patent is extended or adjusted under 35 U.S.C. 154(b) by 1105 days.

This patent is subject to a terminal disclaimer.

(21) Appl. No.: 10/536,067

(22) PCT Filed: Nov. 25, 2003

(86) PCT No.: PCT/US03/37834

§ 371 (c)(1),
(2), (4) Date: Aug. 8, 2006

(87) PCT Pub. No.: WO2004/050836

PCT Pub. Date: Jun. 17, 2004

(65) Prior Publication Data
US 2007/0134236 A1 Jun. 14, 2007

Related U.S. Application Data

(60) Provisional application No. 60/430,007, filed on Nov. 27, 2002.

(51) Int. Cl.
*C12P 21/08* (2006.01)
*C07K 16/00* (2006.01)
*A61K 39/395* (2006.01)
*C12P 21/04* (2006.01)

(52) U.S. Cl. ............. 530/387.3; 424/133.1; 424/141.1; 424/145.1; 435/69.6; 435/70.21; 435/326; 530/388.1; 530/388.23

(58) Field of Classification Search ........................ None
See application file for complete search history.

(56) References Cited

U.S. PATENT DOCUMENTS

| 5,859,205 | A  | * | 1/1999 | Adair et al. |
| 6,084,075 | A  |   | 7/2000 | Lind et al. |
| 6,407,213 | B1 |   | 6/2002 | Carter et al. |
| 7,405,277 | B2 | * | 7/2008 | De Fougerolles et al. |
| 2005/0025768 | A1 |   | 2/2005 | De Fougerolles et al. |
| 2009/0017028 | A1 | * | 1/2009 | De Fougerolles et al. |

FOREIGN PATENT DOCUMENTS

| JP | 09067399 A | 3/1997 |
| WO | WO-97/31949 | 9/1997 |
| WO | WO-00/05265 | 2/2000 |
| WO | WO-01/57226 A1 | 8/2001 |
| WO | WO-03/048083 A2 | 6/2003 |

OTHER PUBLICATIONS

Foote et al. Journal of Molecular Biology, 224(2):487-499, 1992.*
Fundamental Immunology, William E. Paul, M.D. ed., 3rd ed., p. 242 and 292-295, 1993.*
Rudikoff et al. Proc. Natl. Acad. Sci. USA, 79(6):1979-1983, Mar. 1982.*
Colman P. M. Research in Immunology, 145:33-36, 1994.*
Bendig M. M. Methods: A Companion to Methods in Enzymology, 1995; 8:83-93.*
MacCallum et al. J. Mol. Biol., 262, 732-745, 1996.*
Casset et al. Biochemical and Biophysical Research Communications, 307:198-205, 2003.*
Boring, et al. "Decreased Lesion formation in CCR2-/-Mice Reveals a Role for Chemokines in the Initiation of Atherosclerosis." *Nature* 394(6696): 894-897 (1998).
Campbell, et al. "Monocyte Chemoattractant Protein 1 Mediates Cockroach Allergen-Induced Bronchial Hyperreactivity in Normal but not CCR2-/-Mice: the Role of Mast Cells." *The Journal of Immunology*, 163(4): 2160-2167 (1999).
European Supplemental Search Report of Application No. EP 03 79 0088, mailed on May 3, 2006.
Huang, et al. "Absence of Monocyte Chemoattractant Protein 1 in Mice leads to decreased local Macrophage Recruitment and Antigen-specific T Helper Cell Type 1 Immune response in experimental Autoimmune Encephalomyelitis" *Journal of Experimental Medicine*, 193(6): 713-725 (2001).
International Search Report of International Application No. PCT/US02/38229, mailed on Jul. 11, 2003.
International Search Report of International Application No. PCT/US03/37834, mailed on Jul. 23, 2004.
Luo, et al. "Serologic Analysis of the Mouse Beta Chemokine JE/Monocyte Chemoattractant Protein-1" *Journal of Immunology*, 153(8): 3708-3716 (1994).
Proost, et al. "Human Monocyte Chemotactic Proteins 2 and 3: Structural and Functional Comparison with MCP-1." *Journal of Leukocyte Biology*, 59(1): 67-74 (1996).
Salcedo, et al. "Human Endothelial Cells Express CCR2 and respond to MCP-1: Direct Role of MCP-1 in Angiogenesis and Tumor Progression." *Blood*, 96(1): 34-40 (2000).
Van Collie, et al. "The MCP/eotaxin Subfamily of CC Chemokines" *Cytokine & Growth Factor Reviews*, 10: 61-86 (1999).

(Continued)

*Primary Examiner*—David J. Blanchard
(74) *Attorney, Agent, or Firm*—Finnegan, Henderson, Farabow, Garrett & Dunner, L.L.P.

(57) ABSTRACT

The invention provides humanized antibodies that bind to a plurality of b-chemokines, particularly monocyte chemotactic proteins MCP-1, MCP-2 and MCP-3. The invention also provides therapeutic reagents and methods of treating disorders associated with detrimental MCP activity.

46 Claims, 30 Drawing Sheets

OTHER PUBLICATIONS

Weber, et al. "Expression of CCR2 by Endothelial Cells: Implications for MCP-1 Mediated Wound Injury Repair and In Vivo Inflammatory Activation of Endothelium." *Arteriosclerosis Thrombosis and Vascular Biology*, 19: 2085-2093 (1999).

Anonymous: "Antibodies to Cytokines & Cytokine Receptors," Downloaded from the Internet Mar. 12, 2007, according to the European Patent Office.

Dean, "Preparation and Characterization of Monoclonal Antibodies to Proteins and Other Cellular Components," *Methods in Molecular Biology, vol. 32: Basic Protein and Peptide Protocols* (1994).

Lummus et al., "Diisocyanate Antigen-enhanced Production of Monocyte Chemoattractant Protein-1, IL-8, and Tumor Necrosis Factor-a by Peripheral Mononuclear Cells of Workers with Occupational Asthma," *Journal of Allergy and Clinic Immunology*, vol. 102(2):265-274, Aug. 1998.

Sawyer et al., "Methodology for Selection of Human Antibodies to Membrane Proteins from a Phage-Display Library," *Journal of Immunological Methods* 204:193-203 (1997).

Anonymous: "*Anti-human CCL7/MCP-3 Antibody*," R&D Systems, Inc., dated Jul. 15, 2005.

Ward et al. (1989) *Nature* 341:544-46.

van den Beucken et al. (2001) *J. Mol. Bio*. 310:591-601.

Muyldermans et al. (2001) *Trends Biochem. Sci*. 26:230-35.

\* cited by examiner

1A1 Heavy Chain Variable Region

```
  1 GAGGTCCAGCTGCAGCAGTCTGGGGCAGAACTTGTGAGGTCAGGGGCCTCAGTCAAGTTG  60
    E   V   Q   L   Q   Q   S   G   A   E   L   V   R   S   G   A   S   V   K   L

CDR1
 61 TCCTGCACAGCTTCTGGCTTCAACATTAAAGACAACTATATGCACTGGGTGAAGCAGAGG 120
    S   C   T   A   S   G   F   N   I   K   D   N   Y   M   H   W   V   K   Q   R

CDR2
121 CCTGAACAGGGCCTGGAGTGGATTGGATGGATTGATCCTGAGAATGGAGATACTGAATAT 180
    P   E   Q   G   L   E   W   I   G   W   I   D   P   E   N   G   D   T   E   Y

181 GCCCCGAAGTTCCAGGGCAAGGCCACTATGACTGCAGACACATCCTCCAACACAGCCTAC 240
    A   P   K   F   Q   G   K   A   T   M   T   A   D   T   S   S   N   T   A   Y

CDR3
241 CTGCAGCTCAGCAGCCTGACATCTGAGGACACTGCCGTCTATTACTGTAATACATGGGCT 300
    L   Q   L   S   S   L   T   S   E   D   T   A   V   Y   Y   C   N   T   W   A

301 TACTACGGTACTAGCTACGGGGGATTTGCTTACTGGGGCCAAGGGACCACGGTCACCGTC 360
    Y   Y   G   T   S   Y   G   G   F   A   Y   W   G   Q   G   T   T   V   T   V

361 TCCTCA 366      (SEQ ID NO: 9)
    S   S          (SEQ ID NO: 11)
```

*Fig. 7A*

1A1 Light Chain Variable Region

```
  1 GATATCCAGATGACTCAGACTCCACTCACTTTGTCGGTTACCATTGGACAACCAGCCTCC  60
    D  I  Q  M  T  Q  T  P  L  T  L  S  V  T  I  G  Q  P  A  S
```

```
                CDR1
 61 ATCTCTTGCAAGTCAAGTCAGAGCCTCTTAGATAGTGATGGAAAGACATATTTGAATTGG 120
    I  S  C  K  S  S  Q  S  L  L  D  S  D  G  K  T  Y  L  N  W
```

```
                                              CDR2
121 TCGTTACAGAGGCCAGGCCAGTCTCCAAAGCGCCTAATCTATCTGGTGTCTAAACTGGAC 180
    S  L  Q  R  P  G  Q  S  P  K  R  L  I  Y  L  V  S  K  L  D
```

```
181 TCTGGAGTCCCTGACAGGTTCACTGGCAGTGGATCAGGGACAGATTTCACACTGAAAATC 240
    S  G  V  P  D  R  F  T  G  S  G  S  G  T  D  F  T  L  K  I
```

```
                                        CDR3
241 AGCAGAGTGGAGGCTGAGGATTTGGGAGTTTATTATTGCTGGCAAGGTACACATTTTCCT 300
    S  R  V  E  A  E  D  L  G  V  Y  Y  C  W  Q  G  T  H  F  P
```

```
301 CAGACGTTCGGTGGAGGCACCAAGCTGGAGATCAAA 336    (SEQ ID NO: 10)
    Q  T  F  G  G  G  T  K  L  E  I  K          (SEQ ID NO: 12)
```

*Fig. 7B*

11K2 Heavy Chain Variable Region

```
  1 GAGGTTCAGCTGCAGCAGTCTGGGGCAGAGCTTGTGAAGGCAGGGGCCTCAGTCAAGTTG  60
    E   V   Q   L   Q   Q   S   G   A   E   L   V   K   A   G   A   S   V   K   L

CDR1
 61 TCCTGCCCAGCTTCTGGCCTCAACATTAAAGACACCTATATGCACTGGGTGAAGCAGAGG 120
    S   C   P   A   S   G   L   N   I   K   D   T   Y   M   H   W   V   K   Q   R

CDR2
121 CCTGAACAGGGCCTGGAGTGGATTGGAAGGATTGATCCTGCGAATGGTAATACTAAATTT 180
    P   E   Q   G   L   E   W   I   G   R   I   D   P   A   N   G   N   T   K   F

181 GACCCGAAGTTCCAGGGCAAGGCCACTATAACAGCAGACACATCCTCCAACACAGCCTAC 240
    D   P   K   F   Q   G   K   A   T   I   T   A   D   T   S   S   N   T   A   Y

CDR3
241 CTGCAGCTCAGCAGCCTGACATCTGAGGACACTGCCGTCTATTACTGTGCTAGAGGCGTC 300
    L   Q   L   S   S   L   T   S   E   D   T   A   V   Y   Y   C   A   R   G   V

301 TTTGGCTTTTTTGACTACTGGGGCCAAGGCACCACTCTCACAGTCTCCTCA 351  (SEQ ID NO:25)
    F   G   F   F   D   Y   W   G   Q   G   T   T   L   T   V   S   S      (SEQ ID NO:27)
```

*Fig. 8A*

11K2 Light Chain Variable Region

```
  1 GACATTCAGATGACTCAGTCTTCATCCTCCTTTTCTGTATCTCTAGGAGACAGAGTCACC  60
    D  I  Q  M  T  Q  S  S  S  F  S  V  S  L  G  D  R  V  T
```

```
                  CDR1
 61 ATTACTTGCAAGGCAACTGAGGACATATATAATCGATTAGCCTGGTATCAGCAGAAACCA 120
    I  T  C  K  A  T  E  D  I  Y  N  R  L  A  W  Y  Q  Q  K  P
```

```
                              CDR2
121 GGAAGTGCTCCTAGGCTCTTAATTTCTGGTGCAACCAGTTTGGAGACTGGGGTTCCTTCA 180
    G  S  A  P  R  L  L  I  S  G  A  T  S  L  E  T  G  V  P  S
```

```
181 AGATTCAGTGGCAGTGGATCTGGAAAAGATTACACTCTCAGCATTACCAGTCTTCAGACT 240
    R  F  S  G  S  G  S  G  K  D  Y  T  L  S  I  T  S  L  Q  T
```

```
                              CDR3
241 GAGGATGTTGCTACTTATTACTGTCAACAGTTTTGGAGTGCTCCGTACACGTTCGGAGGG 300
    E  D  V  A  T  Y  Y  C  Q  Q  F  W  S  A  P  Y  T  F  G  G
```

```
301 GGGACCAAGCTGGAGATCAAA 321    (SEQ ID NO: 26)
    G  T  K  L  E  I  K            (SEQ ID NO: 28)
```

*Fig. 8B*

DNA Sequence of 11K2 Heavy Chain Chimera

```
  1 GAGGTTCAGCTGCAGCAGTCTGGGGCAGAGCTTGTGAAGGCAGGGGCCTCAGTCAAGTTG  60
    E   V   Q   L   Q   Q   S   G   A   E   L   V   K   A   G   A   S   V   K   L

CDR1
 61 TCCTGCCCAGCTTCTGGCCTCAACATTAAAGACACCTATATGCACTGGGTGAAGCAGAGG 120
    S   C   P   A   S   G   L   N   I   K   D   T   Y   M   H   W   V   K   Q   R

CDR2
121 CCTGAACAGGGCCTGGAGTGGATTGGAAGGATTGATCCTGCGAATGGTAATACTAAATTT 180
    P   E   Q   G   L   E   W   I   G   R   I   D   P   A   N   G   N   T   K   F

181 GACCCGAAGTTCCAGGGCAAGGCCACTATAACAGCAGACACATCCTCCAACACAGCCTAC 240
    D   P   K   F   Q   G   K   A   T   I   T   A   D   T   S   S   N   T   A   Y

CDR3
241 CTGCAGCTCAGCAGCCTGACATCTGAGGACACTGCCGTCTATTACTGTGCTAGAGGCGTC 300
    L   Q   L   S   S   L   T   S   E   D   T   A   V   Y   Y   C   A   R   G   V

301 TTTGGCTTTTTTGACTACTGGGGCCAAGGTACCACTCTCACAGTCTCCTCAGCCTCCACC 360
    F   G   F   F   D   Y   W   G   Q   G   T   T   L   T   V   S   S   A   S   T

361 AAGGGCCCATCGGTCTTCCCCCTGGCACCCTCCTCCAAGAGCACCTCTGGGGGCACAGCG 420
    K   G   P   S   V   F   P   L   A   P   S   S   K   S   T   S   G   G   T   A

421 GCCCTGGGCTGCCTGGTCAAGGACTACTTCCCCGAACCGGTGACGGTGTCGTGGAACTCA 480
    A   L   G   C   L   V   K   D   Y   F   P   E   P   V   T   V   S   W   N   S

481 GGCGCCCTGACCAGCGGCGTGCACACCTTCCCGGCTGTCCTACAGTCCTCAGGACTCTAC 540
    G   A   L   T   S   G   V   H   T   F   P   A   V   L   Q   S   S   G   L   Y

541 TCCCTCAGCAGCGTGGTGACCGTGCCCTCCAGCAGCTTGGGCACCCAGACCTACATCTGC 600
    S   L   S   S   V   V   T   V   P   S   S   S   L   G   T   Q   T   Y   I   C

601 AACGTGAATCACAAGCCCAGCAACACCAAGGTGGACAAGAAAGTTGAGCCCAAATCTTGT 660
    N   V   N   H   K   P   S   N   T   K   V   D   K   K   V   E   P   K   S   C

661 GACAAGACTCACACATGCCCACCGTGCCCAGCACCTGAACTCCTGGGGGGACCGTCAGTC 720
    D   K   T   H   T   C   P   P   C   P   A   P   E   L   L   G   G   P   S   V
```

*Fig. 9A*

```
721 TTCCTCTTCCCCCCAAAACCCAAGGACACCCTCATGATCTCCCGGACCCCTGAGGTCACA 780
     F  L  F  P  P  K  P  K  D  T  L  M  I  S  R  T  P  E  V  T

781 TGCGTGGTGGTGGACGTGAGCCACGAAGACCCTGAGGTCAAGTTCAACTGGTACGTGGAC 840
     C  V  V  V  D  V  S  H  E  D  P  E  V  K  F  N  W  Y  V  D

841 GGCGTGGAGGTGCATAATGCCAAGACAAAGCCGCGGGAGGAGCAGTACAACAGCACGTAC 900
     G  V  E  V  H  N  A  K  T  K  P  R  E  E  Q  Y  N  S  T  Y

901 CGTGTGGTCAGCGTCCTCACCGTCCTGCACCAGGACTGGCTGAATGGCAAGGAGTACAAG 960
     R  V  V  S  V  L  T  V  L  H  Q  D  W  L  N  G  K  E  Y  K

961 TGCAAGGTCTCCAACAAAGCCCTCCCAGCCCCCATCGAGAAAACCATCTCCAAAGCCAAA 1020
     C  K  V  S  N  K  A  L  P  A  P  I  E  K  T  I  S  K  A  K

1021 GGGCAGCCCCGAGAACCACAGGTGTACACCCTGCCCCCATCCCGGGATGAGCTGACCAAG 1080
      G  Q  P  R  E  P  Q  V  Y  T  L  P  P  S  R  D  E  L  T  K

1081 AACCAGGTCAGCCTGACCTGCCTGGTCAAAGGCTTCTATCCCAGCGACATCGCCGTGGAG 1140
      N  Q  V  S  L  T  C  L  V  K  G  F  Y  P  S  D  I  A  V  E

1141 TGGGAGAGCAATGGGCAGCCGGAGAACAACTACAAGACCACGCCTCCCGTGTTGGACTCC 1200
      W  E  S  N  G  Q  P  E  N  N  Y  K  T  T  P  P  V  L  D  S

1201 GACGGCTCCTTCTTCCTCTACAGCAAGCTCACCGTGGACAAGAGCAGGTGGCAGCAGGGG 1260
      D  G  S  F  F  L  Y  S  K  L  T  V  D  K  S  R  W  Q  Q  G

1261 AACGTCTTCTCATGCTCCGTGATGCATGAGGCTCTGCACAACCACTACACGCAGAAGAGC 1320
      N  V  F  S  C  S  V  M  H  E  A  L  H  N  H  Y  T  Q  K  S

1321 CTCTCCCTGTCTCCCGGGAAATGA  1344  (SEQ ID NO: 35)
      L  S  L  S  P  G  K  *        (SEQ ID NO: 37)
```

*Fig. 9A*
(Continued)

DNA Sequence of 11K2 Light Chain Chimera

```
  1 GACATTCAGATGACTCAGTCTTCATCCTCCTTTTCTGTATCTCTAGGAGACAGAGTCACC  60
    D  I  Q  M  T  Q  S  S  S  F  S  V  S  L  G  D  R  V  T

CDR1
 61 ATTACTTGCAAGGCAACTGAGGACATATATAATCGATTAGCCTGGTATCAGCAGAAACCA 120
    I  T  C  K  A  T  E  D  I  Y  N  R  L  A  W  Y  Q  Q  K  P

CDR2
121 GGAAGTGCTCCTAGGCTCTTAATTTCTGGTGCAACCAGTTTGGAGACTGGGGTTCCTTCA 180
    G  S  A  P  R  L  L  I  S  G  A  T  S  L  E  T  G  V  P  S

181 AGATTCAGTGGCAGTGGATCTGGAAAAGATTACACTCTCAGCATTACCAGTCTTCAGACT 240
    R  F  S  G  S  G  S  G  K  D  Y  T  L  S  I  T  S  L  Q  T

CDR3
241 GAGGATGTTGCTACTTATTACTGTCAACAGTTTTGGAGTGCTCCGTACACGTTCGGAGGG 300
    E  D  V  A  T  Y  Y  C  Q  Q  F  W  S  A  P  Y  T  F  G  G

301 GGGACCAAGCTGGAGATCAAACGAACTGTGGCTGCACCATCTGTCTTCATCTTCCCGCCA 360
    G  T  K  L  E  I  K  R  T  V  A  A  P  S  V  F  I  F  P  P

361 TCTGATGAGCAGTTGAAATCTGGAACTGCCTCTGTTGTGTGCCTGCTGAATAACTTCTAT 420
    S  D  E  Q  L  K  S  G  T  A  S  V  V  C  L  L  N  N  F  Y

421 CCCAGAGAGGCCAAAGTACAGTGGAAGGTGGATAACGCCCTCCAATCGGGTAACTCCCAG 480
    P  R  E  A  K  V  Q  W  K  V  D  N  A  L  Q  S  G  N  S  Q

481 GAGAGTGTCACAGAGCAGGACAGCAAGGACAGCACCTACAGCCTCAGCAGCACCCTGACG 540
    E  S  V  T  E  Q  D  S  K  D  S  T  Y  S  L  S  S  T  L  T

541 CTGAGCAAAGCAGACTACGAGAAACACAAAGTCTACGCCTGCGAAGTCACCCATCAGGGC 600
    L  S  K  A  D  Y  E  K  H  K  V  Y  A  C  E  V  T  H  Q  G

601 CTGAGCTCGCCCGTCACAAAGAGCTTCAACAGGGGAGAGTGTTAG 645   (SEQ ID NO: 36)
    L  S  S  P  V  T  K  S  F  N  R  G  E  C  *        (SEQ ID NO: 38)
```

Fig. 9B

Sequence of Hu-11K2 Heavy Chain, Version 1

```
  1 CAGGTTCAGCTGGTGCAGTCTGGGGCAGAGGTGAAGAAGCCCGGGTCCTCAGTCAAGGTC  60
    Q  V  Q  L  V  Q  S  G  A  E  V  K  K  P  G  S  S  V  K  V

CDR1
 61 TCCTGCAAGGCTTCTGGCCTCAACATTAAAGACACCTATATGCACTGGGTGCGACAGGCG 120
    S  C  K  A  S  G  L  N  I  K  D  T  Y  M  H  W  V  R  Q  A

CDR2
121 CCTGGACAGGGCCTGGAGTGGATTGGAAGGATTGATCCTGCGAATGGTAATACTAAATTT 180
    P  G  Q  G  L  E  W  I  G  R  I  D  P  A  N  G  N  T  K  F

181 GACCCGAAGTTCCAGGGCAGAGCCACTATAACAGCAGACACATCCACGAGCACAGCCTAC 240
    D  P  K  F  Q  G  R  A  T  I  T  A  D  T  S  T  S  T  A  Y

CDR3
241 ATGGAGCTCAGCAGCCTGAGATCTGAGGACACTGCCGTCTATTACTGTGCTAGAGGCGTC 300
    M  E  L  S  S  L  R  S  E  D  T  A  V  Y  Y  C  A  R  G  V

301 TTTGGCTTTTTTGACTACTGGGGCCAAGGGACCACTGTGACAGTCTCCTCAGCCTCCACC 360
    F  G  F  F  D  Y  W  G  Q  G  T  T  V  T  V  S  S  A  S  T

361 AAGGGCCCATCGGTCTTCCCCCTGGCACCCTCCTCCAAGAGCACCTCTGGGGGCACAGCG 420
    K  G  P  S  V  F  P  L  A  P  S  S  K  S  T  S  G  G  T  A

421 GCCCTGGGCTGCCTGGTCAAGGACTACTTCCCCGAACCGGTGACGGTGTCGTGGAACTCA 480
    A  L  G  C  L  V  K  D  Y  F  P  E  P  V  T  V  S  W  N  S

481 GGCGCCCTGACCAGCGGCGTGCACACCTTCCCGGCTGTCCTACAGTCCTCAGGACTCTAC 540
    G  A  L  T  S  G  V  H  T  F  P  A  V  L  Q  S  S  G  L  Y

541 TCCCTCAGCAGCGTGGTGACCGTGCCCTCCAGCAGCTTGGGCACCCAGACCTACATCTGC 600
    S  L  S  S  V  V  T  V  P  S  S  S  L  G  T  Q  T  Y  I  C

601 AACGTGAATCACAAGCCCAGCAACACCAAGGTGGACAAGAAAGTTGAGCCCAAATCTTGT 660
    N  V  N  H  K  P  S  N  T  K  V  D  K  K  V  E  P  K  S  C

661 GACAAGACTCACACATGCCCACCGTGCCCAGCACCTGAACTCCTGGGGGGACCGTCAGTC 720
    D  K  T  H  T  C  P  P  C  P  A  P  E  L  L  G  G  P  S  V

721 TTCCTCTTCCCCCCAAAACCCAAGGACACCCTCATGATCTCCCGGACCCCTGAGGTCACA 780
    F  L  F  P  P  K  P  K  D  T  L  M  I  S  R  T  P  E  V  T
```

*Fig. 10A*

```
 781 TGCGTGGTGGTGGACGTGAGCCACGAAGACCCTGAGGTCAAGTTCAACTGGTACGTGGAC 840
       C   V   V   V   D   V   S   H   E   D   P   E   V   K   F   N   W   Y   V   D

841 GGCGTGGAGGTGCATAATGCCAAGACAAAGCCGCGGGAGGAGCAGTACAACAGCACGTAC 900
       G   V   E   V   H   N   A   K   T   K   P   R   E   E   Q   Y   N   S   T   Y

901 CGTGTGGTCAGCGTCCTCACCGTCCTGCACCAGGACTGGCTGAATGGCAAGGAGTACAAG 960
       R   V   V   S   V   L   T   V   L   H   Q   D   W   L   N   G   K   E   Y   K

961 TGCAAGGTCTCCAACAAAGCCCTCCCAGCCCCCATCGAGAAAACCATCTCCAAAGCCAAA 1020
       C   K   V   S   N   K   A   L   P   A   P   I   E   K   T   I   S   K   A   K

1021 GGGCAGCCCCGAGAACCACAGGTGTACACCCTGCCCCCATCCCGGGATGAGCTGACCAAG 1080
       G   Q   P   R   E   P   Q   V   Y   T   L   P   P   S   R   D   E   L   T   K

1081 AACCAGGTCAGCCTGACCTGCCTGGTCAAAGGCTTCTATCCCAGCGACATCGCCGTGGAG 1140
       N   Q   V   S   L   T   C   L   V   K   G   F   Y   P   S   D   I   A   V   E

1141 TGGGAGAGCAATGGGCAGCCGGAGAACAACTACAAGACCACGCCTCCCGTGTTGGACTCC 1200
       W   E   S   N   G   Q   P   E   N   N   Y   K   T   T   P   P   V   L   D   S

1201 GACGGCTCCTTCTTCCTCTACAGCAAGCTCACCGTGGACAAGAGCAGGTGGCAGCAGGGG 1260
       D   G   S   F   F   L   Y   S   K   L   T   V   D   K   S   R   W   Q   Q   G

1261 AACGTCTTCTCATGCTCCGTGATGCATGAGGCTCTGCACAACCACTACACGCAGAAGAGC 1320
       N   V   F   S   C   S   V   M   H   E   A   L   H   N   H   Y   T   Q   K   S

1321 CTCTCCCTGTCTCCCGGGAAATGA 1344    (SEQ ID NO:39)
       L   S   L   S   P   G   K   *         (SEQ ID NO:40)
```

*Fig. 10A*
(Continued)

Sequence of Hu-11K2 Heavy Chain, Version 2

```
1   CAGGTTCAGCTGGTGCAGTCTGGGGCAGAGGTGAAGAAGCCCGGGTCCTCAGTCAAGGTC  60
    Q  V  Q  L  V  Q  S  G  A  E  V  K  K  P  G  S  S  V  K  V

CDR1
61  TCCTGCAAGGCTTCAGGCCTCACCATTAGCGACACCTATATGCACTGGGTGCGACAGGCG 120
    S  C  K  A  S  G  L  T  I  S  D  T  Y  M  H  W  V  R  Q  A

CDR2
121 CCTGGACAGGGCCTCGAGTGGATGGGAAGGATTGATCCTGCGAATGGTAATACTAAATTT 180
    P  G  Q  G  L  E  W  M  G  R  I  D  P  A  N  G  N  T  K  F

181 GACCCGAAGTTCCAGGGCAGAGTCACTATAACTGCAGACACATCCACGAGCACAGCCTAC.240
    D  P  K  F  Q  G  R  V  T  I  T  A  D  T  S  T  S  T  A  Y

CDR3
241 ATGGAGCTCAGCAGCCTGAGATCTGAGGACACTGCCGTCTATTACTGTGCTAGAGGCGTC 300
    M  E  L  S  S  L  R  S  E  D  T  A  V  Y  Y  C  A  R  G  V

301 TTTGGCTTTTTTGACTACTGGGGCCAAGGGACCACTGTGACAGTCTCCTCAGCCTCCACC 360
    F  G  F  F  D  Y  W  G  Q  G  T  T  V  T  V  S  S  A  S  T

361 AAGGGCCCATCGGTCTTCCCCCTGGCACCCTCCTCCAAGAGCACCTCTGGGGGCACAGCG 420
    K  G  P  S  V  F  P  L  A  P  S  S  K  S  T  S  G  G  T  A

421 GCCCTGGGCTGCCTGGTCAAGGACTACTTCCCCGAACCGGTGACGGTGTCGTGGAACTCA 480
    A  L  G  C  L  V  K  D  Y  F  P  E  P  V  T  V  S  W  N  S

481 GGCGCCCTGACCAGCGGCGTGCACACCTTCCCGGCTGTCCTACAGTCCTCAGGACTCTAC 540
    G  A  L  T  S  G  V  H  T  F  P  A  V  L  Q  S  S  G  L  Y

541 TCCCTCAGCAGCGTGGTGACCGTGCCCTCCAGCAGCTTGGGCACCCAGACCTACATCTGC 600
    S  L  S  S  V  V  T  V  P  S  S  S  L  G  T  Q  T  Y  I  C

601 AACGTGAATCACAAGCCCAGCAACACCAAGGTGGACAAGAAAGTTGAGCCCAAATCTTGT 660
    N  V  N  H  K  P  S  N  T  K  V  D  K  K  V  E  P  K  S  C

661 GACAAGACTCACACATGCCCACCGTGCCCAGCACCTGAACTCCTGGGGGGACCGTCAGTC 720
    D  K  T  H  T  C  P  P  C  P  A  P  E  L  L  G  G  P  S  V

721 TTCCTCTTCCCCCCAAAACCCAAGGACACCCTCATGATCTCCCGGACCCCTGAGGTCACA 780
    F  L  F  P  P  K  P  K  D  T  L  M  I  S  R  T  P  E  V  T
```

*Fig. 10B*

```
781 TGCGTGGTGGTGGACGTGAGCCACGAAGACCCTGAGGTCAAGTTCAACTGGTACGTGGAC 840
     C  V  V  V  D  V  S  H  E  D  P  E  V  K  F  N  W  Y  V  D

841 GGCGTGGAGGTGCATAATGCCAAGACAAAGCCGCGGGAGGAGCAGTACAACAGCACGTAC 900
     G  V  E  V  H  N  A  K  T  K  P  R  E  E  Q  Y  N  S  T  Y

901 CGTGTGGTCAGCGTCCTCACCGTCCTGCACCAGGACTGGCTGAATGGCAAGGAGTACAAG 960
     R  V  V  S  V  L  T  V  L  H  Q  D  W  L  N  G  K  E  Y  K

961 TGCAAGGTCTCCAACAAAGCCCTCCCAGCCCCCATCGAGAAAACCATCTCCAAAGCCAAA 1020
     C  K  V  S  N  K  A  L  P  A  P  I  E  K  T  I  S  K  A  K

1021 GGGCAGCCCCGAGAACCACAGGTGTACACCCTGCCCCCATCCCGGGATGAGCTGACCAAG 1080
      G  Q  P  R  E  P  Q  V  Y  T  L  P  P  S  R  D  E  L  T  K

1081 AACCAGGTCAGCCTGACCTGCCTGGTCAAAGGCTTCTATCCCAGCGACATCGCCGTGGAG 1140
      N  Q  V  S  L  T  C  L  V  K  G  F  Y  P  S  D  I  A  V  E

1141 TGGGAGAGCAATGGGCAGCCGGAGAACAACTACAAGACCACGCCTCCCGTGTTGGACTCC 1200
      W  E  S  N  G  Q  P  E  N  N  Y  K  T  T  P  P  V  L  D  S

1201 GACGGCTCCTTCTTCCTCTACAGCAAGCTCACCGTGGACAAGAGCAGGTGGCAGCAGGGG 1260
      D  G  S  F  F  L  Y  S  K  L  T  V  D  K  S  R  W  Q  Q  G

1261 AACGTCTTCTCATGCTCCGTGATGCATGAGGCTCTGCACAACCACTACACGCAGAAGAGC 1320
      N  V  F  S  C  S  V  M  H  E  A  L  H  N  H  Y  T  Q  K  S

1321 CTCTCCCTGTCTCCCGGGAAATGA 1344   (SEQ ID NO:41)
      L  S  L  S  P  G  K  *        (SEQ ID NO:42)
```

*Fig. 10B*
(Continued)

Sequence of Hu-11K2 Light Chain, Version 1

```
  1 GACATTCAGATGACTCAGTCTCCATCCTCCCTGTCAGCATCTGTGGGAGACAGAGTCACC  60
     D  I  Q  M  T  Q  S  P  S  S  L  S  A  S  V  G  D  R  V  T

CDR1
 61 ATTACTTGCAAGGCAACTGAGGACATATATAATCGATTAGCCTGGTATCAGCAGAAACCA 120
     I  T  C  K  A  T  E  D  I  Y  N  R  L  A  W  Y  Q  Q  K  P

CDR2
121 GGAAAGGCCCCTAAGCTCTTAATTTCTGGTGCAACCAGTTTGGAGACTGGGGTTCCTTCA 180
     G  K  A  P  K  L  L  I  S  G  A  T  S  L  E  T  G  V  P  S

181 AGATTCAGTGGCAGTGGATCTGGAAAAGATTACACTCTCACCATTAGCAGTCTACAGCCT 240
     R  F  S  G  S  G  S  G  K  D  Y  T  L  T  I  S  S  L  Q  P

CDR3
241 GAGGATTTTGCTACTTATTACTGTCAACAGTTTTGGAGTGCTCCGTACACGTTCGGAGGG 300
     E  D  F  A  T  Y  Y  C  Q  Q  F  W  S  A  P  Y  T  F  G  G

301 GGGACCAAGGTGGAGATCAAACGAACTGTGGCTGCACCATCTGTCTTCATCTTCCCGCCA 360
     G  T  K  V  E  I  K  R  T  V  A  A  P  S  V  F  I  F  P  P

361 TCTGATGAGCAGTTGAAATCTGGAACTGCCTCTGTTGTGTGCCTGCTGAATAACTTCTAT 420
     S  D  E  Q  L  K  S  G  T  A  S  V  V  C  L  L  N  N  F  Y

421 CCCAGAGAGGCCAAAGTACAGTGGAAGGTGGATAACGCCCTCCAATCGGGTAACTCCCAG 480
     P  R  E  A  K  V  Q  W  K  V  D  N  A  L  Q  S  G  N  S  Q

481 GAGAGTGTCACAGAGCAGGACAGCAAGGACAGCACCTACAGCCTCAGCAGCACCCTGACG 540
     E  S  V  T  E  Q  D  S  K  D  S  T  Y  S  L  S  S  T  L  T

541 CTGAGCAAAGCAGACTACGAGAAACACAAAGTCTACGCCTGCGAAGTCACCCATCAGGGC 600
     L  S  K  A  D  Y  E  K  H  K  V  Y  A  C  E  V  T  H  Q  G

601 CTGAGCTCGCCCGTCACAAAGAGCTTCAACAGGGGAGAGTGTTAG 645    (SEQ ID NO: 43)
     L  S  S  P  V  T  K  S  F  N  R  G  E  C  *           (SEQ ID NO: 44)
```

*Fig. 10C*

Sequence of Hu-11K2 Light Chain, Version 2

```
  1 GACATTCAGATGACTCAGTCTCCATCCTCCCTGTCAGCATCTGTGGGAGACAGAGTCACC  60
    D  I  Q  M  T  Q  S  P  S  S  L  S  A  S  V  G  D  R  V  T

CDR1
 61 ATTACTTGCAAGGCAACTGAGGACATATATAATCGATTAGCCTGGTATCAGCAGAAACCA 120
    I  T  C  K  A  T  E  D  I  Y  N  R  L  A  W  Y  Q  Q  K  P

CDR2
121 GGAAAGGCCCCTAAGCTCTTAATTTCTGGTGCAACCAGTTTGGAGACTGGGGTTCCTTCA 180
    G  K  A  P  K  L  L  I  S  G  A  T  S  L  E  T  G  V  P  S

181 AGATTCAGTGGCAGTGGATCCGGAACAGATTACACTCTCACCATTAGCAGTCTACAGCCT 240
    R  F  S  G  S  G  S  G  T  D  Y  T  L  T  I  S  S  L  Q  P

CDR3
241 GAGGATTTTGCTACTTATTACTGTCAACAGTTTTGGAGTGCTCCGTACACGTTCGGAGGG 300
    E  D  F  A  T  Y  Y  C  Q  Q  F  W  S  A  P  Y  T  F  G  G

301 GGGACCAAGGTGGAGATCAAACGAACTGTGGCTGCACCATCTGTCTTCATCTTCCCGCCA 360
    G  T  K  V  E  I  K  R  T  V  A  A  P  S  V  F  I  F  P  P

361 TCTGATGAGCAGTTGAAATCTGGAACTGCCTCTGTTGTGTGCCTGCTGAATAACTTCTAT 420
    S  D  E  Q  L  K  S  G  T  A  S  V  V  C  L  L  N  N  F  Y

421 CCCAGAGAGGCCAAAGTACAGTGGAAGGTGGATAACGCCCTCCAATCGGGTAACTCCCAG 480
    P  R  E  A  K  V  Q  W  K  V  D  N  A  L  Q  S  G  N  S  Q

481 GAGAGTGTCACAGAGCAGGACAGCAAGGACAGCACCTACAGCCTCAGCAGCACCCTGACG 540
    E  S  V  T  E  Q  D  S  K  D  S  T  Y  S  L  S  S  T  L  T

541 CTGAGCAAAGCAGACTACGAGAAACACAAAGTCTACGCCTGCGAAGTCACCCATCAGGGC 600
    L  S  K  A  D  Y  E  K  H  K  V  Y  A  C  E  V  T  H  Q  G

601 CTGAGCTCGCCCGTCACAAAGAGCTTCAACAGGGGAGAGTGTTAG 645    (SEQ ID NO: 45)
    L  S  S  P  V  T  K  S  F  N  R  G  E  C  *         (SEQ ID NO: 46)
```

11K2 Light Chains

```
Hu11K2-ver1  ------------p---l-a-v---------------------------------k--k------------------
Hu11K2-ver2  ------------p---l-a-v---------------------------------k--k---------------t--
Mouse        DIQMTQSSSSFSVSLGDRVTITCKATEDIYNRLAWYQQKPGSAPRLLISGATSLETGVPSRFSGSGSGKD Hu11K2-ver1  ---t-s---p--f--------------------v---          (SEQ ID NO: 49)
Hu11K2-ver2  ---t-s---p--f--------------------v---          (SEQ ID NO: 50)
Mouse        YTLSITSLQTEDVATYYCQQFWSAPYTFGGGTKLEIK          (SEQ ID NO: 28)
```

Fig. 11B

11K2 Heavy Chains

```
Hu11K2-ver1  q---v-------vk-p-s------v--k----------------r-a-g----------------r---
Hu11K2-ver2  q---v-------vk-p-s------v--k-----t-s--------r-a-g-----m--------rv---
Mouse        EVQLQQSGAELVKAGASVKLSCPASGLNIKDTYMHWVKQRPEQGLEWIGRIDPANGNTKFDPKFQGKATI Hu11K2-ver1  ------ts-----me----r-----------------------------v----        (SEQ ID NO: 47)
Hu11K2-ver2  ------ts-----me----r-----------------------------v----        (SEQ ID NO: 48)
Mouse        TADTSSNTAYLQLSSLTSEDTAVYYCARGVFGFFDYWGQGTTLTVSS                (SEQ ID NO: 27)
```

*CDR sequences in bold and underlined
*Dashes indicate identity

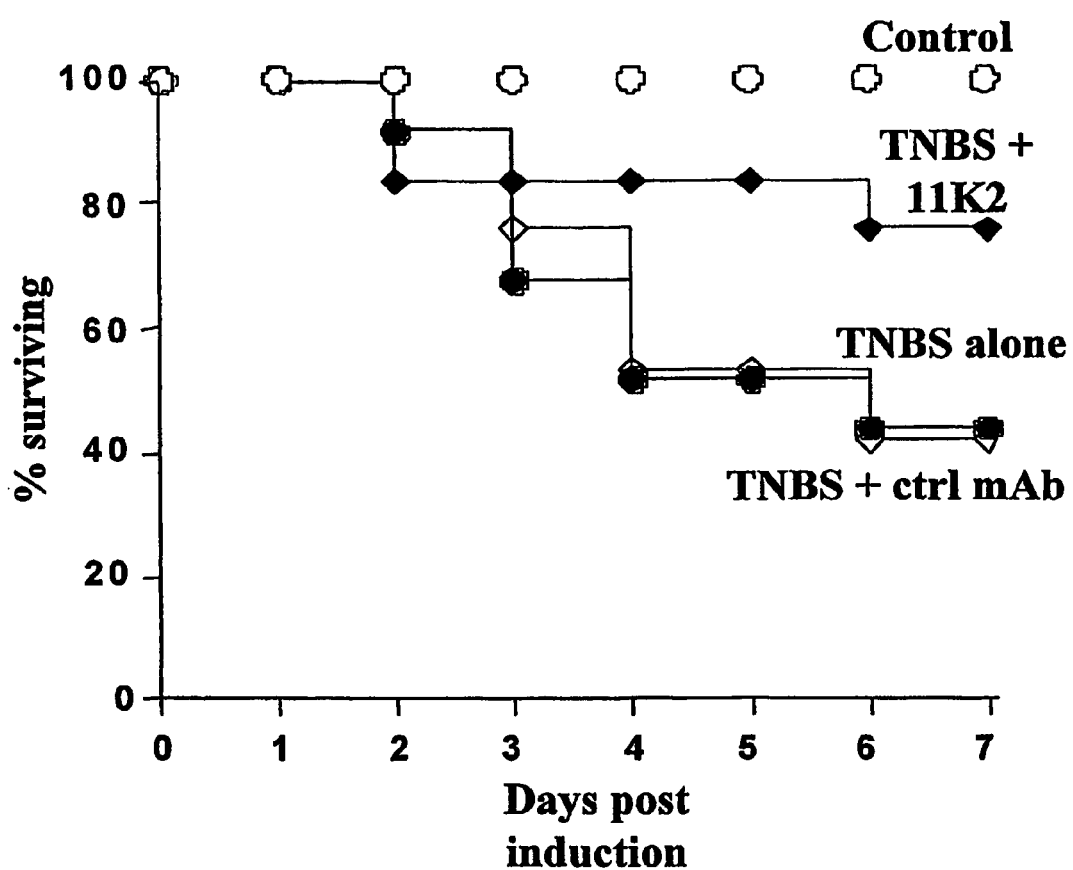

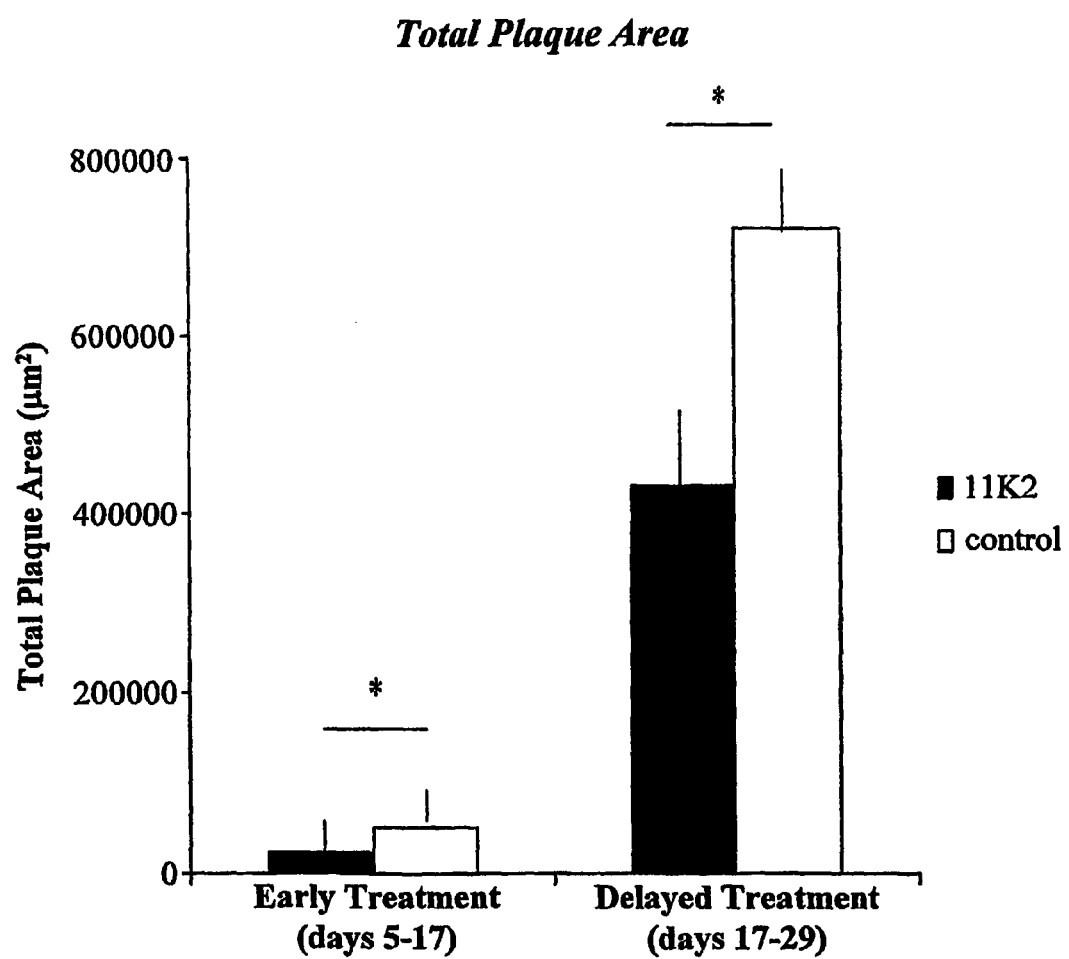

HUMANIZED ANTIBODIES AGAINST MONOCYTE CHEMOTACTIC PROTEINS

RELATED APPLICATIONS

This is national phase application under 37 U.S.C. §371 of PCT/US2003/037834, filed Nov. 27, 2003, which claims the benefit of U.S. provisional application 60/430,007 filed Nov. 27, 2002. The entire contents of each of these patents and patent applications are hereby incorporated herein by reference.

BACKGROUND OF THE INVENTION

"Chemokines," which take their name from chemotactic cytokines are small secreted polypeptides that regulate movement of immune cells into tissues (Baggiolini et al. (1994) *Adv. Immunol.* 55:97-179; Oppenheim et al. (1991) *Ann Rev. Immunol.* 9:617-648). Chemokines are assigned to three different families based on the number and position of conserved cysteine residues (Van Coillie et al. (1999) *Cytokine & Growth Factor Rev.* 10:61-86). The a and b chemokines each contain four conserved cysteine residues. The first two cysteines of the a chemokines are separated by a single amino acid, thus containing a CXC amino acid motif. The first two conserved cysteines of the b chemokines are adjacent. Thus, the b chemokines are also known as C—C chemokines. By contrast, lymphotactin is the sole member of the third family of chemokines, and contains only the second and fourth conserved cysteine residues. Interestingly, in humans, a chemokines are all encoded by genes on chromosome 4, b chemokines are all encoded by genes on chromosome 17, and lymphotaxin is encoded by genes on chromosome 1.

The b-chemokines form a gradient that serves as a chemoattractant and potential proliferation signal for immune and other cells such as monocytes, macrophages, basophils, eosinophils, T lymphocytes and fibroblasts. MCP-1, MCP-2 and MCP-3 share sequence homology with one another at the amino acid level. Through interaction with specific receptors, termed C—C chemokine receptors (CCR) which are G-protein coupled, seven transmembrane receptors (Rossi and Zlotnik (2000) *Ann. Rev. Immunol.* 18:217-242), the b-chemokines regulate the expression of adhesion molecules on endothelial cells and thereby indirectly affect diapedesis and extravasation of immune cells from the circulation into tissues. There are ten different CCRs (CCR1 through CCR10). CCR2 acts as a receptor for MCP-1, MCP-2, MCP-3, and MCP-4 (Rossi and Zlotnik (2000) *Ann. Rev. Immunol.* 18:217-242). However, all human MCPs have been shown to interact with more than one receptor (Van Coillie et al. (1999) *Cytokine & Growth Factor Rev.* 10:61-86).

Human MCP-1, MCP-2 and MCP-3 all have chemotactic activity for a variety of cell types, including T lymphocytes and monocytes (Van Coillie et al. (1999) *Cytokine & Growth Factor Rev.* 10:61-86). Other shared functions of MCP-1, MCP-2, and MCP-3 include induction of N-acetyl b-D-glucosaminidase release, gelatinase B release, and granzyme A release which are believed to help the cells digest the extracellular matrix components necessary to enable them to migrate into tissues (Van Coillie et al. (1999) *Cytokine & Growth Factor Rev.* 10:61-86). In addition, MCP-1 and MCP-3 share various functions, such as induction of arachidonic acid release and stimulation of a respiratory burst (Van Coillie et al. (1999) *Cytokine & Growth Factor Rev.* 10:61-86).

MCP-1-specific antibodies have previously been described in the literature (WO-01/89582, WO 01/89565, Luo et al. (1994) *J Immunol* 153:3708-16; Traynor, et al (2002) *J Immunol* 168:4659-66). Certain MCP-1 antibodies have been described as binding MCP-1 and MCP-3, specifically the MRHAS domain of MCP-1 and MCP-3 (WO 95/09232). In addition, a human anti-MCP-1 antibody has also been described (WO 02/02640). There is a need in the art to identify antibodies which can be used to manipulate b-chemokines in general, and to specifically modulate the activity of multiple chemokines, e.g., MCP-1 and MCP-2 or MCP-3.

SUMMARY OF THE INVENTION

The present invention features new immunological reagents, in particular, therapeutic antibody reagents for the prevention and treatment of disorders associated with detrimental MCP activity. The invention is based, at least in part, on the identification and characterization of two monoclonal pan-antibodies that specifically bind to MCPs and are effective at binding MCPs, including MCP-1 and MCP-2, with high affinity and at inhibiting MCP-induced chemotaxis. Structural and functional analysis of these antibodies leads to the design of various humanized antibodies for prophylactic and/or therapeutic use. In particular, the invention features humanization of the variable regions of these antibodies and, accordingly provides for humanized immunoglobulin or antibody chains, intact humanized immunoglobulins or antibodies, and functional immunoglobulin or antibody fragments, in particular, antigen binding fragments, of the featured antibodies.

Polypeptides comprising the complementarity determining regions of the featured monoclonal antibodies are also disclosed, as are polynucleotide reagents, vectors and host suitable for encoding said polypeptides.

Methods of treatment of disorders associated with detrimental MCP activity are disclosed, as are pharmaceutical compositions and kits for use in such applications.

Also featured are methods of identifying residues within the featured monoclonal antibodies which are important for proper immunologic function and for identifying residues which are amenable to substitution in the design of humanized antibodies having improved binding affinities and/or reduced immunogenicity, when used as therapeutic reagents.

In one embodiment, the invention features a humanized immunoglobulin heavy chain or antigen-binding fragment thereof comprising variable region complementary determining regions (CDRs) from the 11K2 immunoglobulin heavy chain variable region sequence set forth as SEQ D NO: 27, and variable framework regions from a human acceptor immunoglobulin heavy chain sequence, provided that at least one framework residue is substituted with the corresponding amino acid residue from the mouse 11K2 heavy chain variable region sequence, wherein the framework residue is selected from the group consisting of:

a residue that non-covalently binds antigen directly;

a residue adjacent to a CDR;

a CDR-interacting residue; and a residue participating in the VL-VH interface.

In another embodiment, the invention features a humanized immunoglobulin light chain or antigen-binding fragment thereof comprising variable region complementary determining regions (CDRs) from the 11K2 immunoglobulin light chain variable region sequence set forth as SEQ ID NO: 28 and variable framework regions from a human acceptor immunoglobulin light chain, provided that at least one framework residue is substituted with the corresponding amino acid residue from the mouse 11K2 light chain variable region sequence, wherein the framework residue is selected from the group consisting of:

a residue that non-covalently binds antigen directly;
a residue adjacent to a CDR;
a CDR-interacting residue; and
a residue participating in the VL-VH interface.

In some embodiments, a CDR-interacting residue is identified by modeling the 11K2 heavy chain based on the solved structure of a murine immunoglobulin heavy chain that shares at least 70%, 80%, or 90% sequence identity with the 11K2 heavy chain. In other embodiments, a CDR-interacting residue is identified by modeling the 11K2 light chain based on the solved structure of a murine immunoglobulin light chain that shares at least 70%, 80%, or 90% sequence identity with the 11K2 light chain.

Another embodiment of the invention features a humanized immunoglobulin heavy chain or antigen-binding fragment thereof comprising variable region complementary determining regions (CDRs) from the 11K2 immunoglobulin heavy chain variable region sequence set forth as SEQ ID NO: 27, and variable framework regions from a human acceptor immunoglobulin heavy chain sequence, provided that at least one framework residue is substituted with the corresponding amino acid residue from the mouse 11K2 heavy chain variable region sequence, wherein the framework residue is a residue capable of affecting heavy chain variable region conformation or function as identified by analysis of a three-dimensional model of the variable region.

In yet other embodiments, the invention describes a humanized immunoglobulin light chain or antigen-binding fragment thereof comprising variable region complementary determining regions (CDRS) from the 11K2 immunoglobulin light chain variable region sequence set forth as SEQ ID NO: 28, and variable framework regions from a human acceptor immunoglobulin light chain, provided that at least one framework residue is substituted with the corresponding amino acid residue from the mouse 11K2 light chain variable region sequence, wherein the framework residue is a residue capable of affecting light chain variable region conformation or function as identified by analysis of a three-dimensional model of the variable region.

In some embodiments, the framework residue is selected from the group consisting of a residue capable of interacting with antigen, a residue proximal to the antigen-binding site, a residue capable of interacting with a CDR, a residue adjacent to a CDR, a residue within 6 Å of a CDR residue, a canonical residue, a vernier zone residue, an interchain packing residue, and a rare residue. In other embodiments, the framework residue is selected from the group consisting of a residue capable of interacting with antigen, a residue proximal to the antigen-binding site, a residue capable of interacting with a CDR, a residue adjacent to a CDR, a residue within 6 Å of a CDR residue, a canonical residue, a vernier zone residue, an interchain packing residue, and an unusual residue.

In still other embodiments, the framework residue is identified by modeling the 11K2 heavy chain based on the solved structure of a murine immunoglobulin heavy chain that shares at least 70%, 80%, or 90% sequence identity with the 11K2 heavy chain. In still other embodiments, the framework residue is identified by modeling the 11K2 light chain based on the solved structure of a murine immunoglobulin light chain that shares at least 70%, 80%, or 90% sequence identity with the 11K2 light chain.

In one embodiment, the invention features a humanized antibody or antigen-binding fragment thereof comprising the complementary determining regions (CDR1, CDR2 and CDR3) of the 11K2 variable heavy chain sequence set forth as SEQ ID NO: 27. The invention also features a humanized antibody comprising the complementary determining regions (CDR1, CDR2 and CDR3) of the 11K2 variable light chain sequence set forth as SEQ ID NO: 28. In still another embodiment, the invention features a humanized antibody, or antigen-binding fragment thereof, which specifically binds to MCP-1 comprising variable region comprising complementary determining regions (CDRs) corresponding to CDRs from the mouse 11K2 antibody. In some embodiments, the fragment of the invention is a Fab fragment.

In yet another embodiment, the invention features a chimeric immunoglobulin comprising a variable region sequence substantially as set forth in SEQ ID NO: 27 or SEQ ID NO: 28, and constant region sequences from a human immunoglobulin.

In one embodiment, the invention features a humanized antibody comprising the complementary determining regions (CDR1, CDR2 and CDR3) of the 11K2 variable heavy chain sequence set forth as SEQ ID NO: 27. In another embodiment, the invention features a humanized antibody comprising the complementary determining regions (CDR1, CDR2 and CDR3) of the 11K2 variable light chain sequence set forth as SEQ ID NO: 28.

In another embodiment, the invention features a humanized antibody, or antigen-binding fragment thereof, which specifically binds to MCP-1 comprising variable region comprising complementary determining regions (CDRs) corresponding to CDRs from the mouse 11K2 antibody. The invention also describes a chimeric immunoglobulin comprising a variable region sequence substantially as set forth in SEQ ID NO: 27 or SEQ ID NO: 28, and constant region sequences from a human immunoglobulin.

In yet another embodiment, the invention features a method for identifying residues amenable to substitution in a humanized 11K2 immunoglobulin variable framework region, comprising modeling the three-dimensional structure of the 11K2 variable region based on a solved immunoglobulin structure and analyzing said model for residues capable of affecting 11K2 immunoglobulin variable region conformation or function, such that residues amenable to substitution are identified. The invention also features use of the variable region sequence set forth as SEQ ID NO: 27 or SEQ ID NO: 28, or any portion thereof, in producing a three-dimensional image of a 11K2 immunoglobulin, 11K2 immunoglobulin chain, or domain thereof.

In still another embodiment, the invention features a method of treating a disorder associated with detrimental MCP activity in a subject by administering a nucleic acid molecule that encodes an immunoglobulin heavy chain comprising the amino acid sequence of SEQ ID NO: 47 or the amino acid sequence of SEQ ID NO: 48 and a nucleic acid molecule that encodes an immunoglobulin light chain comprising the amino acid sequence of SEQ ID NO: 49 or the amino acid sequence of SEQ ID NO: 50, under conditions such that said immunoglobulin chains are expressed, thereby treating the subject.

In one embodiment, the invention features a humanized immunoglobulin comprising the heavy chain set forth in SEQ ID NO: 47. In another embodiment, the invention features a humanized immunoglobulin comprising the heavy chain set forth in SEQ ID NO: 48. In still another embodiment, the invention features a humanized immunoglobulin comprising the light chain set forth in SEQ ID NO: 49. In yet another embodiment, the invention features a humanized immunoglobulin comprising the light chain set forth in SEQ ID NO: 50.

In one embodiment, the invention features a heavy chain comprising a complementarity determining region (CDR) and at least one variable region framework residue from the monoclonal antibody 11K2 heavy chain set forth as SEQ ID NO: 27, wherein the residue is selected from the group consisting of L27, I29, and T73 (Kabat 15' numbering convention), and wherein the remainder of the heavy chain is from a human immunoglobulin. In one embodiment, the heavy chain comprises variable region framework residues L27, I29, and T73. In another embodiment, the heavy chain further comprises at least one variable region framework residue selected from the group consisting of N28, K30, I48, and A67 (Kabat numbering convention). In still another embodiment of the invention, the heavy chain comprises variable region framework residues N28, K30, I48, and A67.

In another embodiment, the invention features a light chain comprising a complementarity determining region (CDR) and at least one variable region framework residue from the monoclonal antibody 11K2 light chain set forth as SEQ ID NO: 28, wherein the residue is selected from the group consisting of S49 and Y71 (Kabat numbering convention), and wherein the remainder of the light chain is from a human immunoglobulin. In one embodiment, the light chain comprises variable region framework residues S49 and Y71. In another embodiment, the light chain further comprises variable region framework residue K69 (Kabat numbering convention).

In another embodiment, the invention features a humanized immunoglobulin or antigen-binding fragment thereof comprising heavy chain complementary determining regions as set forth in SEQ ID NO: 29, SEQ ID NO: 30, and SEQ ID NO: 31, and at least one variable region framework residue from the monoclonal antibody 11K2 heavy chain set forth as SEQ ID NO: 27, wherein the residue is selected from the group consisting of L27, N28, I29, K30, I48, A67, and T73 (Kabat numbering). In one embodiment, the heavy chain comprises variable region framework residues L27, N28, I29, K30, I48, A67, and T73. In another embodiment, the heavy chain comprises variable region framework residues L27, I29, and T73.

In yet another embodiment, the invention features a humanized immunoglobulin or antigen-binding fragment thereof comprising light chain complementary determining regions as set forth in SEQ ID NO: 32, SEQ ID NO: 33, and SEQ ID NO: 34, and at least one variable region framework residues from the monoclonal antibody 11K2 light chain set forth as SEQ ID NO: 28, wherein the residue is selected from the group consisting of S49, K69, and Y71 (Kabat numbering). In one embodiment, the light chain comprises variable region framework residues S49, K69, and Y71. In another embodiment, the light chain further comprises variable region framework residues S49 and Y71.

In still another embodiment, the invention describes a humanized immunoglobulin or antigen-binding fragment comprising the light chain of the invention and the heavy chain of the invention.

In one embodiment, the invention features a humanized immunoglobulin or antigen-binding fragment comprising
  a) a heavy chain comprising a complementarity determining region (CDR) and at least one variable region framework residue from the monoclonal antibody 11K2 heavy chain set forth as SEQ ID NO: 27, wherein the residue is selected from the group consisting of L27, N28, I29, K30, I48, A67 and T73 (Kabat numbering convention), and
  b) a light chain comprising a complementarity determining region (CDR) and at least one variable region framework residue from the monoclonal antibody 11K2 light chain set forth as SEQ ID NO: 28, wherein the residue is selected from the group consisting of S49, K69, and Y71 (Kabat numbering convention), wherein the remainder of the heavy and light chains are from a human immunoglobulin. In a certain embodiment, the heavy chain comprises variable region framework residues L27, I29, and T73, and the light chain comprises variable region framework residues S49 and Y71. In another embodiment, the heavy chain comprises variable region framework residues L27, N28, I29, K30, I48, A67 and T73, and the light chain comprises variable region framework residues S49, K69, and Y71. In yet another embodiment, the heavy chain comprises variable region framework residues L27, I29, and T73, and the light chain comprises variable region framework residues S49, K69, and Y71. In yet a further embodiment, the heavy chain comprises variable region framework residues L27, N28, I29, K30, I48, A67 and T73, and the light chain comprises variable region framework residues S49 and Y71.

In one embodiment, the invention features a humanized immunoglobulin or antigen-binding fragment comprising
  a) heavy chain complementary determining regions as set forth in SEQ ID NO: 29, SEQ ID NO: 30, and SEQ ID NO: 31, and variable region framework residues L27, N28, I29, K30, I48, A67, and 173 (Kabat numbering) from the monoclonal antibody 11K2 heavy chain set forth as SEQ ID NO: 27, and
  b) light chain complementary determining regions as set forth in SEQ ID NO: 32, SEQ ID NO: 33, and SEQ ID NO: 34, and variable region framework residues S49, K69, and Y71 (Kabat numbering), from the monoclonal antibody 11K2 light chain set forth as SEQ ID NO: 28, wherein the remainder of the heavy and light chains are from a human immunoglobulin. In one embodiment of the invention, the immunoglobulin is modified by reducing or eliminating at least one potential glycosylation site.

In one embodiment, the immunoglobulin or antigen-binding fragment of the invention, binds to MCP-1. In one embodiment, the immunoglobulin or antigen-binding fragment of the invention, specifically binds to MCP-1 with a binding affinity of at least $10^{-9}$ M. In another embodiment, the immunoglobulin or antigen-binding fragment of the invention, specifically binds to MCP-1 with a binding affinity of at least $10^{-10}$ M. In still another embodiment, the immunoglobulin or antigen-binding fragment of the invention specifically binds to MCP-1 with a binding affinity of at least $10^{-11}$ M. In still another embodiment, the immunoglobulin or antigen-binding fragment of the invention, further binds to MCP-2 with a binding affinity of at least $10^{-7}$ M. In another embodiment, the immunoglobulin or antigen-binding fragment of the invention, further binds to MCP-2 with a binding affinity of at least $10^{-8}$ M. In yet another embodiment, the immunoglobulin or antigen-binding fragment of the invention, further binds to MCP-2 with a binding affinity of at least $10^{-9}$ M.

In one embodiment, the immunoglobulin or antigen-binding fragment of the invention binds to MCP-2. In one embodiment, the immunoglobulin or antigen-binding fragment of the invention specifically binds to MCP-2 with a binding affinity of at least $10^{-7}$ M. In yet another embodiment, the immunoglobulin or antigen-binding fragment of the invention specifically binds to MCP-2 with a binding affinity of at least $10^{-8}$ M. In yet another embodiment, the immunoglobulin or antigen-binding fragment of the invention specifically binds to MCP-2 with a binding affinity of at least $10^{-9}$ M.

In one embodiment, the immunoglobulin or antigen-binding fragment of the invention binds to MCP-1 and MCP-2. In another embodiment, the immunoglobulin or antigen-binding fragment of the invention binds to an epitope within MCP-1, MCP-2, and MCP-3.

Another embodiment of the invention features a method of treating a disorder associated with detrimental MCP activity comprising administering to a subject having said disorder, a nucleic acid molecule that encodes an immunoglobulin heavy chain comprising the amino acid sequence of SEQ ID NO: 53 or the amino acid sequence of SEQ ID NO: 54 and a nucleic acid molecule that encodes an immunoglobulin light chain that comprises the amino acid sequence of SEQ ID NO: 55 or the amino acid sequence of SEQ ID NO: 56, under conditions such that said immunoglobulin chains are expressed, such that a beneficial therapeutic response in said subject is generated.

In one embodiment, the invention features an antibody comprising the same heavy and light chain polypeptide sequences as an antibody produced by a CHO cell line secreting humanized 11K2 (version H2L1) clone 3F2 (ATCC patent deposit designation PTA-5308). A hybridoma cell line that produces this monoclonal antibody was deposited at the American Type Culture Collection (ATCC) at 10801 University Boulevard, Manassas, Va., 20110, United States of America, on Jul. 3, 2003, and was assigned ATCC deposit number PTA-5308.

In another embodiment, the invention describes an isolated nucleic acid molecule encoding the heavy chain of the immunoglobulin or antigen-binding fragment of the invention. In another embodiment, the invention features an isolated nucleic acid molecule encoding the light chain of immunoglobulin or antigen-binding fragment of the invention. In still another embodiment, the invention features an isolated nucleic acid molecule encoding the immunoglobulin or antigen-binding fragment of the invention.

In one embodiment, the invention features an isolated nucleic acid molecule comprising a nucleotide sequence corresponding to the amino acid sequence selected from the group consisting of SEQ ID NO: 47, SEQ ID NO: 48, SEQ ID NO: 49, and SEQ ID NO: 50.

In still another embodiment, the invention features an isolated nucleic acid comprising a coding sequence for the heavy chain of an antibody produced by a CHO cell line secreting humanized 11K2 (version H2L1) clone 3F2 (ATCC patent deposit designation PTA-5308). In another embodiment, the invention features an isolated nucleic acid comprising a coding sequence for the light chain of an antibody produced by a CHO cell line secreting humanized 11K2 (version H2L1) clone 3F2 (ATCC patent deposit designation PTA-5308).

In another embodiment, the invention features a cell line of humanized 11K2 (version H2L1) clone 3F2 (ATCC patent deposit designation PTA-5308).

One embodiment of the invention features a humanized immunoglobulin heavy chain or antigen-binding portion thereof comprising variable region complementary determining regions (CDRs) from the 1A1 immunoglobulin heavy chain variable region sequence set forth as SEQ ID NO: 11, and variable framework regions from a human acceptor immunoglobulin heavy chain sequence, provided that at least one framework residue is substituted with the corresponding amino acid residue from the mouse 1A1 heavy chain variable region sequence, wherein the framework residue is selected from the group consisting of:
a residue that non-covalently binds antigen directly,
a residue adjacent to a CDR;
a CDR-interacting residue; and
a residue participating in the VL-VH interface.

The invention features a humanized immunoglobulin heavy chain or antigen-binding portion thereof, wherein a CDR-interacting residue is identified by modeling the 1A1 heavy chain based on the solved structure of a murine immunoglobulin heavy chain that shares at least 70% sequence identity with the 1A1 heavy chain. The invention also features a humanized immunoglobulin heavy chain or antigen-binding portion thereof, wherein a CDR-interacting residue is identified by modeling the 1A1 heavy chain based on the solved structure of a murine immunoglobulin heavy chain that shares at least 80% sequence identity with the 1A1 heavy chain. The invention further features a humanized immunoglobulin heavy chain or antigen-binding portion thereof, wherein a CDR-interacting residue is identified by modeling the 1A1 heavy chain based on the solved structure of a murine immunoglobulin heavy chain that shares at least 90% sequence identity with the 1A1 heavy chain.

In another embodiment, the invention features a humanized immunoglobulin light chain or antigen-binding portion thereof comprising variable region complementary determining regions (CDRs) from the 1A1 immunoglobulin light chain variable region sequence set forth as SEQ ID NO: 12 and variable framework regions from a human acceptor immunoglobulin light chain, provided that at least one framework residue is substituted with the corresponding amino acid residue from the mouse 1A1 light chain variable region sequence, wherein the framework residue is selected from the group consisting of:
a residue that non-covalently binds antigen directly;
a residue adjacent to a CDR;
a CDR-interacting residue; and
a residue participating in the VL-VH interface.

The invention features a humanized immunoglobulin light chain or antigen-binding portion thereof, wherein a CDR-interacting residue is identified by modeling the 1A1 light chain based on the solved structure of a murine immunoglobulin light chain that shares at least 70% sequence identity with the 1A1 light chain. The invention also features a humanized immunoglobulin light chain, wherein a CDR-interacting residue is identified by modeling the 1A1 light chain based on the solved structure of a murine immunoglobulin light chain that shares at least 80% sequence identity with the 1A1 light chain. The invention features a humanized immunoglobulin light chain, wherein a CDR-interacting residue is identified by modeling the 1A1 light chain based on the solved structure of a murine immunoglobulin light chain that shares at least 90% sequence identity with the 1A1 light chain.

In another embodiment, the invention features a humanized immunoglobulin heavy chain or antigen-binding portion thereof comprising variable region complementary determining regions (CDRs) from the 1A1 immunoglobulin heavy chain variable region sequence set forth as SEQ D NO: 11, and variable framework regions from a human acceptor immunoglobulin heavy chain sequence, provided that at least one framework residue is substituted with the corresponding amino acid residue from the mouse 1A1 heavy chain variable region sequence, wherein the framework residue is a residue capable of affecting heavy chain variable region conformation or function as identified by analysis of a three-dimensional model of the variable region 70. The invention also features a humanized immunoglobulin of a heavy chain or antigen-binding portion thereof, wherein the framework residue is selected from the group consisting of a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, and a rare residue.

In another embodiment, the invention features a humanized immunoglobulin light chain or antigen-binding portion thereof, comprising variable region complementary determining regions (CDRs) from the 1A1 immunoglobulin light chain variable region sequence set forth as SEQ ID NO: 12, and variable framework regions from a human acceptor immunoglobulin light chain, provided that at least one framework residue is substituted with the corresponding amino acid residue from the mouse 1A1 light chain variable region sequence, wherein the framework residue is a residue capable of affecting light chain variable region conformation or function as identified by analysis of a three-dimensional model of the variable region. The invention also features a humanized immunoglobulin of a light chain or antigen-binding portion thereof, wherein the framework residue is selected from the group consisting of a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, and an unusual residue.

In one embodiment the invention features a heavy and/or light chain, wherein the framework residue is identified by modeling the 1A1 heavy chain based on the solved structure of a murine immunoglobulin heavy chain that shares at least 70% sequence identity with the 1A1 heavy and/or light chain. In another embodiment the invention features a heavy and/or light chain, wherein the framework residue is identified by modeling the 1A1 heavy or light chain based on the solved structure of a murine immunoglobulin heavy and/or light chain that shares at least 80% sequence identity with the 1A1 heavy or light chain. In another embodiment the invention features a heavy and/or light chain, wherein the framework residue is identified by modeling the 1A1 heavy chain based on the solved structure of a murine immunoglobulin heavy and/or light chain that shares at least 90% sequence identity with the 1A1 heavy or light chain.

In still another embodiment, the invention features a heavy chain comprising the complementarity determining regions (CDRs) and variable region framework residue H29, H30, H73, H91, H93, and H94 (Kabat numbering convention) from the monoclonal antibody 1A1 heavy chain, wherein the remainder of the heavy chain is from a human immunoglobulin. In another embodiment, the heavy chain of the invention further comprises at least one variable framework residue from the monoclonal antibody 1A1 heavy chain selected from the group consisting of H27, H28, H66, H69, and H76 (Kabat numbering convention).

In still another embodiment, the invention includes a light chain comprising the complementarity determining regions (CDRs) and variable framework residues L2 and L36 (Kabat numbering convention) from the monoclonal antibody 1A1 light chain, wherein the remainder of the light chain is from a human immunoglobulin. The invention also features a light chain further comprising the variable framework residue from the monoclonal antibody 1A1 heavy chain L45 (Kabat numbering convention).

In one embodiment, the invention features a humanized immunoglobulin comprising the heavy chain set forth in SEQ ID NO: 53. In still another embodiment, the invention includes a humanized immunoglobulin comprising the heavy chain set forth in SEQ ID NO: 54. In a further embodiment, the invention features a humanized immunoglobulin comprising the light chain set forth in SEQ ID NO: 55. The invention also features a humanized immunoglobulin comprising the light chain set forth in SEQ ID NO: 56. The invention also features a humanized immunoglobulin comprising a heavy chain comprising SEQ ID NO: 53 or SEQ ID NO: 54 and a light chain comprising SEQ ID NO: 55 or SEQ ID NO: 56.

In one embodiment, the invention features an immunoglobulin or antigen binding fragment, which specifically binds to MCP-1 with a binding affinity of at least $10^{-9}$ M. In another embodiment, the immunoglobulin or antigen binding fragment of the invention specifically binds to MCP-1 with a binding affinity of at least $10^{-10}$ M. In still a further embodiment, the immunoglobulin or antigen binding fragment of the invention specifically binds to MCP-1 with a binding affinity of at least $10^{-11}$ M. In one embodiment, the immunoglobulin or antigen-binding fragment of the invention binds to MCP-2. In another embodiment, the immunoglobulin or antigen-binding fragment of the invention binds to MCP-1 and MCP-2. In still another embodiment, the immunoglobulin or antigen-binding fragment of the invention binds to an epitope within CP-1, MCP-2, and MCP-3.

In still another embodiment, the invention features a method for identifying residues amenable to substitution in a humanized 1A1 immunoglobulin variable framework region, comprising modeling the three-dimensional structure of the 1A1 variable region based on a solved immunoglobulin structure and analyzing said model for residues capable of affecting 1A1 immunoglobulin variable region conformation or function, such that residues amenable to substitution are identified. The invention also includes use of the variable region sequence set forth as SEQ D NO: 11 or SEQ ID NO: 12, or any portion thereof, in producing a three-dimensional image of a 1A1 immunoglobulin, 1A1 immunoglobulin chain, or domain thereof.

In one embodiment, the immunoglobulin or antigen-binding fragment of the invention is modified by reducing or eliminating at least one potential glycosylation site. In another embodiment, the immunoglobulin or antigen-binding fragment of the invention is modified by conjugation to a carrier selected from polyethylene glycol and albumen. In yet another embodiment, the immunoglobulin or antigen-binding fragment of the invention is modified to reduce at least one constant region-mediated biological effector function relative to an unmodified antibody.

In one embodiment, the heavy chain isotype of the immunoglobulin or antigen-binding fragment of the invention is gamma 1.

In one embodiment, the fragment of the invention is a Fab fragment.

In one embodiment, the invention features an immunoglobulin or antigen-binding fragment which inhibits MCP-induced chemotaxis. In a certain embodiment, the immunoglobulin or antigen-binding fragment of the invention inhibits MCP-1-induced chemotaxis, MCP-2-induced chemotaxis, or both MCP-1-induced and MCP-2-induced chemotaxis.

In one embodiment, the immunoglobulin or antigen-binding fragment of the invention inhibits MCP-induced collagen expression. In another embodiment, the invention features an immunoglobulin or antigen-binding fragment, wherein the immunoglobulin or antigen-binding fragment inhibits MCP-1-induced collagen expression, MCP-2-induced collagen expression, or both MCP-1-induced and MCP-2-induced collagen expression.

In one embodiment, the invention features an immunoglobulin or antigen-binding fragment which inhibits MCP-1-induced angiogenesis. In certain embodiments, an immunoglobulin or antigen-binding fragment of the invention inhibits MCP-1-induced angiogenesis, MCP-2-induced angiogenesis, or both MCP-1-induced and MCP-2-induced angiogenesis.

In one embodiment, the immunoglobulin or antigen-binding fragment of any the invention reduces inflammation in a subject. In one embodiment, the inflammation is associated with a disorder selected from the group consisting of arthritis, multiple sclerosis, cirrhosis, atherosclerosis, and breast carcinoma.

In one embodiment, an immunoglobulin or antigen-binding fragment of the invention reduces fibrosis in a subject.

In one embodiment, the invention features a pharmaceutical composition comprising the immunoglobulin or antigen-binding fragment of the invention and a pharmaceutical carrier.

In another embodiment, the invention features a host cell comprising the nucleic acid molecule of a immunoglobulin or antigen-binding fragment of the invention. In one embodiment, the host cell of the invention is mammalian. In another embodiment, the host cell of the invention is bacterial. In still another embodiment, the invention describes a method of producing an antibody or antigen binding fragment thereof of the invention, comprising culturing the host cell under conditions such that the antibody or fragment is produced and isolating said antibody from the host cell or culture.

In still another embodiment, the invention provides a method of preventing or treating a disorder associated with detrimental MCP activity in a subject, comprising administering to the subject an effective amount of an immunoglobulin or antigen binding fragment of the invention. In one embodiment, the effective amount of immunoglobulin or antigen binding fragment thereof is 1-10 mg/kg body weight. In another embodiment, the disorder is selected from the group consisting of glomerulonephritis, scleroderma, cirrhosis, multiple sclerosis, lupus nephritis, atherosclerosis, inflammatory bowel diseases or rheumatoid arthritis.

In yet another embodiment, the invention provides a method of preventing or treating MCP-associated inflammation in a subject, comprising administering to the subject an effective amount of an immunoglobulin or antigen binding fragment of the invention.

In yet another embodiment of the invention, a method of preventing or treating MCP-associated inflammation in a subject is described, comprising administering to the subject an effective amount of the humanized immunoglobulin or antigen-binding portion of the invention. Effective amounts of humanized immunoglobulin or antigen-binding portion described in the invention include, for example, 1 mg/kg body weight to 10 mg/kg body weight.

In yet another embodiment, the invention provides a method of preventing or treating a fibrotic disorder in a subject comprising administering to the subject an effective amount of an immunoglobulin or antigen binding fragment of the invention.

In yet another embodiment, the invention provides a method of preventing or treating cancer in a subject comprising administering to the subject an effective amount of an immunoglobulin or antigen binding fragment of the invention.

In yet another embodiment, the invention provides a method of preventing or treating an immunopathologic disorder comprising administering to the subject an effective amount of an immunoglobulin or antigen binding fragment of the invention.

Another embodiment of the invention features use of the antibodies or antigen-binding fragments of the invention for preventing or treating an inflammatory disorder, e.g., Alzheimer's, severe asthma, atopic dermatitis, cachexia, CHF-ischemia, coronary restinosis, Crohn's disease, diabetic nephropathy, lymphoma, psoriasis, fibrosis/radiation-induced, juvenile arthritis, stroke, inflammation of the brain or central nervous system caused by trauma, and ulcerative colitis, inflammation due to corneal transplantation, chronic obstructive pulmonary disease, hepatitis C, multiple myeloma, and osteoarthritis.

Yet another embodiment of the invention features used of the antibodies or antigen-binding fragments of the invention for preventing or treating a neurodegenerative disorder. Neurodegenerative disorders which can be treated by the antibodies or antigen-binding fragments thereof, include, but are not limited to, Alzheimer's, stroke, traumatic brain or central nervous system injuries, ALS/motor neuron disease, diabetic peripheral neuropathy, diabetic retinopathy, Huntington's disease, macular degeneration, and Parkinson's disease.

In yet another embodiment, the invention includes a heavy chain of an anti-MCP antibody which contacts residues R30, T32, S34, K38, E39, V41, P55, K56, Q61, M64 of MCP-1. The invention further includes a light chain anti-MCP antibody which contacts residues D65, D68, K69 of MCP-1.

BRIEF DESCRIPTION OF DRAWINGS

FIG. 2 graphically depicts the results of a chemotaxis assay of cells in response to MCP-1.

FIG. 7 shows the amino acid and nucleotide sequences of the variable heavy region of the murine version of the 1A1 antibody (7A), as well as the amino acid and nucleotide sequences of the 1A1 variable light region (7B). CDR regions are underlined.

FIG. 8 shows the amino acid and nucleotide sequences of the murine 11K2 variable heavy region (FIG. 8A), and the amino acid and nucleotide sequences of murine 11K2 variable light region (FIG. 8B). CDR regions are underlined.

FIG. 9 shows the nucleotide and amino acid sequences of a heavy chain chimera (variable and constant regions) of the 11K2 antibody (9A). The variable region is set forth at nucleotides 1-351 (amino acids 1-117) of the heavy chain. FIG. 9B shows the DNA/amino acid comparison of the 11K2 light chain chimera (variable and constant regions). The variable region is set forth at nucleotides 1-321 (amino acids 1-107) of the light chain. All CDRs are underlined.

FIG. 10 shows the nucleotide and amino acid sequences of the light and heavy chains of humanized 11K2 antibody. FIG. 10A shows the sequence of humanized version 1 including heavy chain variable and constant regions. FIG. 10B shows the sequence of humanized version 2 including heavy chain variable and constant regions. FIG. 10C shows the sequence of humanized version 1 light chain variable and constant regions. FIG. 10D shows the sequence of humanized version 2 light chain variable and constant regions. All CDR regions are underlined, and all backmutations are highlighted in bold.

FIG. 11 shows an alignment of the murine 11K2 antibody and the humanized 11K2 (versions 1 and 2) for the variable heavy chain region (A) and the variable light chain region (B). All CDRs are underlined and in bold.

FIG. 12 graphically depicts results from a neutralization assay using mAb 11K2, chimeric 11K2, aglycosylated chimeric 11K2, H1/L1 humanized 11K2, H2/L2 humanized 11K2, H1/L2 humanized 11K2, and H2/L1 humanized 11K2 antibodies (whole and Fab fragments).

FIG. 15 graphically depicts the therapeutic effect of mouse monoclonal antibody 11K2 treatment on survival of mice afflicted by TNBS-induced colitis.

FIG. 19 graphically depicts results demonstrating a reduction in atherosclerotic plaque size (total plaque area) in apoE-deficient mice treated with mouse monoclonal antibody 11K2.

DETAILED DESCRIPTION OF THE INVENTION

Figure 1:
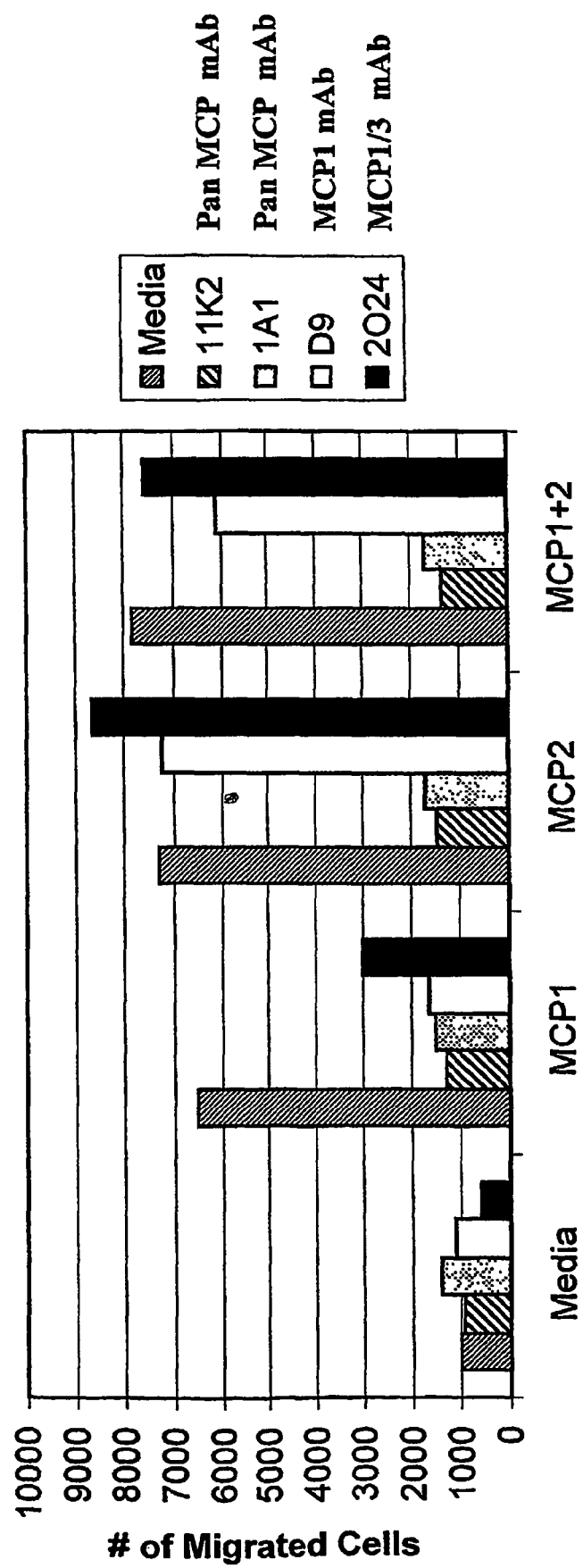
FIG. 1 graphically depicts results of a chemotaxis assay using purified 11K2, 1A1, D9, and 2O24 to inhibit chemotaxis in response to MCP-1, MCP-2, and a combination of MCP-1/MCP-2. The results show that chemotaxis to a combination of MCP-1 and MCP-2 is inhibited by 11K2 and 1A1.

The present invention features new immunological reagents and methods for preventing or treating disorders associated with detrimental MCP activity. The invention is based, at least in part, on the characterization of two monoclonal immunoglobulins, 11K2 and 1A1, effective at binding MCPs (Aβ) (e.g., MCP-1, MCP-2, and MCP-3). The invention is further based on the determination and structural characterization of the primary and secondary structure of the variable light and heavy chains of these immunoglobulins and the identification of residues important for activity and immunogenicity.

Immunoglobulins are featured which include a variable light and/or variable heavy chain of the preferred monoclonal immunoglobulins described herein. Preferred immunoglobulins, e.g., therapeutic immunoglobulins, are featured which include a humanized variable light and/or humanized variable heavy chain. Preferred variable light and/or variable heavy chains include a complementarity determining region (CDR) from the monoclonal immunoglobulin (e.g., donor immunoglobulin) and variable framework regions substantially from a human acceptor immunoglobulin. The phrase "substantially from a human acceptor immunoglobulin" means that the majority or key framework residues are from the human acceptor sequence, allowing however, for substitution of residues at certain positions with residues selected to improve activity of the humanized immunoglobulin (e.g., alter activity such that it more closely mimics the activity of the donor immunoglobulin) or selected to decrease the immunogenicity of the humanized immunoglobulin.

In one embodiment, the invention features a humanized immunoglobulin light or heavy chain that includes 11K2 variable region complementarity determining regions (CDRs) (i.e., includes one, two or three CDRs from the light chain variable region sequence set forth as SEQ ID NO: 28 or includes one, two or three CDRs from the heavy chain variable region sequence set forth as SEQ ID NO: 27), and includes a variable framework region substantially from a human acceptor immunoglobulin light or heavy chain sequence, provided that at least one residue of the framework residue is backmutated to a corresponding murine residue, wherein said backmutation does not substantially affect the ability of the chain to direct MCP binding.

In another embodiment, the invention features a humanized immunoglobulin light or heavy chain that includes 11K2 variable region complementarity determining regions (CDRs) (e.g., includes one, two or three CDRs from the light chain variable region sequence set forth as SEQ ID NO: 28 and/or includes one, two or three CDRs from the heavy chain variable region sequence set forth as SEQ ID NO: 27), and includes a variable framework region substantially from a human acceptor immunoglobulin light or heavy chain sequence, provided that at least one framework residue is substituted with the corresponding amino acid residue from the mouse 11K2 light or heavy chain variable region sequence, where the framework residue is selected from the group consisting of (a) a residue that non-covalently binds antigen directly, (b) a residue adjacent to a CDR; (c) a CDR-interacting residue (e.g., identified by modeling the light or heavy chain on the solved structure of a homologous known immunoglobulin chain); and (d) a residue participating in the VL-VH interface.

In another embodiment, the invention features a humanized immunoglobulin light or heavy chain that includes 11K2 variable region CDRs and variable framework regions from a human acceptor immunoglobulin light or heavy chain sequence, provided that at least one framework residue is substituted with the corresponding amino acid residue from the mouse 11K2 light or heavy chain variable region sequence, where the framework residue is a residue capable of affecting light chain variable region conformation or function as identified by analysis of a three-dimensional model of the variable region, for example a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, or an unusual residue.

In another embodiment, the invention features a humanized immunoglobulin light chain that includes 11K2 variable region CDRs (e.g., from the 11K2 light chain variable region sequence set forth as SEQ ID NO: 28), and includes a human acceptor immunoglobulin variable framework region, provided that at least one framework residue selected from the group consisting of L49, L69 and L71 (Kabat numbering convention) is substituted with the corresponding amino acid residue from the mouse 11K21 light chain variable region sequence. In another embodiment, the invention features a humanized immunoglobulin heavy chain that includes 11K2 variable region CDRs (e.g., from the 11K2 heavy chain variable region sequence set forth as SEQ ID NO: 27), and includes a human acceptor immunoglobulin variable framework region, provided that at least one framework residue selected from the group consisting of H27, H28, H29, H30, H48, H67, and H73 (Kabat numbering convention) is substituted with the corresponding amino acid residue from the mouse 11K2 heavy chain variable region sequence.

Preferred light chains include framework regions of the subtype kappa 1 (Kabat convention), for example, framework regions from the acceptor immunoglobulin GI-486875. Preferred heavy chains include framework regions of the subtype 1 (Kabat convention), for example, framework regions from the acceptor immunoglobulin Kabat ID 000054.

In one embodiment, the invention features a humanized immunoglobulin light or heavy chain that includes 1A1 variable region complementarity determining regions (CDRs) (i.e., includes one, two or three CDRs from the light chain variable region sequence set forth as SEQ ID NO: 12 or includes one, two or three CDRs from the heavy chain variable region sequence set forth as SEQ ID NO: 11), and includes a variable framework region substantially from a human acceptor immunoglobulin light or heavy chain sequence, provided that at least one residue of the framework residue is backmutated to a corresponding murine residue, wherein said backmutation does not substantially affect the ability of the chain to direct MCP binding.

In another embodiment, the invention features a humanized immunoglobulin light or heavy chain that includes 1A1 variable region complementarity determining regions (CDRs) (e.g., includes one, two or three CDRs from the light chain variable region sequence set forth as SEQ ID NO: 12 and/or includes one, two or three CDRs from the heavy chain variable region sequence set forth as SEQ ID NO: 11), and includes a variable framework region substantially from a human acceptor immunoglobulin light or heavy chain sequence, provided that at least one framework residue is substituted with the corresponding amino acid residue from the mouse 1A1 light or heavy chain variable region sequence, where the framework residue is selected from the group consisting of (a) a residue that non-covalently binds antigen directly; (b) a residue adjacent to a CDR; (c) a CDR-interacting residue (e.g., identified by modeling the light or heavy chain on the solved structure of a homologous known immunoglobulin chain); and (d) a residue participating in the VL-VH interface.

In another embodiment, the invention features a humanized immunoglobulin light or heavy chain that includes 1A1 variable region CDRs and variable framework regions from a human acceptor immunoglobulin light or heavy chain sequence, provided that at least one framework residue is substituted with the corresponding amino acid residue from the mouse 1A1 light or heavy chain variable region sequence, where the framework residue is a residue capable of affecting light chain variable region conformation or function as identified by analysis of a three-dimensional model of the variable region, for example a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, or an unusual residue.

In another embodiment, the invention features a humanized immunoglobulin that includes a light chain and a heavy chain, as described above, or an antigen-binding fragment of said immunoglobulin. In an exemplary embodiment, the humanized immunoglobulin binds (e.g., specifically binds) to MCP-1 with a binding affinity of at least $10^7 M^{-1}$, $10^8 M^{-1}$, or $10^9 M^{-1}$.

In another embodiment, the invention features chimeric immunoglobulins that include 11K2 variable regions (e.g., the variable region sequences set forth as SEQ ID NO: 27 or SEQ ID NO: 28). In yet another embodiment, the invention features an immunoglobulin, or antigen-binding fragment thereof, including a variable heavy chain region as set forth in SEQ ID NO: 47 or SEQ ID NO: 48 and a variable light chain region as set forth in SEQ ID NO: 49 or SEQ ID NO: 50.

In another embodiment, the invention features chimeric immunoglobulins that include 1A1 variable regions (e.g., the variable region sequences set forth as SEQ ID NO: 11 or SEQ ID NO: 12). In yet another embodiment, the invention features an immunoglobulin, or antigen-binding fragment thereof, including a variable heavy chain region as set forth in SEQ ID NO: 53 or SEQ ID NO: 54 and a variable light chain region as set forth in SEQ ID NO: 55 or SEQ ID NO: 56. In yet another embodiment, the immunoglobulin, or antigen-binding fragment thereof, further includes constant regions from IgG1.

The immunoglobulins described herein are particularly suited for use in therapeutic methods aimed at preventing or treating disorders associated with detrimental MCP activity. In one embodiment, the invention features a method of preventing or treating a disorder associated with detrimental MCP activity that involves administering to the subject an effective dosage of a humanized immunoglobulin as described herein. In another embodiment, the invention features pharmaceutical compositions that include a humanized immunoglobulin as described herein and a pharmaceutical carrier. Also featured are isolated nucleic acid molecules, vectors and host cells for producing the immunoglobulins or immunoglobulin fragments or chains described herein, as well as methods for producing said immunoglobulins, immunoglobulin fragments or immunoglobulin chains The present invention further features a method for identifying 1A1 or 11K2 residues amenable to substitution when producing a humanized 1A1 or 11K2 immunoglobulin, respectively. For example, a method for identifying variable framework region residues amenable to substitution involves modeling the three-dimensional structure of the 1A1 or 11K2 variable region on a solved homologous immunoglobulin structure and analyzing said model for residues capable of affecting 1A1 or 11K2 immunoglobulin variable region conformation or function, such that residues amenable to substitution are identified. The invention further features use of the variable region sequence set forth as SEQ ID NO: 27 or SEQ ID NO: 28, or any portion thereof, in producing a three-dimensional image of a 11K2 immunoglobulin, 11K2 immunoglobulin chain, or domain thereof. Also featured is the use of the variable region sequence set forth as SEQ ID NO: 11 or SEQ ID NO: 12, or any portion thereof, in producing a three-dimensional image of a 1A1 immunoglobulin, 1A1 immunoglobulin chain, or domain thereof.

Prior to describing the invention, it may be helpful to an understanding thereof to set forth definitions of certain terms to be used hereinafter.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "domain" refers to a globular region of a heavy or light chain polypeptide comprising peptide loops (e.g. comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). "Variable" domains on the light chain are referred to interchangeably as "light chain variable regions", "light chain variable domains", "VL" regions or "VL" domains). "Variable" domains on the heavy chain are referred to interchangeably as "heavy chain constant regions", "heavy chain constant domains", "CH" regions or "CH" domains).

The term "region" refers to a part or portion of an antibody chain and includes constant or variable domains as defined herein, as well as more discrete parts or portions of said domains. For example, light chain variable domains or regions include "complementarity determining regions" or "CDRs" interspersed among "framework regions" or "FRs", as defined herein.

Immunoglobulins or antibodies can exist in monomeric or polymeric form. The term "antigen-binding fragment" refers to a polypeptide fragment of an immunoglobulin or antibody binds antigen or competes with intact antibody (i.e., with the intact antibody from which they were derived) for antigen binding (i.e., specific binding). The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

"Specific binding" of an antibody mean that the antibody exhibits appreciable affinity for antigen or a preferred epitope and, preferably, does not exhibit significant crossreactivity. "Appreciable" or preferred binding include binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{13}$ $M^{-1}$, preferably $10^7$ to $10^{13}$ $M^{-1}$, more preferably $10^8$ to $10^{13}$ $M^{-1}$. An antibody that "does not exhibit significant crossreactivity" is one that will not appreciably bind to an undesirable entity (e.g., an undesirable proteinaceous entity). An antibody specific for a preferred epitope will, for example, not significantly crossreact with remote epitopes on the same protein or peptide. Specific binding can be determined according to any art-recognized means for determining such binding. Preferably, specific binding is determined according to Scatchard analysis and/or competitive binding assays.

In one embodiment, the invention provides for antibodies, antigen-binding fragments and/or antibody fragments of the invention that have high binding affinity for b-chemokines. High binding affinity refers to binding affinities of, for example, about $10\times10^{-12}$ M (i.e. 10 pM) or less. In one embodiment the immunoglobulins or antigen-binding fragments have a Kd for binding to the b-chemokines (either binding a plurality of MCPs selected from MCP-1, MCP-2, and MCP-3 or that bind the individual MCPs, i.e. an antibody or antigen-binding fragment that binds to MCP-1, MCP-2 or MCP-3) between about $10\times10^{-12}$ M (10 pM) and about $8\times10^{-12}$ M (8 pM) including $9\times10^{-1}$ M (9 pM); alternatively between about $9\times10^{-12}$ M (9 pM) and about $7\times10^{-12}$ M (7 pM) including $8\times10^{-12}$ M (8 pM); alternatively between about $8\times10^{-12}$ M (8 pM) and about $6\times10^{-12}$ M (6 pM) including $7\times10^{-12}$ M (7 pM); alternatively between about $7\times10^{-12}$ M (7 pM) and about $5\times10^{-12}$ M (5 pM) including $6\times10^{-12}$ M (6 pM), alternatively between about $6\times10^{-12}$ M (6 pM) and about $4\times10^{-12}$ M (4 pM) including $5\times10^{-12}$ M (5 pM), alternatively between about $5\times10^{-12}$ M (5 pM) and about $3\times10^{-12}$ M (3 pM) including $4\times10^{-12}$ M (4 pM); alternatively between about $4\times10^{-12}$ M (4 pM) and about $2\times10^{-12}$ M (2 pM) including $3\times10^{-12}$ M (3 pM); alternatively between about $3\times10^{-12}$ M (3 pM) and about $1\times10^{-12}$ M (1 pM) including $2\times10^{-12}$ M (2 pM); alternatively about $1\times10^{-12}$ M (1 pM) and about $8\times10^{-13}$ M (0.8 pM) including $9\times10^{-13}$ M (0.9 pM); alternatively between about $9\times10^{-13}$ M (0.9 pM) and about $7\times10^{-13}$ M (0.7 pM) including $8\times10^{-13}$ M (0.8 pM); alternatively between about $8\times10^{-13}$ M (0.8 pM) and about $6\times10^{-13}$ M (0.6 pM) including $7\times10^{-13}$ M (0.7 pM); alternatively between about $7\times10^{-13}$ M (0.7 pM) and about $5\times10^{-13}$ M (0.5 pM) including $6\times10^{-13}$ M (0.6 pM), alternatively between about $6\times10^{-13}$ M (0.6 pM) and about $4\times10^{-13}$ M (0.4 pM) including $5\times10^{-13}$ M (0.5 pM), alternatively between about $5\times10^{-13}$ M (0.5 pM) and about $3\times10^{-13}$ M (0.3 pM) including $4\times10^{-13}$ M (0.4 pM); alternatively between about $4\times10^{-13}$ M (0.4 pM) and about $2\times10^{-13}$ M (0.2 pM) including $3\times10^{-13}$ M (0.3 pM); alternatively between about $3\times10^{-13}$ M (0.3 pM) and about $1\times10^{-13}$ M (0.1 pM) including $2\times10^{-13}$ M (0.2 pM). The invention would include for example an antibody or antigen-binding fragment thereof that binds to MCP-1, MCP-2 or MCP-3 wherein the antibody or antigen-binding fragment thereof has a Kd for binding to MCP-1, MCP-2 or MCP-3 selected from the following Kd's: about $10\times10^{-13}$ M (1 pM), $9\times10^{-13}$ M (0.9 pM), $8\times10^{-13}$ M (0.8 pM), $7\times10^{-13}$ M (0.7 pM), $6\times10^{-13}$ M (0.6 pM), $5\times10^{-13}$ M (0.5 pM), $4\times10^{-13}$ M (0.4 pM), $3\times10^{-13}$ M (0.3 pM), $2\times10^{-13}$ M (0.2 pM) or $1\times10^{-13}$ M (0.1 pM). (An example of such an antibody would include for example 11K2 in which the antibody has a binding affinity for human MCP-1 of about 0.4 pM.) The invention would also include for example an antibody or antigen-binding fragment thereof that binds to a plurality of MCP's (i.e.

MCP-1 and MCP-2 or MCP-1 and MCP-3 or MCP-1, MCP-2 and MCP-3 or MCP-2 and MCP-3) wherein the antibody or antigen-binding fragment thereof has a Kd for binding to at least one of the MCP's (i.e. MCP-1, MCP-2 or MCP-3) selected from the following Kd's: about $10 \times 10^{-13}$ M (1 PM), $9 \times 10^{-13}$ M (0.9 pM), $8 \times 10^{-13}$ M (0.8 pM), $7 \times 10^{-13}$ M (0.7 pM), $6 \times 10^{-13}$ M (0.6 pM), $5 \times 10^{-13}$ M (0.5 pM), $4 \times 10^{-13}$ M (0.4 pM), $3 \times 10^{-13}$ M (0.3 pM), $2 \times 10^{-13}$ M (0.2 pM) or $1 \times 10^{-13}$ M (0.1 pM). (An example of such an antibody would also include for example 11K2 in which the antibody has a binding affinity for human MCP-1 of about 0.4 pM. and also binds MCP-2 and MCP-3). Methods for measuring the binding affinity of the antibody, antigen-binding fragment and or antibody fragment for the various b-chemokine(s) are known to those of skill in the art and include, for example, the kinetic exclusion assay illustrated in the Examples as well.

The invention also provides for immunoglobulins and antigen-binding fragments comprising a Fab fragment wherein the Fab fragment has a Kd for binding MCP-1, MCP-2 or MCP-3 of, for example, about $1.5 \times 10^{-11}$ M (i.e. 15 pM) or less. The invention would include for example an antibody, antigen-binding fragment and/or antibody fragment thereof wherein the Fab fragment has a Kd for binding to MCP-1, MCP-2 or MCP-3 selected from the following Kd's: about $1.8 \times 10^{-11}$ M (18 pM), about $1.7 \times 10^{-11}$ M (17 pM), about $1.6 \times 10^{-11}$ M (15 pM), about $1.5 \times 10^{-11}$ M (15 pM), $1.4 \times 10^{11}$ M (14 pM), $1.3 \times 10^{-11}$ M (13 pM), $1.2 \times 10^{-11}$ M (12 pM), $1.1 \times 10^{-11}$ M (11 pM), $1 \times 10^{-11}$ M (10 pM), $0.9 \times 10^{-11}$ M (9 pM), $0.8 \times 10^{-11}$ M (8 pM), $0.7 \times 10^{-11}$ M (7 pM), $0.6 \times 10^{-11}$ M (6 pM), $0.5 \times 10^{-11}$ M (5 pM), $0.4 \times 10^{-11}$ M (4 pM), $0.3 \times 10^{-11}$ M (3 pM), $0.2 \times 10^{-11}$ M (2 pM) or $0.1 \times 10^{-11}$ M (1 pM). Methods for measuring the binding affinity of the antibody, antigen-binding fragment and or antibody fragment are known to those of skill in the art and include, for example, the kinetic exclusion assay illustrated in Example 4 herewith.

The invention also provides for immunoglobulins and antigen-binding fragments that have the following binding affinity for the b-chemokines (either binding a plurality of MCP's selected from MCP-1, MCP-2, and MCP-3 or that bind the individual MCPs, i.e. an antibody or antigen-binding fragment that binds to MCP-1, MCP-2 or MCP-3). In one embodiment the binding affinity is between about $5 \times 10^{-8}$ M and about $5 \times 10^{-12}$ M, in some embodiments the binding affinity is about $5 \times 10^{-9}$ M to about $5 \times 10^{-11}$ M, in some embodiments the binding affinity is about $5 \times 10^{-7}$ M to about $5 \times 10^{-8}$ M, in some embodiments the binding affinity is about $5 \times 10^{-8}$ M to about $5 \times 10^{-9}$ M, in some embodiments the binding affinity is about $5 \times 10^{-9}$ M to about $5 \times 10^{-10}$ M, in some embodiments the binding affinity is about $5 \times 10^{-10}$ M to about $5 \times 10^{-11}$ M.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g. at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino acid sequence for comparison purposes, the region shares at least 80-90%, preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "significant identity" means that two polypeptide sequences, when optimally aligned, such as by the programs GAP or BESTFIT using default gap weights, share at least 50-60% sequence identity, preferably 60-70% sequence identity, more preferably 70-80% sequence identity, more preferably at least 80-90% identity, even more preferably at least 90-95% identity, and even more preferably at least 95% sequence identity or more (e.g., 99% sequence identity or more). The term "substantial identity" means that two polypeptide sequences, when optimally aligned, such as by the programs GAP or BESTFIT using default gap weights, share at least 80-90% sequence identity, preferably 90-95% sequence identity, and more preferably at least 95% sequence identity or more (e.g., 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. The terms "sequence identity" and "sequence identity" are used interchangeably herein.

Optimal alignment of sequences for comparison can be conducted, e.g. by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al, *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Preferably, humanized immunoglobulins or antibodies bind antigen with an affinity that is within a factor of three, four, or five of that of the corresponding non-human antibody. For example, if the nonhuman antibody has a binding affinity of $10^9$ $M^{-1}$, humanized antibodies will have a binding affinity of at least $3\times10^9$ $M^{-1}$, $4\times10^9$ $M^{-1}$ or $10^9$ $M^{-1}$. When describing the binding properties of an immunoglobulin or antibody chain, the chain can be described based on its ability to "direct antigen (e.g, MCP-1) binding". A chain is said to "direct antigen binding" when it confers upon an intact immunoglobulin or antibody (or antigen binding fragment thereof) a specific binding property or binding affinity. A mutation (e.g., a backmutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose light and heavy chains are derived from different species. Chimeric immunoglobulins or antibodies can be constructed, for example by genetic engineering, from immunoglobulin gene segments belonging to different species.

An "antigen" is an entity (e.g., a proteinaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as MCP-1. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Exemplary epitopes or antigenic determinants can be found within human MCP molecules, and are preferably within MCP-1, MCP-2, and MCP-3. Other preferred epitopes are those that are commonly found within MCP-1 and MCP-2, MCP-1 and MCP-3, MCP-1 and MCP-3, and MCP-1, MCP-2 and MCP-3.

As used herein, the term "b-chemokine" refers to a polypeptide containing four conserved cysteine residues characteristic of b-chemokines (e.g. as described in inflammation (Van Coillie et al. (1999) *Cytokine & Growth Factor Rev.* 10:61-86) wherein the first two conserved cysteines are adjacent.

As used herein, the term "inhibiting the activity of b-chemokines" refers to causing a decrease in the relative activity of b-chemokines in the presence of the antibody or antigen-binding fragment thereof in comparison with the activity observed in the absence of the antibody or antigen-binding fragment thereof. The term "inhibits MCP activity" is defined herein as reducing or eliminating activity associated with MCPs, e.g. MCP-1, MCP-2, or MCP-3, for example by reducing or inhibiting MCP-induced chemotaxis and/or by reducing or inhibiting MCP-induced collagen expression and/or by reducing or inhibiting MCP-induced angiogenesis. Activities associated with MCP-induction can be assayed according to standard methods known in the art, and as described herein.

As used herein, the term "sign of an inflammatory disorder" refers to observable or measurable indications of pathological inflammation, including, but not limited to edema, fever, emigration of leukocytes, proliferation of blood vessels, proliferation of connective tissue, redness, localized heat, exudation, and other signs as described in ROBBINS PATHOLOGIC BASIS OF DISEASE, 4$^{TH}$ EDITION, R. S. Cotran et al., Eds. W.B. Saunders, Co., 1989.

As used herein, the term "blocking chemotaxis" refers to a decrease in the relative amount of chemotactic activity of cells in the presence of the antibody or antigen-binding fragment thereof in comparison with chemotactic activity observed in the absence of the antibody or antigen-binding fragment thereof.

As used herein, the term "MCP MRHAS Motif" refers to an amino acid motif in human MCP-1 and MCP-3 termed Meningitis Related Homologous Antigenic Sequence. For human MCP-1, the MRHAS amino acid motif is Gln-Thr-Gln-Thr-Pro-Lys-Thr (SEQ ID NO:1); and for human MCP-3, the MRHAS motif is Lys-Thr-Gln-Thr-Pro-Lys-Leu (SEQ ID NO:2).

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a subject already suffering from the disease. Amounts effective for this use will depend upon the severity of the infection and the general state of the subject's own immune system.

The term "subject" includes human and other mammalian subjects that receive either prophylactic or therapeutic treatment.

I. Immunological and Therapeutic Reagents

Immunological and therapeutic reagents of the invention comprise or consist of immunogens or antibodies, or functional or antigen binding fragments thereof, as defined herein. The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda and are about 230 residues in length. Heavy chains are classified as gamma (γ), mu (μ), alpha (α), delta (δ), or epsilon (ε), are about 450-600 residues in length, and define the antibody's isotype as IgG, IgM, IgA, IgD and IgE, respectively. Both heavy and light chains are folded into domains. The term "domain" refers to a globular region of a protein, for example, an immunoglobulin or antibody. Immunoglobulin or antibody domains include, for example, 3 or four peptide loops stabilized by β-pleated sheet and an interchain disulfide bond. Intact light chains have, for example, two domains ($V_L$ and $C_L$) and intact heavy chains have, for example, four or five domains ($V_H$, $C_H1$, $C_H2$, and $C_H3$).

Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y. (1989), Ch. 7, incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. Naturally-occurring chains or recombinantly produced chains can be expressed with a leader sequence which is removed during cellular processing to produce a mature chain. Mature chains can also be recombinantly produced having a non-naturally occurring leader sequence, for example, to enhance secretion or alter the processing of a particular chain of interest.

The CDRs of the two mature chains of each pair are aligned by the framework regions, enabling binding to a specific epitope. From N-terminal to C-terminal, both light and heavy chains comprise the domains FR1, CDR1, FR2, CDR2, FR3, CDR3 and FR4. "FR4" also is referred to in the art as the D/J region of the variable heavy chain and the J region of the variable light chain. The assignment of amino acids to each domain is in accordance with the definitions of Kabat, *Sequences of Proteins of Immunological Interest* (National Institutes of Health, Bethesda, Md., 1987 and 1991). An alternative structural definition has been proposed by Chothia et al., *J. Mol. Biol.* 196:901 (1987); *Nature* 342:878 (1989); and *J. Mol. Biol.* 186:651 (1989) (hereinafter collectively referred to as "Chothia et al." and incorporated by reference in their entirety for all purposes).

A. MCP Antibodies

Therapeutic agents of the invention include antibodies that specifically bind to MCPs or other b-chemokines. Such antibodies can be monoclonal or polyclonal. Some such antibodies bind specifically MCP-1. Some bind specifically to MCP-2. Some bind to both MCP-1 and MCP-2. Some such antibodies bind to MCP-3. Antibodies used in therapeutic methods preferably have an intact constant region or at least sufficient of the constant region to interact with an Fc receptor. Human isotype IgG1 is preferred because of it having highest affinity of human isotypes for the FcRI receptor on phagocytic cells. Bispecific Fab fragments can also be used, in which one arm of the antibody has specificity for MCP-1, MCP-2, MCP-3, or a combination thereof, and the other for an Fc receptor. Preferred antibodies bind to MCP-1 with a binding affinity greater than (or equal to) about $10^6$, $10^7$, $10^8$, $10^9$, $10^{10}$, $10^{11}$, $10^{12}$, or $10^{13}$ $M^{-1}$ (including affinities intermediate of these values).

In certain embodiments the antibodies of the invention, and fragments thereof bind to regions in the b-chemokines (e.g., MCP-1, MCP-2 and MCP-3). In some embodiments, the antibodies or antigen-binding fragments thereof bind MCP-2 and at least one other b-chemokine (e.g., MCP-1 or MCP-3). Thus in some embodiments, the antibodies or fragments thereof bind MCP-1 and MCP-2 and in other embodiments the antibodies or fragments thereof bind MCP2 and MCP-3. In other embodiments, the antibodies or antigen-binding fragments thereof bind MCP-1, MCP-2 and MCP-3. In other embodiments, the antibodies or antigen-binding fragments thereof bind MCP-1 and MCP-3 other than to regions containing the MRHAS motifs, QTQTPKT (MCP-1) and KTQTPKL (MCP-3).

In certain embodiments, the antibodies or antigen-binding fragments thereof comprise antibodies selected from the group consisting of 11K2.1 (ATCC Accession No. PTA-3987), 6D21.1 (ATCC Accession No. PTA-3989), 4N4.1 (ATCC Accession No. PTA-3994), 5A13.1 (ATCC Accession No. PTA-3995), 7H1.1 (ATCC Accession No. PTA-3985), 1A1.1 (ATCC Accession No. PTA-3990), 6I5.1 (ATCC Accession No. PTA-3986), 2O24.1 (ATCC Accession No. PTA-3993), 9B11.1 (ATCC Accession No. PTA-3992), 9B12.1 (ATCC Accession No. PTA-3996), 9C11.1 (ATCC Accession No. PTA-3988), and 12F15.1 (ATCC Accession No. PTA-3991), or antigen-binding fragments of these antibodies.

Polyclonal sera typically contain mixed populations of antibodies binding to several epitopes, including, for example, MCP-1. Monoclonal antibodies bind to a specific epitope within b-chemokines, e.g., MCP-1, that can be a conformational or nonconformational epitope. Preferred monoclonal antibodies bind to an epitope within MCP-1 or MCP-2. Some preferred monoclonal antibodies bind to an epitope within MCP-1 and MCP-2, and some to an epitope within MCP-1, MCP-2, and MCP-3. It is recommended that such antibodies be screened for activity in the mouse models before use.

When an antibody is said to bind to an epitope within specified residues of a certain b-chemokine, such as MCP-1 for example, what is meant is that the antibody specifically binds to a polypeptide containing the specified residues. Such an antibody does not necessarily contact every residue, nor does every single amino acid substitution or deletion with the specified necessarily significantly affect binding affinity. Epitope specificity of an antibody can be determined, for example, by forming a phage display library in which different members display different subsequences of MCPs. The phage display library is then selected for members specifically binding to an antibody under test. A family of sequences is isolated. Typically, such a family contains a common core sequence, and varying lengths of flanking sequences in different members. The shortest core sequence showing specific binding to the antibody defines the epitope bound by the antibody. Antibodies can also be tested for epitope specificity in a competition assay with an antibody whose epitope specificity has already been determined. For example, antibodies that compete with the 11K2 antibody for binding to MCP-1 bind to the same or similar epitope as 11K2. Likewise antibodies that compete with the 1A1 antibody bind to the same or similar epitope. Screening antibodies for epitope specificity is a useful predictor of therapeutic efficacy. In one embodiment, the invention includes an anti-MCP antibody with a heavy chain which contacts residues R30, T32, S34, K38, E39, V41, P55, K56, Q61, M64 of MCP-1. The invention also includes a an anti-MCP antibody with a light chain which contacts residues D65, D68, K69 of MCP-1.

1. Production of Nonhuman Antibodies

The present invention features non-human antibodies, for example, antibodies having specificity for the preferred MCP epitopes of the invention. Such antibodies can be used in formulating various therapeutic compositions of the invention or, preferably, provide complementarity determining regions for the production of humanized or chimeric antibodies (described in detail below). The production of non-human monoclonal antibodies, e.g., murine, guinea pig, primate, rabbit or rat, can be accomplished by, for example, immunizing the animal with at least one b-chemokine. In producing the antibodies of the invention, the immunogens may be a preparation containing at least one b-chemokine, preferably more than one b-chemokine. In some embodiments, the b-chemokines are human monocyte chemotactic proteins (MCPs), including MCP-1, MCP-2 and MCP-3. The b-chemokines may be native or recombinantly produced b-chemokines. In some embodiments, the immunogens may be antigenic fragments of b-chemokines, such as fragments of MCPs which may optionally be conjugated to a carrier molecule to impart a stronger immune response upon administration to an animal. The b-chemokine immunogens, such as MCPs may contain additions, deletions and/or substitutions of amino acids, provided that the alterations do not ablate antigenicity of the mutated b-chemokines such that antibodies against the mutant versions do not bind native b-chemokines. Preferably, the amino acid substitutions are conservative changes in the amino acid sequence, provided the MCP molecules remain antigenic. See Harlow & Lane, supra, incorporated by reference for all purposes).

Such an immunogen can be obtained from a natural source, by peptide synthesis or by recombinant expression. Optionally, the immunogen can be administered fused or otherwise complexed with a carrier protein, as described below. Optionally, the immunogen can be administered with an adjuvant. The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages. Several types of adjuvant can be used as described below. Complete Freund's adjuvant followed by incomplete adjuvant is preferred for immunization of laboratory animals.

Rabbits or guinea pigs are typically used for making polyclonal antibodies. Exemplary preparation of polyclonal antibodies, e.g., for passive protection, can be performed as follows. 125 non-transgenic mice are immunized with 100 μg of a MCP-1/MCP-2 cocktail, plus CFA/IFA adjuvant, and euthanized at 4-5 months. Blood is collected from immunized mice. IgG is separated from other blood components. Antibody specific for the immunogen may be partially purified by affinity chromatography. An average of about 0.5-1 mg of immunogen-specific antibody is obtained per mouse, giving a total of 60-120 mg.

Mice are typically used for making monoclonal antibodies. Monoclonals can be prepared against a fragment by injecting, for example, a fragment of MCP-1 into a mouse, preparing hybridomas and screening the hybridomas for an antibody that specifically binds to MCP-1. Optionally, antibodies are screened for binding to a specific region or desired fragment of MCP-1 without binding to other nonoverlapping fragments of MCP-1. The latter screening can be accomplished by determining binding of an antibody to a collection of deletion mutants of a MCP-1 peptide and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to MCP-1. If the test and reference antibodies compete, then they bind to the same epitope or epitopes sufficiently proximal such that binding of one antibody interferes with binding of the other. The preferred isotype for such antibodies is mouse isotype IgG2a or equivalent isotype in other species. Mouse isotype IgG2a is the equivalent of human isotype IgG1.

2. Chimeric and Humanized Antibodies

The present invention also features chimeric and/or humanized antibodies (i.e., chimeric and/or humanized immunoglobulins) specific for b-chemokines, including MCPs. Chimeric and/or humanized antibodies have the same or similar binding specificity and affinity as a mouse or other nonhuman antibody that provides the starting material for construction of a chimeric or humanized antibody.

in one embodiment, the CDRs of the 11K2 antibody can be used to produce humanized and chimeric antibodies. The invention features an isolated antibody, or antigen binding portion thereof, which binds a plurality of b-chemokines, wherein said b-chemokines comprise MCP-2 and at least one other b-chemokine, which comprises at least one of the following CDRs: CDR1, CDR2, or CDR3, from the 11K2 heavy chain variable region described in SEQ ID NO: 27. In an additional embodiment, the invention features an isolated antibody, or antigen binding portion thereof, which binds a plurality of b-chemokines, wherein said b-chemokines comprise MCP-2 and at least one other b-chemokine, which comprises at least one of the following CDR combinations: CDR1 and CDR2; CDR1 and CDR3; CDR2 and CDR3; or CDR1, CDR2, and CDR3, from the 11K2 heavy chain variable region described in SEQ ID NO: 27. In one embodiment, the antibody of the invention is a chimeric antibody. In another embodiment, the antibody of the invention is a humanized antibody.

The CDRs of the 1A1 antibody can be also used to produce humanized and chimeric antibodies. In one embodiment, the invention provides an isolated antibody, or antigen binding portion thereof, which binds a plurality of b-chemokines, wherein said b-chemokines comprise MCP-2 and at least one other b-chemokine, which comprises at least one of the following CDRs: CDR1, CDR2, or CDR3, from the 1A1 heavy chain variable region described in SEQ ID NO: 11. In another embodiment, the invention provides an isolated antibody, or antigen binding portion thereof, which binds a plurality of b-chemokines, wherein said b-chemokines comprise MCP-2 and at least one other b-chemokine, which comprises at least one of the following CDR combinations: CDR1 and CDR2; CDR1 and CDR3; CDR2 and CDR3; and CDR1, CDR2, and CDR3, from the 1A1 heavy chain variable region described in SEQ ID NO: 11. In one embodiment, the antibody of the invention is a chimeric antibody. In another embodiment, the antibody of the invention is a humanized antibody.

a. Production of Chimeric Antibodies

The term "chimeric antibody" refers to an antibody whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. A typical chimeric antibody is thus a hybrid protein consisting of the V or antigen-binding domain from a mouse antibody and the C or effector domain from a human antibody.

b. Production of Humanized Antibodies

The term "humanized antibody" refers to an antibody comprising at least one chain comprising variable region framework residues substantially from a human antibody chain (referred to as the acceptor immunoglobulin or antibody) and at least one complementarity determining region substantially from a mouse-antibody, (referred to as the donor immunoglobulin or antibody). See, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693,762, Selick et al., WO 90/07861, and Winter, U.S. Pat. No. 5,225,539 (incorporated by reference in their entirety for all purposes). The constant region(s), if present, are also substantially or entirely from a human immunoglobulin.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., *Protein Engineering* 4:773 (1991); Kolbinger et al., *Protein Engineering* 6:971 (1993) and Carter et al., WO 92/22653.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular subject or during clinical trials. Subjects administered humanized antibodies can be given an immunogenicity assessment at the beginning and throughout the administration of said therapy. The HAMA response is measured, for example, by detecting antibodies to the humanized therapeutic reagent, in serum samples from the subject using a method known to one in the art, including surface plasmon resonance technology (BIACORE) and/or solid-phase ELISA analysis.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution is determined, in part, by computer modeling. Computer hardware and software are described herein for producing three-dimensional images of immunoglobulin molecules. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g., is within about 3-6 Å of a CDR region as determined by computer modeling), or (4) participates in the VL-VH interface.

Residues which "noncovalently bind antigen directly" include amino acids in positions in framework regions which are have a good probability of directly interacting with amino acids on the antigen according to established chemical forces, for example, by hydrogen bonding, Van der Waals forces, hydrophobic interactions, and the like.

CDR and framework regions are as defined by Kabat et al. or Chothia et al., supra. When framework residues, as defined by Kabat et al., supra, constitute structural loop residues as defined by Chothia et al., supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233: 747 (1986), which is incorporated herein by reference) and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to effect a CDR region. In one embodiment, residues that "otherwise interact with a CDR region" are identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (A) of some atom in the CDRs and must contain an atom that could interact with the CDR atoms according to established chemical forces, such as those listed above.

In the case of atoms that may form a hydrogen bond, the 3 Å is measured between their nuclei, but for atoms that do not form a bond, the 3 Å is measured between their Van der Waals surfaces. Hence, in the latter case, the nuclei must be within about 6 Å (3 Å plus the sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

The amino acids at several positions in the framework are known to be capable of interacting with the CDRs in many antibodies (Chothia and Lesk, supra, Chothia et al., supra and Tramontano et al., J. Mol. Biol. 215:175 (1990), all of which are incorporated herein by reference). Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized immunoglobulin.

Residues which "participate in the VL-VH interface" or "packing residues" include those residues at the interface between VL and VH as defined, for example, by Novotny and Haber, Proc. Natl. Acad. Sci. USA, 82:4592-66 (1985) or Chothia et al, supra. Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable; it is sometimes possible to make one or more conservative amino acid substitutions of CDR residues without appreciably affecting the binding affinity of the resulting humanized immunoglobulin. By conservative substitutions is intended combinations such as gly, ala; val, ile, leu; asp, glu; asn, gln; ser, thr; lys, arg; and phe, tyr.

Additional candidates for substitution are acceptor human framework amino acids that are "unusual" or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criterion help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions. Notably, CDR1 in the variable heavy chain is defined as including residues 26-32.

Additional candidates for substitution are acceptor framework residues that correspond to a rare or unusual donor framework residue. Rare or unusual donor framework residues are those that are rare or unusual (as defined herein) for murine antibodies at that position. For murine antibodies, the subgroup can be determined according to Kabat and residue positions identified which differ from the consensus. These donor specific differences may point to somatic mutations in the murine sequence which enhance activity. Unusual residues that are predicted to affect binding are retained, whereas residues predicted to be unimportant for binding can be substituted.

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence identity to a human variable framework region sequence or consensus of such sequences. In another embodiment, the variable framework region of the humanized immunoglobulin shares at least 90%, preferably 95%, more preferably 96%, 97%, 98% or 99% sequence identity to a human variable framework region sequence or consensus of such sequences. In general, however, such substitutions are undesirable.

The humanized antibodies preferably exhibit a specific binding affinity for antigen of at least $10^7$, $10^8$, $10^9$ or $10^{10}$, $10^{11}$, $10^{12}$, $10^{13}$ M$^{-1}$. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE (i.e., surface plasmon resonance using unlabelled reagents) or competitive binding assays.

c. Production of 11K2 Humanized Antibodies

A preferred embodiment of the present invention features a humanized antibody to MCPs, in particular, for use in therapeutic and/or diagnostic methodologies described herein. A particularly preferred starting material for production of humanized antibodies is 11K2. 11K2 is a pan-MCP antibody and is specific for MCP-1, MCP-2 and MCP-3. 11K2 has been shown to inhibit MCP-induced chemotaxis (see Examples 3 and 5). The cloning and sequencing of cDNA encoding the 11K2 antibody heavy and light chains is described in Example 10.

Suitable human acceptor antibody sequences are identified by computer comparisons of the amino acid sequences of the mouse variable regions with the sequences of known human antibodies. The comparison is performed separately for heavy and light chains but the principles are similar for each. In particular, variable domains from human antibodies whose framework sequences exhibit a high degree of sequence identity with the murine VL and VH framework regions were identified by query of the Kabat Database using NCBI BLAST (publicly accessible through the National Institutes of Health NCBI internet server) with the respective murine framework sequences. In one embodiment, acceptor sequences sharing greater that 50% sequence identity with murine donor sequences are selected. Preferably, acceptor antibody sequences sharing 60%, 70%, 80%, 90% or more are selected.

A computer comparison of 11K2 revealed that the 11K2 light chain shows the greatest sequence identity to human light chains of subtype kappa 1, and that the 11K2 heavy chain shows greatest sequence identity to human heavy chains of subtype 1, as defined by Kabat et al., supra. Thus, light and heavy human framework regions are preferably derived from human antibodies of these subtypes, or from consensus sequences of such subtypes. The preferred light chain human variable regions showing greatest sequence identity to the corresponding region from 11K2 are from antibodies GI486875 (Griffiths et al. (1993) *EMBO J.* 12(2), 725-734). The preferred heavy chain human variable regions showing greatest sequence identity to the corresponding region from 11K2 are from antibodies having Kabat ID Number 0000554 (Kipps and Duffy (1991), *J. Clin. Invest.* 87 (6): 2087-2096).

Residues are next selected for substitution, as follows. When an amino acid differs between a 11K2 variable framework region and an equivalent human variable framework region, the human framework amino acid should usually be substituted by the equivalent mouse amino acid if it is reasonably expected that the amino acid:

noncovalently binds antigen directly, is adjacent to a CDR region, is part of a CDR region under the alternative definition proposed by Chothia et al., supra, or otherwise interacts with a CDR region (e.g., is within about 3 of a CDR region) (e.g. amino acids at positions H29, H73, L49 of 11K2), or participates in the VL-VH interface Computer modeling of the 11K2 antibody heavy and light chain variable regions, and humanization of the 11K2 antibody is described in Example 14. Briefly, a three-dimensional model was generated based on the closest solved murine antibody structures for the heavy and light chains. For this purpose, an antibody designated 184.1 (Protein Data Bank (PDB) ID: 184.1) was chosen as a template for modeling the 11K2 light chain, and an antibody designated E8 (PDB ID: 1OPG) was chosen as the template for modeling the heavy chain. The model was further refined by a series of energy minimization steps to relieve unfavorable atomic contacts and optimize electrostatic and van der Walls interactions.

Three-dimensional structural information for the antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research,* 28:235. Computer modeling allows for the identification of CDR-interacting residues. The computer model of the structure of 11K2 can in turn serve as a starting point for predicting the three-dimensional structure of an antibody containing the 11K2 complementarity determining regions substituted in human framework structures. Additional models can be constructed representing the structure as further amino acid substitutions are introduced.

In general, substitution of one, most or all of the amino acids fulfilling the above criteria is desirable. Accordingly, the humanized antibodies of the present invention will usually contain a substitution of a human light chain framework residue with a corresponding 11K2 residue in at least 1, 2, and more usually 3, of the following positions: L49, L69 and L71. The humanized antibodies also usually contain a substitution of a human heavy chain framework residue with a corresponding 11K2 residue in at least 1, 2, 3, 4, 5, 6, and sometimes 7, of the following positions: H27, H28, H29, H30, H48, H677, and H73.

In one embodiment, the humanized antibodies of the invention are based on two versions of the humanized 11K2 variable heavy chain (H1 and H2) and two versions of the humanized 11K2 variable light chain (L1 and L2). The humanized antibody of the invention is based on any combination of these heavy and light chains (e.g. H1-L1, H1-L2, H2-L1, H2-L2). Version 1 of the humanized heavy and light chains contains most backmutations (i.e. L49, L69, L71, H27, H28, H29, H30, H48, H67, and H73), while version 2 contains the fewest (i.e. L49, L71, H27, H29, and H73). The sequence of humanized 11K2 variable heavy chain version 1 is set forth as SEQ ID NO: 47, and version 2 is set forth as SEQ ID NO: 48. The sequence of humanized 11K2 variable light chain version 1 is set forth as SEQ ID NO: 49, and version 2 is set forth as SEQ ID NO: 50.

In one embodiment, the humanized antibody of the invention contains a heavy chain comprising SEQ ID NO: 47 and a light chain comprising SEQ ID NO: 49. In another embodiment, the humanized antibody of the invention contains a heavy chain comprising SEQ ID NO: 47 and a light chain comprising SEQ ID NO: 50. In yet another embodiment, the humanized antibody of the invention contains a heavy chain comprising SEQ ID NO: 48 and a light chain comprising SEQ ID NO: 49. IN still another embodiment, the humanized antibody of the invention contains a heavy chain comprising SEQ ID NO: 48 and a light chain comprising SEQ ID NO: 50.

Occasionally, however, there is some ambiguity about whether a particular amino acid meets the above criteria, and alternative variant immunoglobulins are produced, one of which has that particular substitution, the other of which does not. In instances where substitution with a murine residue would introduce a residue that is rare in human immunoglobulins at a particular position, it may be desirable to test the antibody for activity with or without the particular substitution. If activity (e.g., binding affinity and/or binding specificity) is about the same with or without the substitution, the antibody without substitution may be preferred, as it would be expected to elicit less of a HAHA response, as described herein.

Other candidates for substitution are acceptor human framework amino acids that are unusual for a human immunoglobulin at that position. These amino acids can be substituted with amino acids from the equivalent position of more typical human immunoglobulins. Alternatively, amino acids from equivalent positions in the mouse 11K2 can be introduced into the human framework regions when such amino acids are typical of human immunoglobulin at the equivalent positions.

In additional embodiments, when the human light chain framework acceptor immunoglobulin is GI-486875, the light chain contains substitutions in at least 1, 2, 3, 4, 5, 6, 7, 8, 9, 10, or more usually 11, of the following positions: L8, L11, L13, L15, L42, L45, L74, L76, L80, L83, or L104. In additional embodiments when the human heavy chain framework acceptor immunoglobulin is Kabat ID Number 000054, the heavy chain contains substitutions in at least 1, 2, 3, 4, 5, 6, 7, 8, 9, 10, 11, 12, 13, 14, 15, 16, 17, or more usually 18, of the following positions: H1, H5, H11, H12, H14, H16, H20, H23, H38, H40, H42, H66, H75, H76, H80, H81, H82C, or H83. These positions are substituted with the amino acid from the equivalent position of a human immunoglobulin having a more typical amino acid residue. Examples of appropriate amino acids to substitute are shown in FIG. 11. Table 1 summarizes the sequence analysis of the 11K2 VH and VL regions.

TABLE 1

Summary of 11K2 V-region sequence

| | Chain | |
| --- | --- | --- |
| | Heavy | Light |
| Mouse subgroup | 2C | kappa 5 |
| Human subgroup | 1 | kappa 1 |
| Chothia canonical CDR groupings | H1: 5 residues, no class<br>H2: 17 residues, class 2<br>H3: 8 residues, no class | L1: 11 residues, class 2<br>L2: 7 residues, class 1<br>L3: 9 residues, class 1 |
| Closest solved mouse structure | E8 | 184.1 |

Kabat ID sequences referenced herein are publicly available, for example, from the Northwestern University Biomedical Engineering Department's Kabat Database of Sequences of Proteins of Immunological Interest. Three-dimensional structural information for antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research*, p 235-242. Germline gene sequences referenced herein are publicly available, for example, from the National Center for Biotechnology Information (NCBI) database of sequences in collections of Igh, Ig kappa and Ig lambda germline V genes (as a division of the National Library of Medicine (NLM) at the National Institutes of Health (NIH)). Homology searching of the NCBI "Ig Germline Genes" database is provided by IgG BLAST™.

d. Production of 1A1 Humanized Antibodies

Another preferred embodiment of the present invention features a humanized antibody to MCPs, in particular, for use in therapeutic and/or diagnostic methodologies described herein, wherein the starting material for production of humanized antibodies is 1A1. 1A1 is a pan-MCP antibody, and is specific for MCP-1, MCP-2 and MCP-3. 1A1 has been shown to inhibit MCP-induced chemotaxis (see Examples 3 and 5). The cloning and sequencing of cDNA encoding the 1A1 antibody heavy and light chains is described in Example 9.

Suitable human acceptor antibody sequences are identified by computer comparisons of the amino acid sequences of the mouse variable regions with the sequences of known human antibodies. The comparison is performed separately for heavy and light chains but the principles are similar for each. In particular, variable domains from human antibodies whose framework sequences exhibit a high degree of sequence identity with the murine VL and VH framework regions were identified by query of the Kabat Database using NCBI BLAST (publicly accessible through the National Institutes of Health NCBI internet server) with the respective murine framework sequences. In one embodiment, acceptor sequences sharing greater that 50% sequence identity with murine donor sequences are selected. Preferably, acceptor antibody sequences sharing 60%, 70%, 80%, 90% or more are selected.

A computer comparison of 1A1 revealed that the 1A1 light chain is a member of mouse subgroup kappa 2 and shows the greatest sequence identity to human light chains of subtype kappa 2. The comparison also revealed that the 1A1 heavy chain is a member of mouse subgroup 2C and shows greatest sequence identity to human heavy chains of subgroup 1, as defined by Kabat et al., supra. Thus, light and heavy human framework regions are preferably derived from human antibodies of these subtypes, or from consensus sequences of such subtypes. The preferred light chain human variable regions showing greatest sequence identity to the corresponding region from 1A1 are from antibodies GI-284256 (Kennedy et al. (1991) *J. Exp. Med.* 173(4), 1033-1036). The preferred heavy chain human variable regions showing greatest sequence identity to the corresponding region from 1A1 are from antibodies having Kabat ID Number 037655 (Bejeck et al. (1995), *Cancer Res.* 55(11): 2346-2351).

Residues are next selected for substitution, as follows. When an amino acid differs between a 1A1 variable framework region and an equivalent human variable framework region, the human framework amino acid should usually be substituted by the equivalent mouse amino acid if it is reasonably expected that the amino acid:

(1) noncovalently binds antigen directly,
(2) is adjacent to a CDR region, is part of a CDR region under the alternative definition proposed by Chothia et al., supra, or otherwise interacts with a CDR region (e.g., is within about 3 of a CDR region) (e.g. amino acids at positions H30, H73, or H93 of 1A1), or
(3) participates in the VL-VH interface (e.g. amino acids at positions L36 and H91 of 1A1).

Computer modeling of the 1A1 antibody heavy and light chain variable regions, and humanization of the 1A1 antibody is described in the Examples. Briefly, a three-dimensional model was generated based on the closest solved murine antibody structures for the heavy and light chains. For this purpose, an antibody designated Fab1583 (1NLD; 2.9 Å) and D2.5 (1YEE; 2.2 Å) were chosen as templates for modeling the 1A1 light chain, and antibodies designated 2E8 (12E8; 1.9 Å) and F9.13.7 (1FB1; 3.0 Å) were chosen as templates for modeling the heavy chain. The model was further refined by a series of energy minimization steps to relieve unfavorable atomic contacts and optimize electrostatic and van der Walls interactions.

Three-dimensional structural information for the antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research,* 28:235. Computer modeling allows for the identification of CDR-interacting residues. The computer model of the structure of 1A1 can in turn serve as a starting point for predicting the three-dimensional structure of an antibody containing the 1A1 complementarity determining regions substituted in human framework structures. Additional models can be constructed representing the structure as further amino acid substitutions are introduced.

In general, substitution of one, most or all of the amino acids fulfilling the above criteria is desirable. Accordingly, the humanized antibodies of the present invention will usually contain a substitution of a human light chain framework residue with a corresponding 1A1 residue in at least 1, 2, and sometimes 3, of the following positions: L2, L36, and L45. The humanized antibodies also usually contain a substitution of a human heavy chain framework residue with a corresponding 1A1 residue in at least 1, 2, 3, 4, 5, 6, 7, 8, 9, 10, and sometimes 11, of the following positions: H27, H28, H29, H30, H66, H69, H73, H76, H91, H93, and H94.

In one embodiment, the humanized antibodies of the invention are based on two versions of the humanized 1A1 variable heavy chain (H1 and H2) and two versions of the humanized 1A1 variable light chain (L1 and L2). The humanized antibody of the invention is based on any combination of the 1A1 humanized heavy and light chains (e.g. H1-L1, H1-L2, H2-L1, H2-L2). Version 1 of the humanized heavy and light chains contains most backmutations (i.e. L2, L36, L45, H27, H28, H29, H30, H66, H69, H73, H76, H91, H93, and H94), while version 2 contains the fewest (i.e. L2, L36, H29, H30, H73, H91, H93, and H94). The sequence of humanized 1A1 variable heavy chain version 1 is set forth as SEQ ID NO: 53, and version 2 is set forth as SEQ ID NO: 54. The sequence of humanized 1A1 variable light chain version 1 is set forth as SEQ ID NO: 55, and version 2 is set forth as SEQ ID NO: 56.

In one embodiment, the humanized antibody of the invention contains a heavy chain comprising SEQ ID NO: 53 and a light chain comprising SEQ ID NO: 55. In another embodiment, the humanized antibody of the invention contains a heavy chain comprising SEQ ID NO: 53 and a light chain comprising SEQ ID NO: 56. In yet another embodiment, the humanized antibody of the invention contains a heavy chain comprising SEQ ID NO: 54 and a light chain comprising SEQ ID NO: 55. In still another embodiment, the humanized antibody of the invention contains a heavy chain comprising SEQ ID NO: 554 and a light chain comprising SEQ ID NO: 56.

Occasionally, however, there is some ambiguity about whether a particular amino acid meets the above criteria, and alternative variant immunoglobulins are produced, one of which has that particular substitution, the other of which does not. In instances where substitution with a murine residue would introduce a residue that is rare in human immunoglobulins at a particular position, it may be desirable to test the antibody for activity with or without the particular substitution. If activity (e.g., binding affinity and/or binding specificity) is about the same with or without the substitution, the antibody without substitution may be preferred, as it would be expected to elicit less of a HAHA response, as described herein.

Other candidates for substitution are acceptor human framework amino acids that are unusual for a human immunoglobulin at that position. These amino acids can be substituted with amino acids from the equivalent position of more typical human immunoglobulins. Alternatively, amino acids from equivalent positions in the mouse 11K2 can be introduced into the human framework regions when such amino acids are typical of human immunoglobulin at the equivalent positions.

In additional embodiments, when the human light chain framework acceptor immunoglobulin is GI-284256, the light chain contains substitutions in at least 1, 2, 3, 4, 5, 6, 7, 8, or more usually 9, of the following positions: L3, L8, L9, L11, L12, L14, L37, L63, or L99. In additional embodiments when the human heavy chain framework acceptor immunoglobulin is Kabat ID Number 037655, the heavy chain contains substitutions in at least 1, 2, 3, 4, 5, 6, 7, 8, or more usually 9, of the following positions: H1, H6, H14, H16, H23, H42, H80, H82B, or H87. These positions are substituted with the amino acid from the equivalent position of a human immunoglobulin having a more typical amino acid residue. Examples of appropriate amino acids to substitute are shown in FIG. 11. Table 2 summarizes the sequence analysis of the 1A1 VH and VL regions.

TABLE 2

Summary of 1A1 V-region sequence

| | Chain | |
| --- | --- | --- |
| | Heavy | Light |
| Mouse subgroup | 2C | kappa 2 |
| Human subgroup | 1 | kappa 2 |
| Chothia canonical CDR groupings | H1: 5 residues, class 1 | L1: 16 residues, class 4 |
| | H2: 17 residues, class 2 | L2: 7 residues, class 1 |
| | H3: 13 residues, no class | L3: 9 residues, class 1 |
| Closest solved mouse structure | 2E8 (12E8; 1.9 Å) | Fab1583 (1NLD; 2.9 Å) |
| | F9.13.7 (1FB1; 3.0 Å) | D2.5 (1YEE; 2.2 Å) |

Kabat ID sequences referenced herein are publicly available, for example, from the Northwestern University Biomedical Engineering Department's Kabat Database of Sequences of Proteins of Immunological Interest. Three-dimensional structural information for antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research*, p 235-242. Germline gene sequences referenced herein are publicly available, for example, from the National Center for Biotechnology Information (NCBI) database of sequences in collections of Igh, Ig kappa and Ig lambda germline V genes (as a division of the National Library of Medicine (NLM) at the National Institutes of Health NIH)). Homology searching of the NCBI "Ig Germline Genes" database is provided by IgG BLAST™.

In another embodiment, a humanized antibody of the present invention has structural features, as described herein, and specifically binds to an epitope comprising MCP-1 and MCP-2.

3. Human Antibodies

Human antibodies against MCPs are provided by a variety of techniques described below. Some human antibodies are selected by competitive binding experiments, or otherwise, to have the same epitope specificity as a particular mouse antibody, such as one of the mouse monoclonals described herein. Human antibodies can also be screened for a particular epitope specificity by using only a fragment of an MCP molecule as the immunogen, and/or by screening antibodies against a collection of deletion mutants of MCP. Human antibodies preferably have human IgG1 isotype specificity.

a. Trioma Methodology

The basic approach and an exemplary cell fusion partner, SPAZ-4, for use in this approach have been described by Oestberg et al., Hybridoma 2:361 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells; two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For example, for in vivo immunization, B cells are typically isolated from a human immunized with MCP-1, a fragment thereof, larger polypeptide containing MCP-1 or fragment, or an anti-idiotypic antibody to an antibody to MCP-1. In some methods, B cells are isolated from the same subject who is ultimately to be administered antibody therapy. For in vitro immunization, B-lymphocytes are typically exposed to antigen for a period of 7-14 days in a media such as RPMI-1640 (see Engleman, supra) supplemented with 10% human plasma.

The immunized B-lymphocytes are fused to a xenogeneic hybrid cell such as SPAZ-4 by well-known methods. For example, the cells are treated with 40-50% polyethylene glycol of MW 1000-4000, at about 37 degrees C., for about 5-10 min. Cells are separated from the fusion mixture and propagated in media selective for the desired hybrids (e.g., HAT or AH). Clones secreting antibodies having the required binding specificity are identified by assaying the trioma culture medium for the ability to bind to Aβ or a fragment thereof. Triomas producing human antibodies having the desired specificity are subcloned by the limiting dilution technique and grown in vitro in culture medium. The trioma cell lines obtained are then tested for the ability to bind Aβ or a fragment thereof.

Although triomas are genetically stable they do not produce antibodies at very high levels. Expression levels can be increased by cloning antibody genes from the trioma into one or more expression vectors, and transforming the vector into standard mammalian, bacterial or yeast cell lines.

b. Transgenic Non-Human Mammals

Human antibodies against MCPs can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148:1547 (1994), *Nature Biotechnology* 14:826 (1996), Kucherlapati, WO 91/10741 (1991) (each of which is incorporated by reference in its entirety for all purposes). Transgenic mice are particularly suitable. For example, anti-MCP-1 antibodies are obtained by immunizing a transgenic nonhuman mammal, such as described by Lonberg or Kucherlapati, supra, with MCP-1 or a fragment thereof. Monoclonal antibodies are prepared by, e.g. fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using MCP-1 or other MCP peptide as an affinity reagent.

c. Phage Display Methods

A further approach for obtaining human anti-MCP antibodies is to screen a DNA library from human B cells according to the general protocol outlined by Huse et al., *Science* 246:1275-1281 (1989). As described for trioma methodology, such B cells can be obtained from a human immunized with MCP-1, fragments, longer polypeptides containing MCP-1 or fragments or anti-idiotypic antibodies. Optionally, such B cells are obtained from a subject who is ultimately to receive antibody treatment. Antibodies binding to MCP-1 or a fragment thereof are selected. Sequences encoding such antibodies (or a binding fragments) are then cloned and amplified. The protocol described by Huse is rendered more efficient in combination with phage-display technology. See, e.g., Dower et al., WO 91/17271, McCafferty et al., WO 92/01047, Herzig et al., U.S. Pat. No. 5,877,218, Winter et al., U.S. Pat. No. 5,871,907, Winter et al., U.S. Pat. No. 5,858,657, Holliger et al., U.S. Pat. No. 5,837,242, Johnson et al., U.S. Pat. No. 5,733,743 and Hoogenboom et al., U.S. Pat. No. 5,565,332 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an MCP-1 peptide or fragment thereof.

In a variation of the phage-display method, human antibodies having the binding specificity of a selected murine antibody can be produced. See Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for MCP-1, MCP-2, MCP-3, or a combination thereof (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for MCP-1, MCP-2, MCP-3, or a combination thereof, are selected. These phage display the variable regions of completely human anti-MCP antibodies. These antibodies usually have the same or similar epitope specificity as the murine starting material.

4. Production of Variable Regions

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

5. Selection of Constant Regions

The variable segments of antibodies produced as described supra (e.g., the heavy and light chain variable regions of chimeric, humanized, or human antibodies) are typically linked to at least a portion of an immunoglobulin constant region (Fc), typically that of a human immunoglobulin. Human constant region DNA sequences can be isolated in accordance with well known procedures from a variety of human cells, but preferably immortalized B cells (see Kabat et al., supra, and Liu et al., WO87/02671) (each of which is incorporated by reference in its entirety for all purposes). Ordinarily, the antibody will contain both light chain and heavy chain constant regions. The heavy chain constant region usually includes CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. The choice of constant region depends, in part, whether antibody-dependent complement and/or cellular mediated toxicity is desired. For example, isotypes IgG1 and IgG3 have complement activity and isotypes IgG2 and IgG4 do not. When it is desired that the antibody (e.g., humanized antibody) exhibit cytotoxic activity, the constant domain is usually a complement fixing constant domain and the class is typically IgG1. When such cytotoxic activity is not desirable, the constant domain may be of the IgG2 class. Choice of isotype can also affect passage of antibody into the brain. Human isotype IgG1 is preferred. Light chain constant regions can be lambda or kappa The humanized antibody may comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

6. Chemical Modifications

In some embodiments, the antibodies and antibody fragments of the invention may be chemically modified to provide a desired effect. For example, pegylation of antibodies and antibody fragments of the invention may be carried out by any of the pegylation reactions known in the art, as described, for example, in the following references: Focus on Growth Factors 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat conditions that may be alleviated or modulated by administration of the antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions. In one embodiment, the invention describes pegylated Fab antibodies, including pegylated humanized Fab-11K2 and pegylated murine Fab-11K2.

In other embodiments of the invention the antibodies or antigen-binding fragments thereof are conjugated to albumen using art recognized techniques.

In another embodiment of the invention, antibodies, or fragments thereof, are modified to reduce or eliminate potential glycosolyation sites. Such modified antibodies are often referred to as "aglycosylated" antibodies. In order to improve the binding affinity of an antibody or antigen-binding fragment thereof, glycosylation sites of the antibody can be altered, for example, by mutagenesis (e.g., site-directed mutagenesis). "Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. In order to identify potential glycosylation sites within an antibody or antigen-binding fragment, the sequence of the antibody is examined, for example, by using publicly available databases such as the website provided by the Center for Biological Sequence Analysis (available at world wide web cbs.dtu.dk/services/NetNGlyc/ for predicting N-linked glycosylation sites and world wide web cbs.dtu.dk/services/NetOGlyc/ for predicting O-linked glycosylation sites). Additional methods for altering glycosylation sites of antibodies are described in U.S. Pat. Nos. 6,350,861 and 5,714,350.

In yet another embodiment of the invention, antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor (FcR), the immunoglobulin constant region segment of the antibody can be mutated at particular regions necessary for FcR interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

In a particular embodiment the invention further features antibodies having altered effector function, such as the ability to bind effector molecules, for example, complement or a receptor on an effector cell. In particular, the humanized antibodies of the invention have an altered constant region, e.g., Fc region, wherein at least one amino acid residue in the Fc region has been replaced with a different residue or side chain thereby reducing the ability of the antibody to bind the FcR. Reduction in FcR binding ability of the antibody may also reduce other effector functions which rely on FcR interactions, such as opsonization and phagocytosis and antigen-dependent cellular cytotoxicity. In one embodiment, the modified humanized antibody is of the IgG class, comprises at least one amino acid residue replacement in the Fc region such that the humanized antibody has an altered effector function, e.g., as compared with an unmodified humanized antibody. In particular embodiments, the humanized antibody of the invention has an altered effector function such that it is less immunogenic (e.g., does not provoke undesired effector cell activity, lysis, or complement binding), and/or has a more desirable half-life while retaining specificity for MCP1, MCP-2, and/or MCP-3.

Alternatively, the invention features humanized antibodies having altered constant regions to enhance FcR binding, e.g., FcγR3 binding. Such antibodies are useful for modulating effector cell function, e.g., for increasing ADCC activity, e.g., particularly for use in oncology applications.

As used herein, "Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC; NK cells, express FcγRIII only, whereas monocytes express FcγRI, FcγRII and FcγRIII. of the antibody, e.g., a conjugate of the antibody and another agent or antibody.

7. Expression of Recombinant Antibodies

Chimeric, humanized and human antibodies are typically produced by recombinant expression. Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

Alternatively, antibody-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

The invention also includes aglycosylated antibodies, which may be desirable for therapeutic treatment of human disease. Humanized antibodies with altered glycosylation are produced by expression of a nucleic acid encoding a human antibody in a cell line that has altered ability to post-translationally modify polypeptides, e.g., glycosylate polypeptides. For example, e.g, EP 1,176,195 describes a fucosyltransferase mutant, WO 99/54342 describes a CHO cell line engineered with regulatable GntIII expression resulting in increased bisecting GlcNAc structures having enhanced effector function, Shields et al. ((2002) J. Biol. Chem. 277 26733) describes a hypofucosylated anti-HER2 hu4D5 mAb made in mutant lec13 cells has improved ADCC, and Umana et al. ((1999) Nat. Biotechnol. 17: 176) describes a mAb with altered bisecting glycoforms made in cells overexpressing rat GnTIII that exhibits improved ADCC.

8. Antibody Fragments

Also contemplated within the scope of the instant invention are antibody fragments. In one embodiment, fragments of non-human, chimeric and/or human antibodies are provided. In another embodiment, fragments of humanized antibodies are provided. Typically, these fragments exhibit specific binding to antigen with an affinity of at least $10^7$, and more typically $10^8$ or $10^9$ M$^{-1}$. Humanized antibody fragments include separate heavy chains, light chains Fab, Fab' F(ab')2, Fabc, and Fv. Preferred fragments of the invention include humanized 11K2 Fab and humanized 1A1 Fab antibodies. In yet another embodiment, the invention includes murine 11K2 Fab fragments and 1A1 Fab fragments. Fragments are produced by recombinant DNA techniques, or by enzymatic or chemical separation of intact immunoglobulins.

B. Nucleic Acid Encoding Immunologic and Therapeutic Agents

Immune responses against MCPs can also be induced by administration of nucleic acids encoding antibodies and their component chains used for passive immunization. Such nucleic acids can be DNA or RNA. A nucleic acid segment encoding an immunogen is typically linked to regulatory elements, such as a promoter and enhancer, that allow expression of the DNA segment in the intended target cells of a subject. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, Cur. Opin. Genet. Develop. 3:102-109 (1993)); adenoviral vectors (see, e.g., Bett et al., J. Virol. 67:5911 (1993)); adeno-associated virus vectors (see, e.g., Zhou et al., J. Exp. Med. 179:1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70:508 (1996)), Venezuelan equine encephalitis virus (see Johnston et al., U.S. Pat. No. 5,643,576) and rhabdoviruses, such as vesicular stomatitis virus (see Rose, WO 96/34625) and papillomaviruses (Ohe et al., Human Gene Therapy 6:325 (1995); Woo et al., WO 94/12629 and Xiao & Brandsma, Nucleic Acids. Res. 24, 2630-2622 (1996)).

DNA encoding an immunogen, or a vector containing the same, can be packaged into liposomes. Suitable lipids and related analogs are described by Eppstein et al., U.S. Pat. No. 5,208,036, Felgner et al., U.S. Pat. No. 5,264,618, Rose, U.S. Pat. No. 5,279,833, and Epand et al., U.S. Pat. No. 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., J. Micro Encap. (1996).

Gene therapy vectors or naked polypeptides (e.g. DNA) can be delivered in vivo by administration to an individual subject, typically by systemic administration (e.g., intravenous, intraperitoneal, nasal, gastric, intradermal, intramuscular, subdermal, or intracranial infusion) or topical application (see e.g., Anderson et al., U.S. Pat. No. 5,399,346). The term "naked polynucleotide" refers to a polynucleotide not complexed with colloidal materials. Naked polynucleotides are sometimes cloned in a plasmid vector. Such vectors can further include facilitating agents such as bupivacine (Attardo et al., U.S. Pat. No. 5,593,970). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see Howell et al., WO 95/05853).

In a further variation, vectors encoding immunogens can be delivered to cells ex vivo, such as cells explanted from an individual subject (e.g., lymphocytes, bone marrow aspirates, tissue biopsy) or universal donor hematopoietic stem cells, followed by reimplantation of the cells into a subject, usually after selection for cells which have incorporated the vector.

II. Prophylactic and Therapeutic Methods

The present invention is directed inter alia to treatment of diseases associated with MCP-associated inflammation, by administration of therapeutic immunological reagents (e.g., humanized immunoglobulins) to specific epitopes within an MCP protein to a subject under conditions that generate a beneficial therapeutic response in a subject, for example, for the prevention or treatment of a disorder associated with detrimental MCP activity. The invention is also directed to use of the disclosed immunological reagents (e.g., humanized immunoglobulins) in the manufacture of a medicament for the treatment or prevention of an MCP-associated disease.

The term "treatment" as used herein, is defined as the application or administration of a therapeutic agent to a subject, or application or administration of a therapeutic agent to an isolated tissue or cell line from a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

The methods can be used on both asymptomatic subjects and those currently showing symptoms of disease. The antibodies used in such methods can be human, humanized, chimeric or nonhuman antibodies, or fragments thereof (e.g., antigen binding fragments) and can be monoclonal or polyclonal, as described herein. In yet another aspect, the invention features administering antibodies prepared from a human immunized with an MCP peptide, which human can be the subject to be treated with antibody.

In another aspect, the invention features administering an antibody with a pharmaceutical carrier as a pharmaceutical composition. Alternatively, the antibody can be administered to a subject by administering a polynucleotide encoding at least one antibody chain. The polynucleotide is expressed to produce the antibody chain in the subject. Optionally, the polynucleotide encodes heavy and light chains of the antibody. The polynucleotide is expressed to produce the heavy and light chains in the subject. In exemplary embodiments, the subject is monitored for level of administered antibody in the blood of the subject.

The invention thus fulfills a longstanding need for therapeutic regimes for preventing or ameliorating inflammation associated with MCPs.

A. Disorders Amenable to Treatment

As used herein, the terms "a disorder in which MCP activity is detrimental" and "an MCP-associated disorder" are intended to include diseases and other disorders in which the presence of MCP, including MCP-1, MCP-2, and/or MCP-3, in a subject suffering from the disorder has been shown to be or is suspected of being either responsible for the pathophysiology of the disorder or a factor that contributes to a worsening of the disorder. Accordingly, a disorder in which MCP activity is detrimental is a disorder in which inhibition of MCP activity is expected to alleviate the symptoms and/or progression of the disorder. Such disorders may be evidenced, for example, by an increase in the concentration of MCP in a biological fluid of a subject suffering from the disorder (e.g., an increase in the concentration of MCP-1 in serum, plasma, synovial fluid, etc. of the subject), which can be detected, for example, using an anti-MCP antibody as described above. There are numerous examples of disorders in which MCP activity is detrimental. The use of the antibodies and antibody portions of the invention in the treatment of specific disorders is discussed further below.

The b-chemokines, particularly MCP-1, MCP-2 and MCP-3 have been shown to play a role in pathological conditions associated with inflammation (Van Coillie et al. (1999) *Cytokine & Growth Factor Rev.* 10:61-86). MCP-1, MCP-2, and MCP-3 have all been shown to have potent chemotactic activity for leukocytes, especially monocytes (van Coillie et al (1999) *Cytokine & Growth Factor Rev.* 10:61-86). All three chemokines also share other functions (e.g., glucosaminidase release, gelatinase B release, granzyme A) which combined with their chemotactic activity enable leukocytes to migrate into tissues and towards sites of inflammation. Recruitment of leukocytes to inflammatory sites is thought to contribute greatly to the inflammatory process. Inhibition of leukocyte recruitment via MCP-1 antagonism (e.g., in MCP-1 knockout animals and in MCP-1 depletion studies using anti-MCP-1 mAbs) has been shown to reduce leukocyte infiltration (particularly monocyte recruitment) and is correlated with reduction in disease (van Coillie et al. (1999) *Cytokine & Growth Factor Rev.* 10:61-86). Like MCP-1, MCP-2 and MCP-3 are also molecules with potent chemotactic activity for monocytes, T lymphocytes, and basophils. Given their overlapping activities and the increased expression of all three chemokines (MCP-1, MCP-2, and MCP-3) in human disease, blockade of all three MCP molecules would be expected to have a greater beneficial effect than just inhibition of MCP-1 alone. Blockade of multiple MCP molecules (MCP-1, MCP-2 and MCP-3) would also more efficiently inhibit recruitment of certain cell types for which MCP-1 is a poor chemotactic stimulus. Thus, while MCP-1 does not efficiently induce migration of eosinophils or resting neutrophils, MCP-2 is a potent chemotactic stimulus for eosinophils, and MCP-3 shows activity against both eosinophils and neutrophils (van Coillie et al. (1999) *Cytokine & Growth Factor Rev.* 10:61-86). The antibodies and antibody fragments of the invention may be used to modulate the activity of these chemokines and affect the pathology of these disorders, and therefore, may be used in therapeutic compositions for the treatment of inflammatory conditions and pathological conditions associated with expression of MCP molecules. In these embodiments, a subject is identified as having one of the diseases to be treated, such as by exhibiting at least one sign or symptom of the disease or disorder. At least one antibody or antigen-binding fragment thereof of the invention or compositions comprising at least one antibody or antigen-binding fragment thereof of the invention is administered in a sufficient amount to alleviate at least one symptom of the disease or disorder, or to reduce the activity of at least one of MCP-1, MCP-2 or MCP-3.

1. Fibrotic Disease

In one embodiment of the invention, an antibody or antigen-binding fragment thereof, having binding specificity for MCP-1, MCP-2 and/or MCP-3, e.g., an antibody or antigen-binding fragment comprising CDRs from either the 1A1 or 11K2 antibodies, is used in a method of prevention or treatment of a subject suffering from a fibrotic disease. A "fibrotic disease" as used herein includes any condition marked by an increase of interstitial fibrous tissue. MCPs are known to be associated with fibrotic conditions. For example, MCP-1 is a potent chemoattractant for monocytes and has been implicated in a variety of inflammatory and fibrotic diseases, the pathogenesis of which is known to involve infiltration and activation of monocytes (Zhang, et al (1994) *J. Immunol.* 153:4733-4741). Along with increased TGF-β and collagen production, fibrotic diseases are also characterized by increased levels of MCP-1 (Antoniades et al. (1992) *J. Immunol* 89:5371-5375; Wada et al. (1996) *FASEB J.,* 10:1418-1425; Saitoh et al. (1998) *J. Clin. Lab. Anal.* 12:1-5; Hasegawa et al. (1999) *Clin. Exp. Immunol.* 117:159-165; Wada et al. (1999) *Kidney Int.* 65:995-1003; Wada et al. (2000) *Kidney Int.* 58-1492-1499). Increased expression of MCP-1 during fibrotic diseases has been well characterized in both human and in rodent models. In humans, MCP-1 is up-regulated in idiopathic pulmonary fibrosis (Antoniades et al., supra), IgA nephropathy (Saitoh et al., supra), diabetic nephropathy (Wada et al. (2000), supra), lupus nephritis (Wada et al. (1996), supra), crescentic glomerulonephritis (Wada, 1999), supra), and scleroderma (Hasegawa, supra). While not expressed in normal tissues, MCP-1 was highly expressed in the fibrotic skin and lungs of scleroderma subjects, and the elevated levels of MCP-1 found in subject serum correlated with the presence of fibrosis and with earlier onset of scleroderma (Hasegawa, supra). MCP-1 expression also correlated positively with severity of renal fibrosis in diseases such as IgA nephropathy, diabetic nephropathy, lupus nephritis, and crescentic glomerulonephritis.

2. Oncogenic Disease

In another embodiment of the invention, an antibody or antigen-binding fragment thereof, having binding specificity for MCP-1, MCP-2 and/or MCP-3, e.g. an antibody or antigen-binding fragment comprising CDRs from either the 1A1 or 11K2 antibodies, is used in a method of prevention or treatment of a subject suffering from an oncogenic disease or cancer. MCPs are known to be associated with oncogenic conditions. For example, MCP-1 is a potent inducer of angiogenesis and plays an important role in tumor growth. Evidence for a role of MCP-1 in tumorigenesis involved treatment of immunodeficient mice bearing MCP-1 producing human breast carcinoma cells with neutralizing anti-MCP-1 mAb (Salcedo, (2000) *Blood* 96:34-40). Treatment with anti-MCP-1 mAb resulted in significant increases in animal survival (mean survival increased from 45 days to 75 days) and marked inhibition of tumor metastasis (60% decrease in lung metastatic index).

3. Immunopathologic Disease

In another embodiment of the invention, an antibody or antigen-binding fragment thereof, having binding specificity for MCP-1, MCP-2 and/or MCP-3, e.g., an antibody or antigen-binding fragment comprising CDRs from either the 1A1 or 11K2 antibodies, is used in a method of prevention or treatment of a subject suffering from an immunopathologic disease. An "immunopathologic disease" as used herein is defined as any condition associated with an immune response which is related to a disease. MCPs have been associated with immunopathologic conditions. For example, there is a strong link between MCP-1 expression and immunopathologic disease in humans. Experiments using genetically-engineered mice and in vivo data using function-blocking antibodies to MCP-1 provide evidence supporting the validity of MCP-1 antagonism in a variety of diseases characterized by mononuclear infiltration. Included among these diseases is: atherosclerosis (MCP-1 KO, CCR2 KO), arthritis (MCP-1 mAb), asthma (MCP-1 mAb), glomerulonephritis (MCP-1 KO, MCP-1 mAb), lupus nephritis (MCP-1 KO) and multiple sclerosis (MCP-1 KO, MCP-1 mAb, CCR2 KO) (see, for example, Lu et al. (1998) *J. Exp. Med.* 187601-608); Kurihara et al. (1997) *J. Exp. Med.* 186:1757-1762; Boring et al. (1997) *J. Clin. Invest.* 100:2552-2561); Kuziel et al. (1997) *PNAS* 94:12053-12058; Blease et al. (2000) *J. Immunol.* 165:2603-2611; Traynor et al. (2000) *J. Immunol.* 164:2021-2027; Boring et al. (1998) *Nature* 394:894-897; Dawson et al. (1999) *Atherosclerosis* 143:205-211; Fife et al. (2000) *J. Exp. Med.* 192: 899-905; Izikson et al. (2000) *J. Exp. Med.* 192:1075-1080; Bird et al. (2000) *Kidney Int.* 57:129-136; MacLean et al. (2000) *J. Immunol.* 165:165:6568-6575; Karpus et al. (1997) *J. Leukoc. Biol.* 62:681-687; Gonzalo et al. (1998) *J. Exp. Med.* 188:157-167). In all these cases, interference with the MCP-1 pathway resulted in dramatically reduced leukocyte infiltration, with monocyte recruitment being particularly affected. This dramatic reduction in monocyte recruitment correlated well with reduction in disease.

4. Other Disorders

In certain embodiments, the antibodies or antigen-binding fragments of the present invention are useful in the prevention or treatment of glomerulonephritis, scleroderma, cirrhosis, multiple sclerosis, lupus nephritis, atherosclerosis, inflammatory bowel diseases or rheumatoid arthritis. In another embodiment, the antibodies or antigen-binding fragments of the invention can be used to treat or prevent inflammatory disorders, including, but not limited to, Alzheimer's, severe asthma, atopic dermatitis, cachexia, CHF-ischemia, coronary restinosis, Crohn's disease, diabetic nephropathy, lymphoma, psoriasis, fibrosis/radiation-induced, juvenile arthritis, stroke, inflammation of the brain or central nervous system caused by trauma, and ulcerative colitis. Other inflammatory disorders which can be prevented or treated with the antibodies or antigen-binding fragments of the invention include inflammation due to corneal transplantation, chronic obstructive pulmonary disease, hepatitis C, multiple myeloma, and osteoarthritis. In another embodiment, the antibodies or antigen-binding fragments of the invention can be used to prevent or treat neoplasia, including, but not limited to bladder cancer, breast cancer, head and neck cancer, kaposi's sarcoma, melanoma, ovarian cancer, small cell lung cancer, stomach cancer, leukemia/lymphoma, and multiple myeloma. Additional neoplasia conditions include, cervical cancer, colo-rectal cancer, endometrial cancer, kidney cancer, non-squamous cell lung cancer, and prostate cancer. In another embodiment, the antibodies or antigen-binding fragments of the invention can be used to prevent or treat fibrotic disorders, including, but not limited to CHF-ischemia, coronary restenosis, diabetic vasculopathy, myocardial infarction/unstable angina, and radiation fibrosis. Additional examples of fibrotic disorders which can be treated in accordance with the invention include diabetic nephropathy, and impotence (Peyronie's). In another embodiment, the antibodies or antigen-binding fragments of the invention can be used to prevent or treat neurodegenerative disorders, including, but not limited to Alzheimer's, stroke, and traumatic brain or central nervous system injuries. Additional neurodegenerative disorders include ALS/motor neuron disease, diabetic peripheral neuropathy, diabetic retinopathy, Huntington's disease, macular degeneration, and Parkinson's disease.

In clinical applications, a subject is identified as having or at risk of developing a disease or disorder associated with detrimental MCP activity, such as by exhibiting at least one sign or symptom of the disease or disorder. At least one antibody or antigen-binding fragment thereof of the invention or compositions comprising at least one antibody or antigen-binding fragment thereof of the invention is administered in a sufficient amount to treat at least one symptom of the disease or disorder, or to reduce the activity of at least one of MCP-1, MCP-2 or MCP-3.

B. Animal Model for Testing Efficacy of Antibodies

Moreover, an antibody of the invention can be administered to a non-human mammal expressing a chemokine with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Examples of animal models which can be used for evaluating the therapeutic efficacy of antibodies or antigen-binding fragments of the invention for preventing or treating glomerulonephritis include anti-GBM-induced glomerulonephritis (Wada et al. (1996) *Kidney Int.* 49:761-767) and anti-thy1-induced glomerulonephritis (Schneider et al. (1999) *Kidney Int.* 56:135-144). Examples of animal models which can be used for evaluating the therapeutic efficacy of antibodies or antigen-binding fragments of the invention for preventing or treating colitis include a mouse model where colitis is TNBS-induced, as described in Neurath et al. (1995) *J Exp Med.* 182(5):1281. Examples of animal models which can be used for evaluating the therapeutic efficacy of antibodies or antigen-binding fragments of the invention for preventing or treating cirrhosis include carbon tetrachloride-induced cirrhosis and liver fibrosis (Sakadamis et al. (2001) *Res Exp Med* 200:137-54). Examples of animal models which can be used for evaluating the therapeutic efficacy of antibodies or antigen-binding fragments of the invention for preventing or treating multiple sclerosis include experimental autoimmune encephalomyelitis (EAE) (Link and Xiao (2001) *Immunol. Rev.* 184:117-128). Animal models can also be used for evaluating the therapeutic efficacy of antibodies or antigen-binding fragments of the invention for preventing or treating lupus, for example using the MRL-Fas$^{lpr}$ mice (Schneider, supra; Tesch et al. (1999) *J. Exp. Med.* 190). Examples of animal models which can be used for evaluating the therapeutic efficacy of antibodies or antigen-binding fragments of the invention for preventing or treating atherosclerosis include using mice deficient in apolipoprotein A, ApoE, and LDL $R_L$ (Dansky et al. (1999) *Arterioscler Thromb. Vasc. Biol.* 19:1960-1968; Lou et al. (1998) *PNAS* 95:12591-12595). Examples of animal models which can be used for evaluating the therapeutic efficacy of antibodies or antigen-binding fragments of the invention for preventing or treating inflammatory bowel disease (IBD) include TNBS-induced IBD, DSS-induced IBD, and (Padol et al. (2000) *Eur. J. Gastrolenterol Hepatol* 12:257; Murthy et al. (1993) *Dig. Dis. Sci.* 38:1722). Examples of animal models which can be used for evaluating the therapeutic efficacy of antibodies or antigen-binding fragments of the invention for preventing or treating rheumatoid arthritis (RA) include adjuvant-induced RA, collagen-induced RA, and collagen mAb-induced RA (Holmdahl et al., (2001) *Immunol. Rev.* 184:184; Holmdahl et al., (2002) *Ageing Res. Rev.* 1:135; Van den Berg (2002) *Curr. Rheumatol. Rep.* 4:232).

In addition, animal models for evaluating the efficacy of antibodies or antigen-binding fragments of the invention in treating or preventing human fibrotic diseases, include rodent models of pulmonary (Brieland et al. (1992) *Am. J. Respir. Cell. Mol. Biol.* 7:134-139; Zhang et al. (1994) *J. Immunol.* 153:4733-4741; Johnston et al. (1998) *Exp. Lung Res.* 24:321-337), vascular (Furukawa et al. (1999) *Circ. Res.* 84:306-314), and renal (Lloyd et al. (1997) *J. Exp. Med.* 185:1371-1380; Fujinaka et al. (1997) *J. Am. Soc. Nephrol.* 8:1174-1178; Schneider, supra; Tesch et al. (1999) *J. Exp. Med.* 190: 1813-1824; Tesch et al. (1999) *J. Clin. Invest.* 103:73-80) fibrosis. Alport's model of renal fibrosis can also be used to evaluate the efficacy of the antibodies or antigen-binding fragments of the invention.

C. Treatment Regimes and Dosages

In prophylactic applications, pharmaceutical compositions or medicaments are administered to a subject suffering from a disorder in which MCP activity is detrimental, in an amount sufficient to eliminate or reduce the risk, lessen the severity, or delay the outset of the disorder, including biochemical, histologic and/or behavioral symptoms of the disorder, its complications and intermediate pathological phenotypes presenting during development of the disorder. In therapeutic applications, compositions or medicants are administered to a subject suspected of, or already suffering from such a disorder in an amount sufficient to cure, or at least partially arrest, the symptoms of the disorder (biochemical, histologic and/or behavioral), including its complications and intermediate pathological phenotypes in development of the disorder.

In some methods, administration of agent reduces or eliminates inflammation associated with MCPs. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Such a response can be an active response, i.e., induced by administration of immunogen, or a passive response, i.e., induced by administration of immunoglobulin or antibody or primed T-cells.

An "immunogenic agent" or "immunogen" is capable of inducing an immunological response against itself on administration to a mammal, optionally in conjunction with an adjuvant. Typically, the immune response is monitored and repeated dosages are given if the immune response starts to wane.

Effective doses of the compositions of the present invention, for the treatment of the above described conditions vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated. Treatment dosages need to be titrated to optimize safety and efficacy.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg, preferably at least 1 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. Intervals can also be irregular as indicated by measuring blood levels of antibody to MCPs in the subject. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the subject. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, compositions containing the present antibodies or a cocktail thereof are administered to a subject not already in the disease state to enhance the subject's resistance. Such an amount is defined to be a "prophylactic effective dose." In this use, the precise amounts again depend upon the subject's state of health and general immunity, but generally range from 0.1 to 25 mg per dose, especially 0.5 to 2.5 mg per dose. A relatively low dosage is administered at relatively infrequent intervals over a long period of time. Some subjects continue to receive treatment for the rest of their lives.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the subject shows partial or complete amelioration of symptoms of disease. Thereafter, the patent can be administered a prophylactic regime.

Doses for nucleic acids encoding antibodies range from about 10 ng to 1 g, 100 ng to 100 mg, 1 µg to 10 mg, or 30-300 µg DNA per subject. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of MCP-associated disorders.

D. Pharmaceutical Compositions

The therapeutic compositions of the invention include at least one antibody or antibody fragment of the invention in a pharmaceutically acceptable carrier. A "pharmaceutically acceptable carrier" refers to at least one component of a pharmaceutical preparation that is normally used for administration of active ingredients. As such, a carrier may contain any pharmaceutical excipient used in the art and any form of vehicle for administration. The compositions may be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249: 1527 (1990) and Hanes, *Advanced Drug Delivery Reviews* 28:97 (1997)). The agents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25:3521 (1995); Cevc et al., *Biochem. Biophys. Acta* 1368:201-15 (1998)).

III. Monitoring the Course of Treatment

The invention provides methods of monitoring treatment in a subject suffering from a disorder in which MCP activity is detrimental, i.e., for monitoring a course of treatment being administered to a subject. The methods can be used to monitor both therapeutic treatment on symptomatic subjects and prophylactic treatment on asymptomatic subjects. In particular, the methods are useful for monitoring passive immunization (e.g., measuring level of administered antibody).

Some methods entail deter mining a baseline value, for example, of an antibody level or profile in a subject, before administering a dosage of agent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

In other methods, a control value (i.e., a mean and standard deviation) of level or profile is determined for a control population. Typically the individuals in the control population have not received prior treatment. Measured values of the level or profile in a subject after administering a therapeutic agent are then compared with the control value. A significant increase relative to the control value (e.g., greater than one standard deviation from the mean) signals a positive or sufficient treatment outcome. A lack of significant increase or a decrease signals a negative or insufficient treatment outcome. Administration of agent is generally continued while the level is increasing relative to the control value. As before, attainment of a plateau relative to control values is an indicator that the administration of treatment can be discontinued or reduced in dosage and/or frequency.

In other methods, a control value of the level or profile (e.g. a mean and standard deviation) is determined from a control population of individuals who have undergone treatment with a therapeutic agent and whose levels or profiles have plateaued in response to treatment. Measured values of levels or profiles in a subject are compared with the control value. If the measured level in a subject is not significantly different (e.g., more than one standard deviation) from the control value, treatment can be discontinued. If the level in a subject is significantly below the control value, continued administration of agent is warranted. If the level in the subject persists below the control value, then a change in treatment may be indicated.

In other methods, a subject who is not presently receiving treatment but has undergone a previous course of treatment is monitored for antibody levels or profiles to determine whether a resumption of treatment is required. The measured level or profile in the subject can be compared with a value previously achieved in the subject after a previous course of treatment. A significant decrease relative to the previous measurement (i.e., greater than a typical margin of error in repeat measurements of the same sample) is an indication that treatment can be resumed. Alternatively, the value measured in a subject can be compared with a control value (mean plus standard deviation) determined in a population of subjects after undergoing a course of treatment. Alternatively, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level (i.e., more than a standard deviation) is an indicator that treatment should be resumed in a subject.

The tissue sample for analysis is typically blood, plasma, serum, mucous fluid or cerebrospinal fluid from the subject. The sample is analyzed, for example, for levels or profiles of antibodies to Aβ peptide, e.g., levels or profiles of humanized antibodies. ELISA methods of detecting antibodies specific to MCPs are described in the Examples section.

The antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to MCPs in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one standard deviation of the reference value in population of subjects benefiting from treatment) administration of an additional dosage of antibody is indicated.

Additional methods include monitoring, over the course of treatment, any art-recognized physiologic symptom (e.g., physical or mental symptom) routinely relied on by researchers or physicians to diagnose or monitor disorders associated with detrimental MCP activity.

The invention further provides kits for performing the monitoring methods described above. Typically, such kits contain an agent that specifically binds to antibodies to MCPs, including MCP-1, MCP-2, and/or MCP-3. The kit can also include a label. For detection of antibodies to MCPs, the label is typically in the form of labeled anti-idiotypic antibodies. For detection of antibodies, the agent can be supplied prebound to a solid phase, such as to the wells of a microtiter dish. Kits also typically contain labeling providing directions for use of the kit. The labeling may also include a chart or other correspondence regime correlating levels of measured label with levels of antibodies to MCPs. The term labeling refers to any written or recorded material that is attached to, or otherwise accompanies a kit at any time during its manufacture, transport, sale or use. For example, the term labeling encompasses advertising leaflets and brochures, packaging materials, instructions, audio or videocassettes, computer discs, as well as writing imprinted directly on kits.

The invention also provides diagnostic kits, for example, research, detection and/or diagnostic kits (e.g., for performing in vivo imaging). Such kits typically contain an antibody for binding to an epitope of an MCP. Preferably, the antibody is labeled or a secondary labeling reagent is included in the kit. Preferably, the kit is labeled with instructions for performing the intended application, for example, for performing an in vivo imaging assay. Exemplary antibodies are those described herein.

This invention is further illustrated by the following examples which should not be construed as limiting. The contents of all references, patents and published patent applications cited throughout this application, as well as the figures and the Sequence Listing, are incorporated herein by reference.

EXAMPLES

I. Characterization of Anti-Chemokine Monoclonal Antibody Supernatants

Example 1

ELISA Screening

MaxiSorp 384 well plates were coated with 15-20 µl antigen in PBS. Recombinant purified human antigens included: MCP-1, MCP-2, MCP-3, MCP-4, IL-8, eotaxin, fractalkine, Gcp-2, DC-CK (Gcp-2 and DC-CK are also chemokines). Plates were incubated with antigen for 2 hours at 37° C. or overnight at 4° C. Non-specific sites were blocked with 80 µl/well of 1% BSA/PBS for 1 hour at room temperature. Plates were washed and 15 µl of hybridoma supernatant was added to each well and incubated for 1 hour at room temperature. Plates were washed and wells were incubated with 20 µl/well of a 1:25 000 dilution of goat anti-mouse IgG peroxidase conjugate (Jackson Catalog Number 515-036-003). Plates were incubated for 1 hour at room temperature, washed, and 20 µl/well of substrate (TMB, tetramethylbenzidine, Jackson, Catalog Number 515-036-062) was added. Reaction was allowed to proceed and stopped by addition of 20 µl/well of 2M $H_2SO_4$. Reactive clones were picked for further analysis. Isotyping of hybridoma supernatants was performed by antigen-dependent ELISA. Briefly, wells were coated with 50 µl of human MCP-1 (5 µg/ml) for 1 hour at 37° C. Wells were washed 4 times and blocked with PBS/1% BSA. Isotyping of hybridoma supernatants was then performed using a mouse immunoglobulin screening/isotyping kit (Zymed Laboratories, San Francisco, Calif.) as recommended by the manufacturer. Specificities of the antibodies and clones obtained are shown in Table 1.

In addition, both 1A1 and 11K2 mAbs recognize primate MCP-1. Plates were coated with 1 µg/ml of chemically synthesized chemokines (corresponding to the cynomolgus and rhesus MCP-1 sequences) and probed with 10 µg/ml of monoclonal antibodies, including MOPC21 (IgG1b control antisera), 11K2, 3N10, 1A1, D9, and 1M11, as described above. Results demonstrate that all of the above mAbs, including 1A1 and 11K2, and with the exception of the isotype control mAb MOPC21, also recognize primate MCP-1.

Example 2

Binding Assay $^{125}$I labeled MCP-1 (2200 Ci/mmol) was purchased from NEN Life Sciences (Boston, Mass.). Hybridoma supernatants (50 µl) were pre-incubated with 1 nM $^{125}$I MCP-1 (50 µl) for 60 minutes at room temperature prior to the addition of the CCR2-expressing human monocyte cell line, THP-1. THP-1 cells ($1 \times 10^7$ cells/ml; 50 µl) were resuspended in binding buffer (50 mM Hepes, 1 mM $CaCl_2$, 5 mM $MgCl_2$, 0.5% BSA) and added to the combination of $^{125}$I labeled MCP-1 and hybridoma supernatant, and incubated at 4° C. for 60 minutes. Cells were then washed 3 times by centrifugation in wash buffer (50 mM Hepes, 1 mM $CaCl_2$, 5 mM $MgCl_2$, 500 mM NaCl and 0.5% BSA). Amount of bound $^{125}$I labeled MCP-1 was then quantitated for γ-remission. Pre-incubation of THP-1 cells ($1 \times 10^7$ cells/ml; 50 µl) with unlabeled MCP-1 (500 nM; 50 µl) for 60 minutes at 4° C. prior to addition of $^{125}$I labeled MCP-1 (1 nM; 50 µl) served as a negative control. The positive control represents binding of $^{125}$I labeled MCP-1 to THP-1 cells in the absence of MCP-1 hybridoma supernatant. The results are shown in Table 2.

TABLE 3

Panel of MCP mAbs

| Fusion | Immunogen | Clone | Specificity | | | | Affinity (Biacore) | Sub-Type | Block MCP-1 ligand binding |
| | | | MCP-1 | MCP-2 | MCP-3 | MCP-4/IL-8/ Eotaxin/Frac Gcp-2/DC-CK | | | |
|---|---|---|---|---|---|---|---|---|---|
| IA1 | MCP-1 | 1M-11 | ++++ | − | − | − | ++++ | IgG1 | ++++ |
|  |  | 3N10 | ++++ | − | − | − | ++++ | IgG1 | ++++ |
| IA7 | MCP-1 | 11K2 | ++++ | ++++ | ++++ | − | ++++ | IgG1 | ++++ |
|  | MCP-2 | 7F7 | ++++ | − | − | − | ++++ | IgG1 | +++ |
|  | MCP-3 | 6D21 | ++++ | ++++ | ++ | − | ++++ | IgG1 | ++++ |
|  |  | 6E11 | ++ | − | + | − | +++ | IgG1 | +++ |
|  |  | 1A1 | +++ | + | + | − | ++++ | IgG1 | ++++ |
| IA8 | MCP-1 | 4N4 | ++++ | ++ | ++ | − | ++++ | IgG1 | ++++ |
|  | MCP-2 | 5A13 | +++ | ++ | ++ | − | +++ | IgG1 | ++++ |
| IA9 | MCP-1 | 5J23 | ++++ | ++ | − | − | ++++ | IgG1 | ++++ |
|  | MCP-2 | 6I5 | ++++ | +++ | +++ | − | ++++ | IgG1 | ++++ |
|  | MCP-3 | 7H1 | ++++ | ++++ | ++++ | − | ++++ | IgG1 | ++++ |
| IA10 | MCP-1 | 4N9 | + | − | ++ | − | ++++ | IgG1 | +++ |
|  | MCP-2 | 2O24 | ++ | − | ++ | − | ++++ | IgG1 | +++ |
|  | MCP-3 | 9H23 | ++ | − | + | − | +++ | IgG1 | +++ |
|  |  | 9B11 | ++++ | − | ++++ | − | ++++ | IgG1 | +++ |
|  |  | 9B12 | + | − | +++ | − | ++++ | IgG1 | +++ |
|  |  | 9C11 | ++++ | − | ++++ | − | ++++ | IgG1 | +++ |
|  |  | 10D18 | ++++ | − | ++++ | − | ++++ | IgG1 | ++++ |
|  |  | 12F15 | +++ | − | +++ | − | ++++ | IgG1 | ++++ |
|  | MCP-1 | D9 | ++++ | − | − | − (MCP-4, IL-8 and eotaxin only tested) |  |  | +++ |

+ and − indicate the relative amount of binding of the antibody to the various immobilized ligands.

TABLE 4

Data of block ligand ([I$^{125}$] MCP-1) binding assay from γ Counter

| Fusion | Immunogen | Clone # | CPM (30/10/00) | | CPM (22/11/00) | |
|---|---|---|---|---|---|---|
| IA1 | MCP-1 | 1M-11 | 499 | 456 | 45 | 40 |
|  |  | 3N10 | 379 | 495 | 50 | 46 |
| IA7 | MCP-1 | 11K2 | 103 | 148 | 50 | 49 |
|  | MCP-2 | 7F7 | 394 | 199 | 189 | 197 |
|  | MCP-3 | 6D21 | 145 | 108 | 47 | 42 |
|  |  | 6E11 | 850 | 894 | 378 | 323 |
|  |  | 1A1 | 194 | 772 | 47 | 52 |
| IA8 | MCP-1 | 4N4 |  |  | 40 | 47 |
|  | MCP-2 | 5A13 |  |  | 50 | 44 |
| IA9 | MCP-1 | 5J23 | 478 | 280 | 59 | 47 |
|  | MCP-2 | 6I5 | 677 | 678 | 44 | 31 |
|  | MCP-3 | 7H1 | 53 | 207 | 59 | 77 |
| IA10 | MCP-1 | 4N9 | 776 | 987 | 306 | 340 |
|  | MCP-2 | 2O24 | 936 | 869 | 226 | 357 |
|  | MCP-3 | 9H23 |  |  | 293 | 226 |
|  |  | 9B11 | 679 | 892 | 238 | 201 |
|  |  | 9B12 | 834 | 657 | 304 | 265 |
|  |  | 9C11 | 605 | 512 | 241 | 252 |
|  |  | 10D18 | 485 | 444 | 174 | 310 |
|  |  | 12F15 | 421 | 344 | 281 | 213 |
|  |  | 12K14 |  |  | 406 | 918 |
| Negative control |  |  | 836 | 461 | 68 | 143 |
| Positive control |  |  | 5861 | 3447 | 2084 | 2933 |

Example 3

Inhibition of Chemotaxis in Response to MCP-1

A 5 μm pore size ChemoTX plate (Neuroprobe) was used to assess the chemotactic response of THP-1 human monocytic cells. Hybridoma supernatants containing MCP-1 at 10 ng/ml, or RPMI with 10% FBS with or without 10 ng/ml chemokine, was added to the lower chamber of the plate. THP-1 cells at 2×106 cells/ml were layered on top. The plate was incubated for 2 hours at 37° C. in 5% CO2. The filter was removed and the number of cells that migrated into the lower chamber was determined using Promega Cell Titer reagent. The number of cells was calculated using a standard curve (n=4, error bars=standard deviation). The results demonstrated that antibodies 11K2, 7F7, 6D21 and 7H1 were all able to inhibit MCP-1-induced chemotaxis, although 11K2 and 6D21 were the most effective.

II. Characterization of Purified Anti-Chemokine Monoclonal Antibodies

Example 4

Chemokine Specificity and Binding Assays

ELISA specificity assays were performed using purified monoclonal antibodies to confirm the binding specificities of the supernatant MCP-specific monoclonal antibodies described above. Antibodies were purified by Protein A affinity column chromatography, according to standard methods known in the art.

ELISA was performed as previously described in Example 1. Briefly, MaxiSorp 384 well plates were coated with 15-20 μl antigen in PBS. Recombinant purified human antigens included: MCP-1, MCP-2, MCP-3, MCP-4, IL-8, eotaxin, murine MCP-1 (JE), murine MCP-3, murine MCP-5, and rat MCP-1. All antigens, including MCP-3, were immobilized. Plates were washed and purified monoclonal antibody (10 μg/ml) was added to each well and incubated for 1 hour at room temperature. Plates were washed and wells were incubated with 20 μl/well of a 1:25,000 dilution of goat anti-mouse IgG peroxidase conjugate (Jackson Catalog Number 515-036-003). Plates were incubated for 1 hour at room temperature, washed, and 20 μl/well of substrate (, tetramethylbenzidine, Jackson, Catalog Number 515-036-062) was added. Reaction was allowed to proceed and stopped by addition of 20 μl/well of 2M $H_2SO_4$. Specificities of the purified antibodies and are shown in Table 3. Antibodies 1A1 bound specifically to hMCP-1, hMCP-2, hMCP-3, and mMCP-1. Antibodies 11K2, 4N4, 5A13, 6D21, 6I5, and 7H1 bound specifically to hMCP-1, hMCP-2, hMCP-3, mMCP-1, mMCP-3, and mMCP-5.

TABLE 5

ELISA performed using purified MCP mAbs.

|  | hMCP-1 | hMCP-2 | hMCP-3 | hMCP-4 | mMCP-1 (JE) | mMCP-3 | mMCP-5 | rtMCP-1 | hIL8 | hEotaxin |
|---|---|---|---|---|---|---|---|---|---|---|
| 1A1 | + | + | + | − | + | − | − | − | − | − |
| 4N4 | + | + | + | − | + | + | + | − | − | − |
| 5A13 | + | + | + | − | + | + | + | − | − | − |
| 6D21 | + | + | + | − | + | + | + | − | − | − |
| 6I5 | + | + | + | − | + | + | + | − | − | − |
| 7H1 | + | + | + | − | + | + | + | − | − | − |
| 11K2 | + | + | + | − | + | + | + | − | − | − |
| D9 | + | − | − | − | − | − | − | − | − | − |
| 1M11 | + | − | − | − | − | ND | ND | ND | ND | ND |
| 3N10 | + | − | − | − | − | ND | ND | ND | ND | ND |
| 2O24 | + | − | + | − | − | ND | ND | ND | ND | ND |
| 9B11 | + | − | + | − | − | ND | ND | ND | ND | ND |
| 9B12 | + | − | + | − | − | ND | ND | ND | ND | ND |
| 9C11 | + | − | + | − | − | ND | ND | ND | ND | ND |
| 5J23 | + | + | +/− | − | + | ND | ND | − | − | − |

Binding assays were performed using purified monoclonal antibodies to confirm results obtained with the supernatants. Binding assays were performed as described in Example 2. Briefly, $^{125}$I labeled MCP-1 (2200 Ci/mol) was purchased from NEN Life Sciences (Boston, Mass.). Purified monoclonal antibodies at various concentrations (33 nM, 3.3 nM and 0.33 nM) were pre-incubated with 1 nM $^{125}$I MCP-1 (50 μl) for 60 minutes at room temperature prior to addition of the CCR2-expressing human monocyte cell line, THP-1. THP-1 cells ($1 \times 10^7$ cells/ml; 50 µl) were resuspended in binding buffer (50 mM Hepes, 1 mM $CaCl_2$, 5 mM $MgCl_2$, 0.5% BSA) and added to the combination of $^{125}I$ labeled MCP-1 and purified mAb, and incubated at 4° C. for 60 minutes. Cells were then washed 3 times by centrifugation in wash buffer (50 mM Hepes, 1 mM $CaCl_2$, 5 mM $MgCl_2$, 500 mM NaCl, and 0.5% BSA). Amount of bound $^{125}I$ labeled MCP-1 was then quantitated for γ-emission. Results from the binding assays are shown in Table 4. This study demonstrates that many of the studied monoclonal antibodies, including 1A1 and 11K2, were effective at blocking hMCP-1 binding.

TABLE 6

Purified mAb binding assay

| Antibody | Block hMCP-1 cell binding |
| --- | --- |
| 1A1 | + |
| 4N4 | + |
| 5A13 | + |
| 6D21 | + |
| 6I5 | + |
| 7H1 | + |
| 11K2 | + |
| D9 | + |
| 1M11 | + |
| 3N10 | + |
| 2O24 | − |
| 9B11 | − |
| 9B12 | − |
| 9C11 | − |
| 5J23 | + |

Example 5

Inhibition of Monocyte Chemotaxis by Anti-Chemokine Monoclonal Antibodies

A. MCP-1 and MCP-2 Chemotaxis Assay

A 5 µm pore size ChemoTX plate (Neuroprobe) was used to assess the chemotactic response of TIP-1 human monocytic cells. Purified monoclonal antibodies (100 µg/ml) 11K2, 1A1, D9, and 2O24 were added in combination with and without MCP-1 (2.3 nM), MCP-2 (56 nM), and MCP-1/MCP-2 (2.3 nM MCP-1 and 56 nM MCP-2), to the lower chamber of the plate. THP-1 cells at $2 \times 10^6$ cells/ml were layered on top. The plate was incubated for 4 hours at 37° C. in 5% $CO_2$. The filter was removed and the number of cells that migrated into the lower chamber was determined using Promega Cell Titer reagent.

Figure 2A:
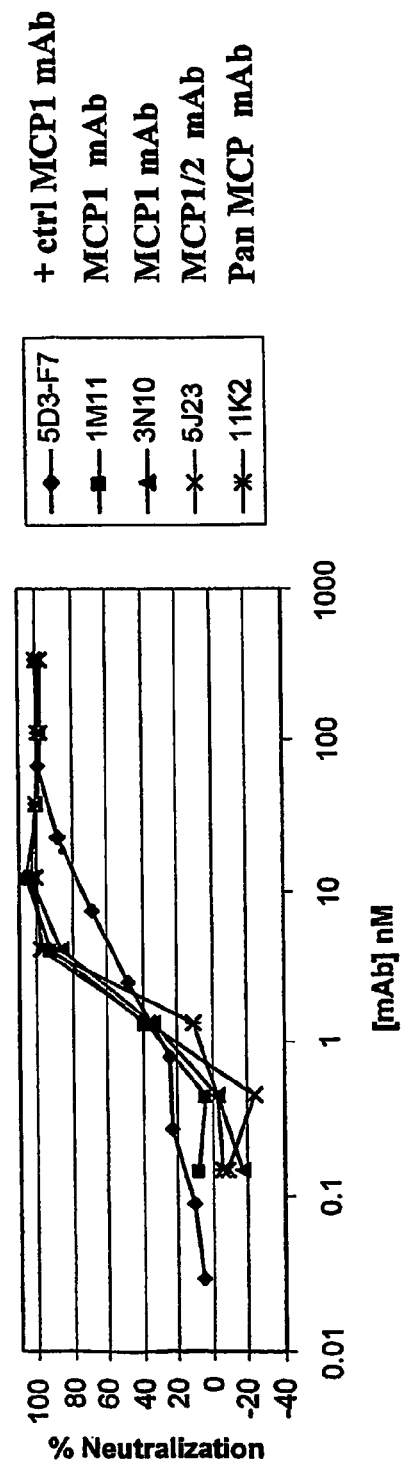
FIG. 2A graphically depicts results using monoclonal antibodies 5D3-F7 (BD Biosciences, Pharmingen, San Diego, Calif.), 1M11, 3N10, 5J23, and 11K2 in response to 20 ng/mL of MCP-1.
Figure 2B:
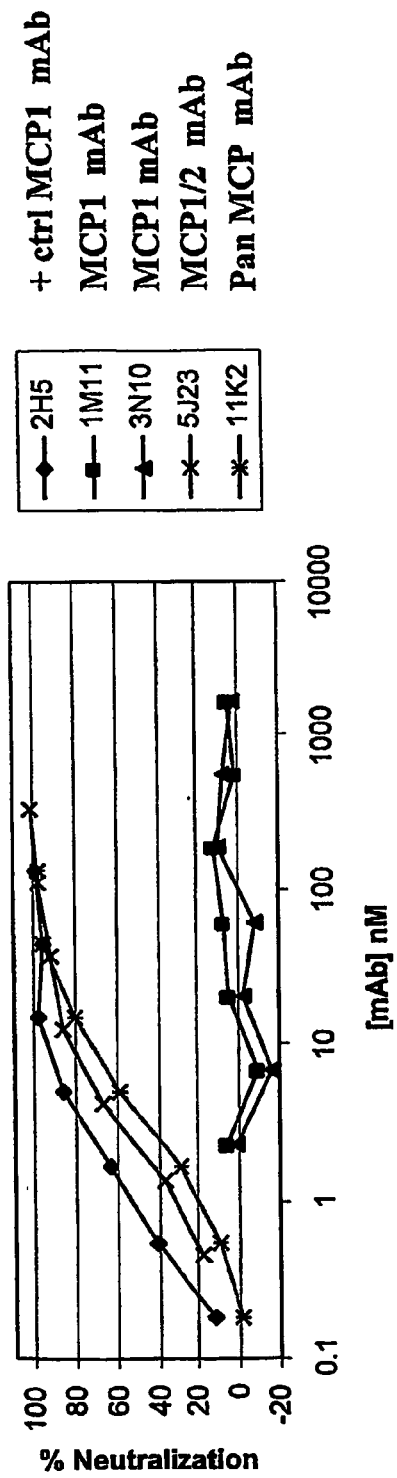
FIG. 2B graphically, depicts results using 20 ng/mL of murine MCP-1 (JE) and monoclonal antibodies 2H5 (BD Biosciences, Pharmingen, San Diego, Calif.), 1M11, 3N10, 5J23, and 11K2.

The results show that pan-monoclonal antibodies 11K2 and 1A1 were effective at inhibiting chemotaxis in the presence of both MCP1 and MCP-2 (FIG. 1). The results also demonstrate that antibodies D9 and 2O24 can inhibit chemotaxis which is induced by MCP-1 alone. Furthermore, as shown in FIG. 2, antibodies 1M11 and 3N10 can inhibit THP-1 chemotaxis induced by human MCP-1, and antibody 5J23 can inhibit chemotaxis induced by human and mouse MCP-1. In sum, chemotaxis to the combination of MCP-1 and MCP-2 is inhibited by 11K2 and 1A1, but is not observed by antibodies D9 and 2O24, which are MCP-1-specific mAb (D9 and 2O24).

Within the pool of monoclonal antibodies studied, there are three groups which arise based on their ability to recognize certain MCP antigens. Monoclonal antibodies 1A1 and 11K2 recognize MCP-1, MCP-2 and immobilized MCP-3. Monoclonal antibodies 1M11 and 3N10 recognize MCP-1, and antibody 2O24 recognizes MCP-1 and MCP-3. Antibody 5J23 recognizes mouse MCP-1 and recognizes only human MCP-1 and human MCP-2.

Results from a separate experiment using the ChemoTX plate (Neuroprobe) assay are shown below in Table 5. The protocol for this experiment was the same as previously described, except a titration of mAb was used in combination with fixed MCP concentrations (concentrations of MCPs are shown below in Table 5). The results described in Table 5 demonstrate that mAbs 11K2 and 1A1 are effective at inhibiting huMCP-1, huMCP-2, muMCP-1, and muMCP-5-induced chemotaxis.

TABLE 7

11K2 and 1A1 inhibit THP-1 chemotaxis towards human MCP-1, human MCP-2, mouse MCP-1 and mouse MCP-5

| | Human | | | |
| --- | --- | --- | --- | --- |
| $ND_{50}$ (nM) | MCP-1(2.3 nM) | MCP-2(56 nM) | MCP-3(11.8 nM) | MCP-4(58 nM) |
| Commercial | 10.0 | 33.0 | 2.6 | 11.5 |
| 1A1 | 1.4 | 47.5 | No Inhib | No Inhib |
| 11K2 | 1.3 | 52.0 | No Inhib | No Inhib |
| D9 | 5.8 | No Inhib | No Inhib | No Inhib |
| 2O24 | 1000.0 | No Inhib | 143.5 | No Inhib |

| | Murine | | | |
| --- | --- | --- | --- | --- |
| $ND_{50}$ (nM) | MCP-1(1.4 nM) | MCP-2 | MCP-3(59 nM) | MCP-4 | MCP-5(0.54 nM) |
| Commercial | 3.2 | ND | 52.0 | ND | 0.1 |
| 1A1 | 1.7 | ND | No Inhib | ND | 13.5 |
| 11K2 | 2.1 | ND | No Inhib | ND | 19.5 |
| D9 | No Inhib | ND | No Inhib | ND | No Inhib |
| 2O24 | No Inhib | ND | No Inhib | ND | No Inhib |

No Inhib = less than 50% Neutralization at 3 uM

B. Inhibition of Chemotaxis by Cytokines Secreted from RA Fibroblasts

Prior to studying the ability of purified monoclonal antibodies 1A1, 11K2, D9, 2O24, and 5D3-F7 (BD Biosciences, Pharmingen, San Diego, Calif.), to inhibit chemotaxis from chemokines secreted from stimulated RA fibroblasts, a study of the different types of chemokines secreted by RA (rheumatoid arthritis) fibroblasts in response to inflammatory chemokines was performed. RA fibroblasts were exposed for 48 hours to 500 U/ml IFN-γ, IFN-γ and 10 ng/ml of IL1β, or media (as a control). Results showed that IFN-γ alone induced low levels of MCP-1, MCP-2, MCP-3, and very low levels of IP10. IFN-γ exposure alone did not induce expression of Rantes, IL-8, Mip1α, or Mip1β. In contrast, the combination of IFN-γ and 10 ng/ml of IL1β induced about 27 ng/ml of MCP-1, 31 ng/ml of MCP-2, 9 ng/ml of MCP-3, and 55 ng/ml of IL-8. The combination of IFN-γ and 10 ng/ml of IL1β also yielded low levels of Rantes, IP10, and Mip1α. The media alone control did not induce any chemokine secretion.

Figure 3:
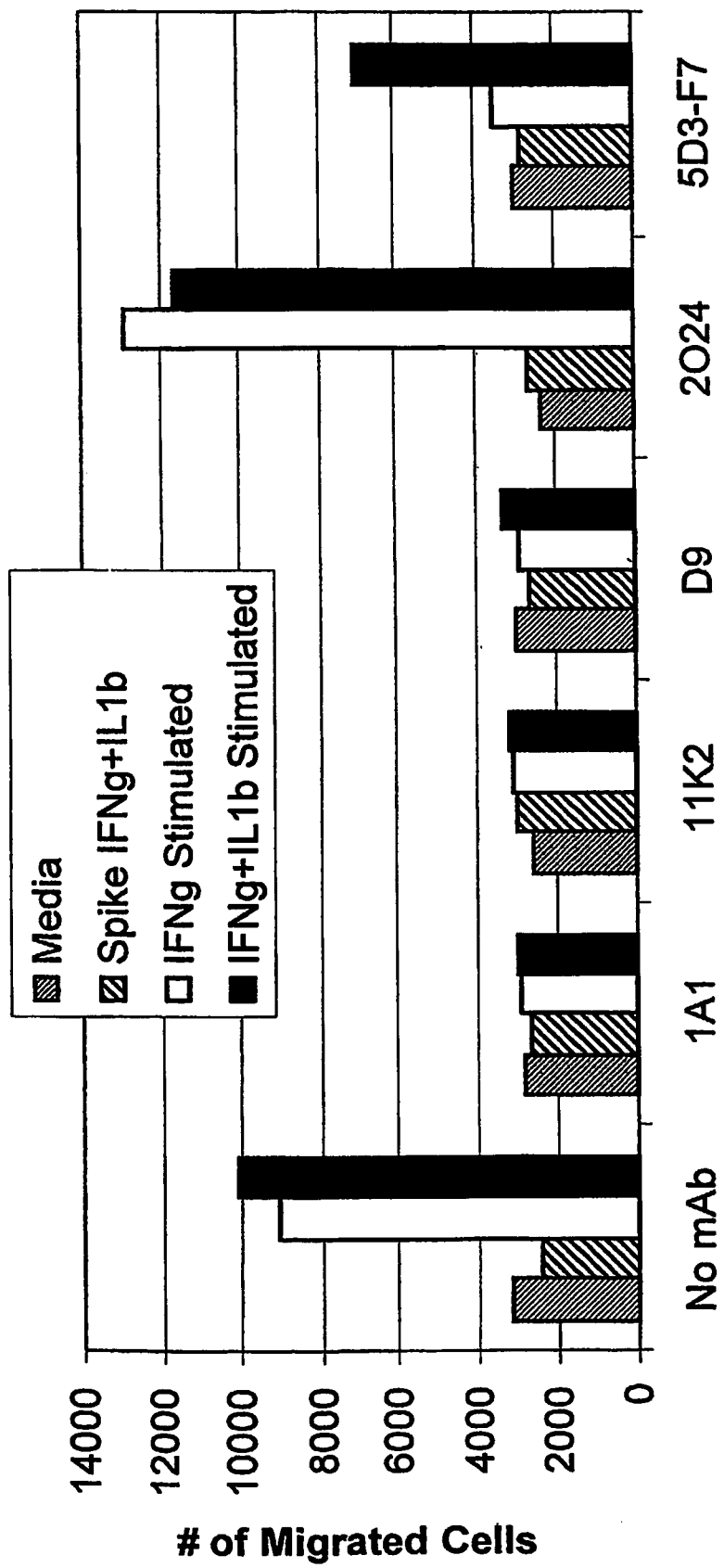
FIG. 3 graphically depicts results of a chemotaxis assay which demonstrates that monocyte chemotaxis mediated by cytokines secreted from stimulated rheumatoid arthritis (RA) fibroblasts is inhibited by pan-MCP mAbs (1A1 and 11K2) and MCP-1 mAb D9.

The ability of purified monoclonal antibodies to inhibit monocyte chemotaxis to cytokines secreted from these stimulated RA fibroblasts was then studied. Supernatant from RA fibroblasts which were exposed to either media alone, IFN-γ alone, or the combination of IFN-γ and IL-1β, were each tested for their chemotactic ability using human THP-1 cells. As a control, supernatant from unstimulated RA fibroblasts into which IFN-γ (500 U/ml) and IL1β (10 ng/ml) was spiked was used. This supernatant (spike) control was used to evaluate the direct effects of IL1β and IFN-γ on chemotaxis. As shown in FIG. 3, monocyte chemotaxis mediated by cytokines secreted from stimulated RA fibroblasts was inhibited by MCP mAbs 1A1 and 11K2. MCP-1-specific antibody D9 was also effective at inhibiting chemotaxis in all experimental groups.

Example 6

MCP-1-Induced Calcium Flux Assay for Monoclonal 11K2

Figure 4A:
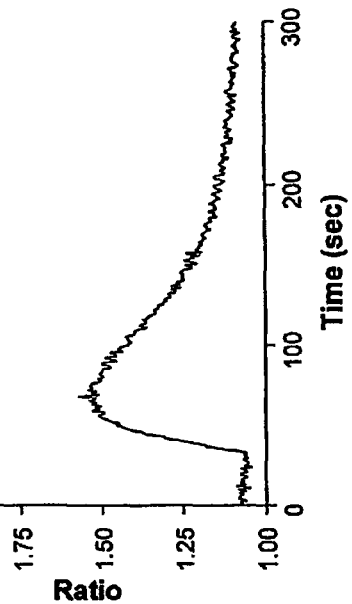
FIG. 4 graphically depicts results from a calcium flux assay using 11K2 (mAb and Fab fragments thereof) at various concentrations, including none (FIG. 4A), 20 nM mAb (FIG. 4B), and 60 nM Fab (FIG. 4C).
Figure 4B:
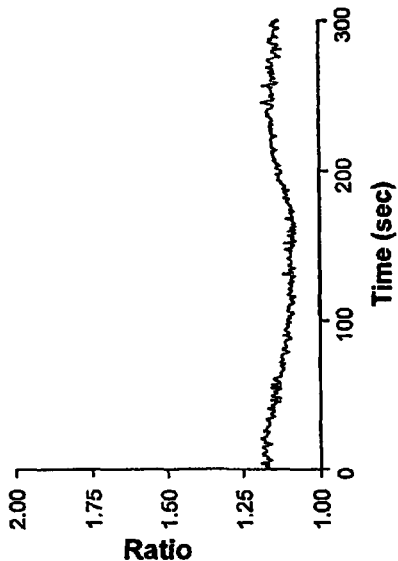
Figure 4C:
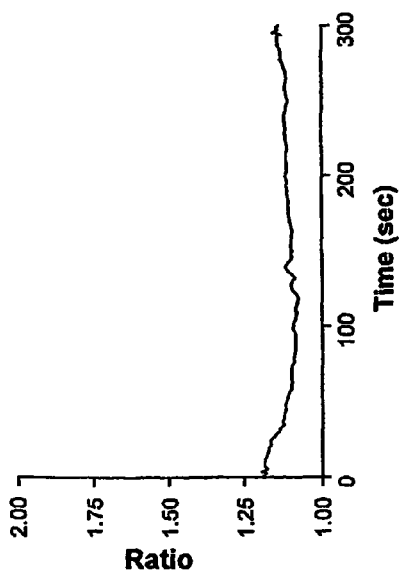

The MCP-1-induced calcium flux assay was performed according to standard procedure. Briefly, monoclonal antibody 11K2 and a chemokine (MCP-1 or MCP-2) were mixed at 200× concentration and pre-incubated for one hour. This mixture was then added to THP-1 cells sting in a cuvette in a fluorimeter at t=30 see. Calcium flux was measured by a change in fluorescence of Indo-1. Results show that MCP-1-induced calcium flux in THP-1 cells was blocked by 11K2 (FIG. 4).

Example 7

Agonist Effect at Low Antibody Concentrations of 11K2 and 1A1

A. Chemotaxis Assay

Figure 5A:
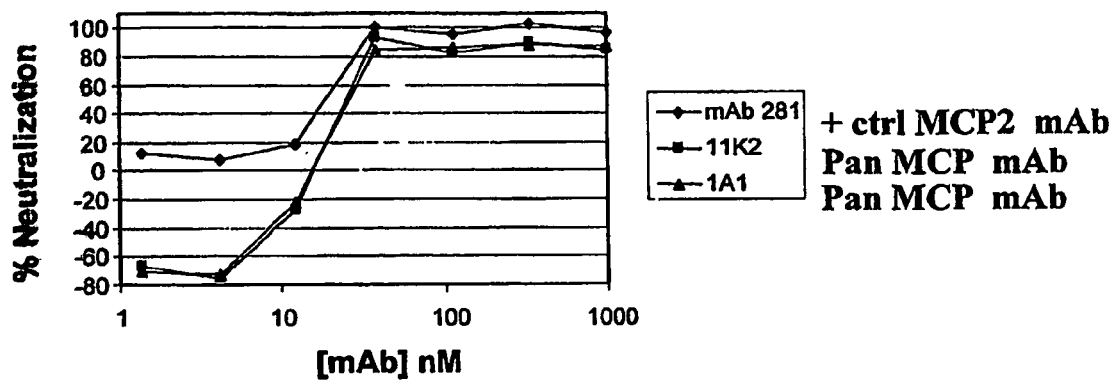
FIG. 5 graphically depicts results from a chemotaxis assay using pan-MCP antibodies demonstrating pan-MCP antibodies 11K2 and 1A1 increase MCP-2 mediated chemotaxis at low mAb concentrations (FIG. 5A). Blocking is also observed with MCP-2 mAb 281 (RD Systems, Minneapolis, N).
FIG. 5B graphically depicts a chemotaxis assay using the pan-MCP mAb 11K2 and the Fab fragment of 11K2.
Figure 5B:
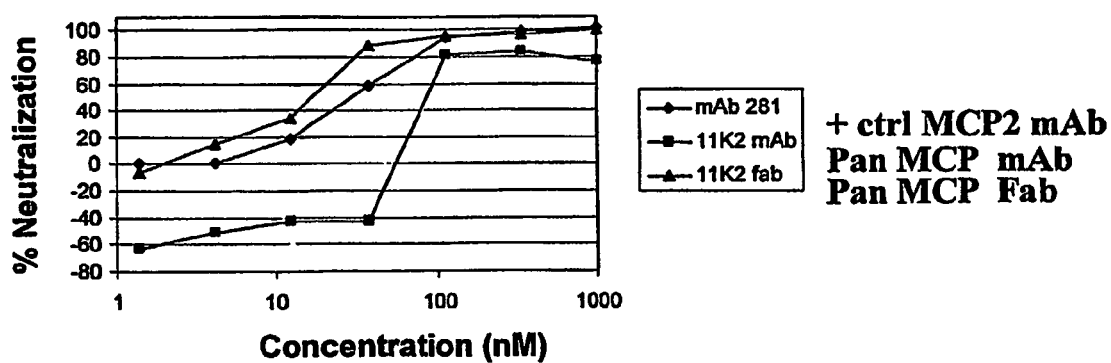
Figure 6A:
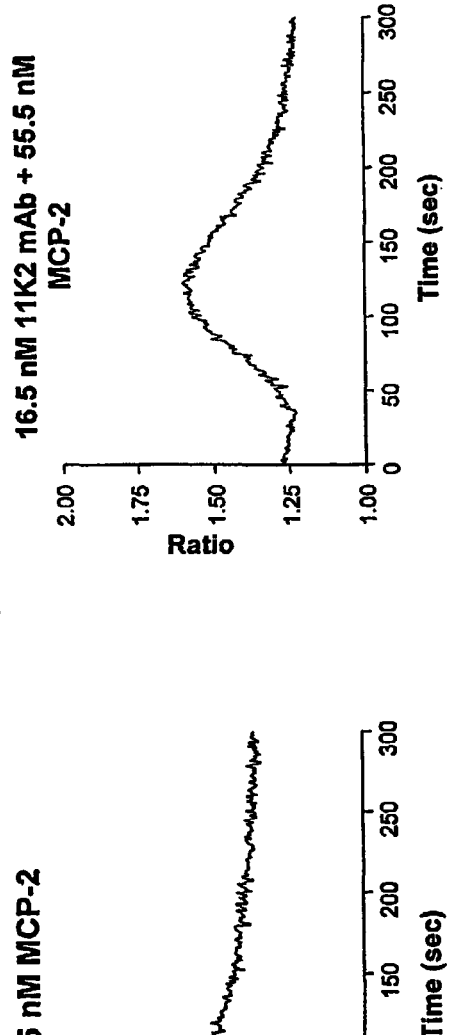
FIG. 6 graphically depicts results from a MCP-2 calcium flux assay which depicts results from 55.5 nM of MCP-2 alone, depicts results which demonstrate that the 11K2 monoclonal antibody shows agonistic activity (6B), and, as compared to 55.5 nM of MCP-2 alone (6A)
FIGS. 6C and 6D depict results which demonstrate that Fab and F(ab')2 fragments of 11K2 are inhibitory in this assay.
Figure 6B:
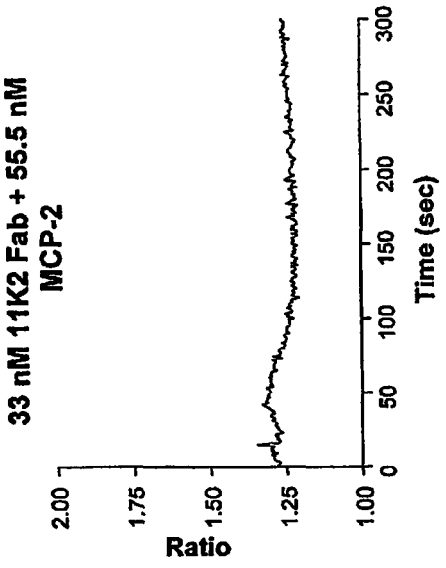
Figure 6C:
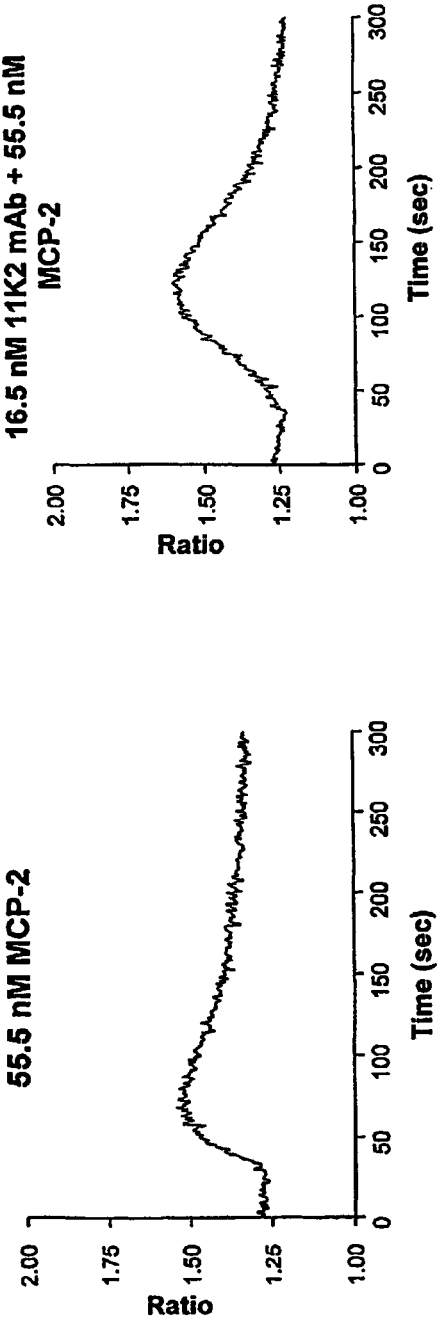
Figure 6D:
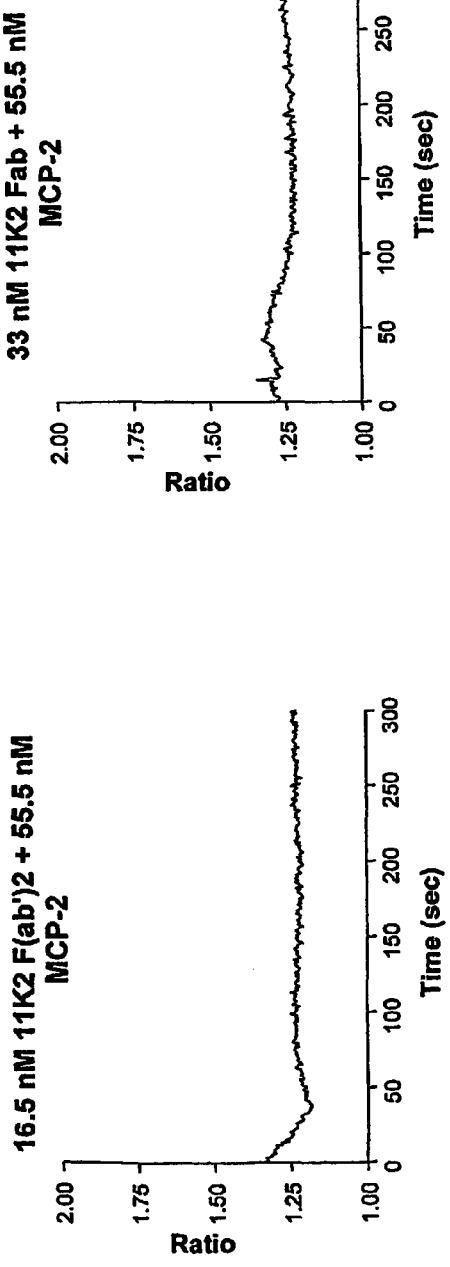

Chemotaxis assays were performed as previously described with recombinant MCP-2 and using low concentrations of monoclonal antibodies 11K2 and 1A1. The results from the chemotaxis assay showed that at a low concentration, monoclonal antibodies 11K2 and 1A1 increased MCP-2 mediated chemotaxis. As shown in FIG. 5A, there was an increase in chemotaxis observed with low antibody concentrations (ranging from about 1-15 nM) of 11K2 and 1A1, in contrast to the MCP-2 mAb 281 (RD Systems, Minneapolis, Minn.). The agonist effect was not seen with the Fab fragment of 11K2 or 1A1, and was MCP-2-specific. As shown in FIG. 5B, low concentrations of the 11K2 Fab fragment did not result in a chemotactic increase in response to MCP-2 and showed only antagonist activity.

B. Calcium Flux Assay

A calcium flux assay was performed as previously described, except a low concentration of 11K2 monoclonal antibody (16.5 nM) was also included. The results (FIG. 6) demonstrate that low concentrations of 11K2 exposure results in agonistic activity in a MCP-2 calcium flux assay. In addition, however, 11K2 Fab and F(ab)2 fragments are inhibitory in the same assay (FIG. 6).

Example 8

Binding Affinity Measurement of Monoclonal 11K2 and 1A1

To measure the affinity of MCP mAb and Fab molecules for soluble MCP molecules, a kinetic exclusion assay was utilized and affinity measured using a KinExA instrument (Sapidyne Instruments Inc., Boise, Id.).

Polymethylmethacrylate beads activated with NHS were coated with 10 μg recombinant human MCP-1 in 1 ml buffer. The beads were packed into a column in the KinExA instrument for each sample. This packed bead column is able to capture free MCP mAb or Fab flowed through the column. The amount of free mAb or Fab in solution was determined using a secondary goat anti-mouse heavy and light chain IgG-Cy5 conjugate.

A fixed amount of 11K2 mAb, 1A1 mAb, 11K2 Fab, or 1A1 Fab was incubated with various amounts of human MCP-1, MCP-2 or MCP-3 for three hours. The amount of uncomplexed free antibody remaining in solution was determined by flowing these mixtures over the MCP-1-loaded bead column and labeling with the Cy5 secondary antibody. The fluorescent signal was plotted against the MCP concentration and the affinity was determined using a quadratic curve fit Affinities determined for both 11K2 and 1A1 mAb and Fab molecules are listed in Table 6 below. Exact affinities of 11K2 mAb and 1A1 mAb for human MCP-1 could not be determined, as the affinity is much lower than the lowest amount of antibody that can be detected by this method. In those cases, only an upper limit to the affinity can be determined. Affinity of the 11K2 Fab and 1A1 Fab for human MCP-3 was not determined (ND).

TABLE 8

| MCP binding affinity measurements in solution | | | |
|---|---|---|---|
| Antibody | MCP-1 | MCP-2 | MCP-3 |
| 11K2 mAb | $<4 \times 10^{-13}$ M | $1.8 \times 10^{-11}$ M | $>5 \times 10^{-8}$ M |
| 11K2 Fab | $1.1 \times 10^{-11}$ M | $4.3 \times 10^{-10}$ M | ND |
| 1A1 mAb | $<7 \times 10^{-13}$ M | $1.2 \times 10^{-12}$ M | $>5 \times 10^{-8}$ M |
| 1A1 Fab | $1.3 \times 10^{-11}$ M | $3.2 \times 10^{-10}$ M | ND |

In sum, monoclonal antibodies 1A1 and 11K2 recognize soluble human MCP-1 and MCP-2 with a very high binding affinity which is in the low pM range. Both 1A1 and 11K2 also recognize mouse MCP-1, while neither recognizes soluble MCP-3.

III. Cloning and Sequencing of 1A1 and 11K2 Monoclonal Antibodies

Example 9

Cloning and Sequencing of mu1A1 Variable Regions

Mouse monoclonal antibody 1A1 was cloned and sequenced according to the following procedure. Total cellular RNA from 1A1 murine hybridoma cells was prepared using the Qiagen RNeasy mini kit according to the manufacturer's recommended protocol.

cDNAs encoding the 1A1 variable regions of the heavy and light chains were cloned by RT-PCR from total cellular RNA, following standard procedures known to one of skill in the art. Briefly, following the manufacturer's recommended protocols, first-strand cDNAs (prepared with the Amersham First-Strand cDNA Synthesis Kit) were amplified by PCR using the Clontech Advantage 2 PCR Kit. The following primers were used for first-strand synthesis of the 1A1 heavy and light chain cDNAs (Y=C/T, and R=A/G): 1A1 Heavy Chain cDNA Primer: 5'-AGG TCT AGA AYC TCC ACA CAC AGG RRC CAG TGG ATA GAC-3' (SEQ ID NO: 3) and 1A1 Light Chain cDNA Primer: 5'-GCG TCT AGA ACT GGA TGG TGG GAG ATG GA-3' (SEQ ID NO: 4).

Primers used for PCR amplification of the murine 1A1 immunoglobulin heavy chain variable domain were as follows: 5'-AGG TSM ARC TGC AGS AGT CWG G-3' (SEQ ID NO: 5) and 5'-TGA GGA GAC GGT GAC CGT GGT CCC TTG GCC CC-3' (SEQ ID NO: 6) (S=C/G, M=A/C, R=A/G, and W=A/T). The primers used for PCR amplification of the murine 1A1 immunoglobulin light chain variable domain were: 5'-GAY ATH CAR ATG ACN CAG-3' (SEQ ID NO: 7) and 5'-GCG TCT AGA ACT GGA TGG TGG GAG ATG GA-3' (SEQ ID NO: 8) (Y-=C/T, H=A/C/T, R=A/G, and N=A/C/G/T).

The PCR was performed at 30 cycles using Clontech's Advantage 2 PCR Kit using the following PCR conditions: denature 0.5 min at 94° C., anneal 1 min at 50° C., and elongate 1 min at 72° C. The PCR products were gel-purified using the Qiagen Qiaquick gel extraction kit following the manufacturer's recommended protocol. Purified 1A1 heavy and light chain PCR products were subcloned into Invitrogen's pCR2.1-TOPO vector using their TOPO TA Cloning kit according to the manufacturer's recommended protocol (pCR-049=1A1 heavy chain, pcr-053=1A1 light chain). Inserts from multiple independent subclones were sequenced according to methods known in the art and those described in Sanger et al., *PNAS* 74, 5463-5467, incorporated herein by reference, and subclones were found to be identical.

Sequence data was analyzed according to BLAST analysis (see http://www.ncbi.nlm.nih.gov). Blast analyses of the variable domain sequences confirmed their immunoglobulin identity. The 1A1 heavy chain variable domain was determined to be a member of murine subgroup II(C), while the 1A1 light chain variable region was determined to be a member of murine kappa subgroup II. The predicted amino acid sequences of the mature 1A1 murine variable domains, as well as the determined nucleotide sequences, are shown below in Tables 7 and 8.

TABLE 9

Nucleotide sequence of mu1A1 variable domains

1A1 Heavy Chain Variable Region (SEQ ID NO: 9)
```
  1 GAGGTCCAGCTGCAGCAGTCTGGGGCAGAACTTGTGAGGTCAGGGGCCTCAGTCAAGTTG  60
 61 TCCTGCACAGCTTCTGGCTTCAACATTAAAGACAACTATATGCACTGGGTGAAGCAGAGG 120
121 CCTGAACAGGGCCTGGAGTGGATTGGATGGATTGATCCTGAGAATGGAGATACTGAATAT 180
181 GCCCCGAAGTTCCAGGGCAAGGCCACTATGACTGCAGACACATCCTCCAACACAGCCTAC 240
241 CTGCAGCTCAGCAGCCTGACATCTGAGGACACTGCCGTCTATTACTGTAATACATGGGCT 300
301 TACTACGGTACTAGCTACGGGGGATTTGCTTACTGGGGCCAAGGGACCACGGTCACCGTC 360
361 TCCTCA                                                       366
```

1A1 Light Chain Variable Region (SEQ ID NO: 10)
```
  1 GATATCCAGATGACTCAGACTCCACTCACTTTGTCGGTTACCATTGGACAACCAGCCTCC  60
 61 ATCTCTTGCAAGTCAAGTCAGAGCCTCTTAGATAGTGATGGAAAGACATATTTGAATTGG 120
121 TCGTTACAGAGGCCAGGCCAGTCTCCAAAGCGCCTAATCTATCTGGTGTCTAAACTGGAC 180
181 TCTGGAGTCCCTGACAGGTTCACTGGCAGTGGATCAGGGACAGATTTCACACTGAAAATC 240
241 AGCAGAGTGGAGGCTGAGGATTTGGGAGTTTATTATTGCTGGCAAGGTACACATTTTCCT 300
301 CAGACGTTCGGTGGAGGCACCAAGCTGGAGATCAAA                         336
```

TABLE 10

Amino acid sequence of 1A1 variable domains
(CDR domains underlined)

1A1 Heavy Chain Variable Region (SEQ ID NO: 11)
EVQLQQSGAELVRSGASVKLSCTASGFNI<u>KDNYMH</u>WVKQRPEQGLEWIG<u>WIDPENGDTEYAPK</u>
                                  CDR1                          CDR2

<u>FQGK</u>ATMTADTSSNTAYLQLSSLTSEDTAVYYCNT<u>WAYYGTSYGGFAY</u>WGQGTTVTSS
                                    CDR3

TABLE 10-continued

Amino acid sequence of 1A1 variable domains
(CDR domains underlined)

1A1 Light Chain Variable Region (SEQ ID NO: 12)
DIQMTQTPLTLSVTIGQPASISC<u>KSSQSLLDSDGKTYLN</u>WSLQRPGQSPKRLIY<u>LVSKLDS</u>GV
                      CDR1                                  CDR2

PDRFTGSGSGTDFTLKISRVEAEDLGVYYC<u>WQGTHFPQT</u>FGGGTKLEIK
                               CDR3

Nucleotide and amino acid comparisons of the 1A1 variable heavy and light chains are also shown in FIG. 7. The sequence of the CDR regions of the 1A1 antibody were determined to be the following:

TABLE 11

CDRs of the 1A1 Antibody

1A1 Heavy Chain Variable Region

| | | |
|---|---|---|
| CDR1: | DNYMH | (SEQ ID NO: 13) |
| CDR2: | WIDPENGDTEYAPKFQG | (SEQ ID NO: 14) |
| CDR3: | WAYYGTSYGGFAY | (SEQ ID NO: 15) |

1A1 Light Chain Variable Region

| | | |
|---|---|---|
| CDR1: | KSSQSLLDSDGKTYLN | (SEQ ID NO: 16) |
| CDR2: | LVSKLDS | (SEQ ID NO: 17) |
| CDR3: | WQGTHFPQT | (SEQ ID NO: 18) |

Example 10

Cloning and Sequencing of mu11K2 Variable Regions

Mouse monoclonal antibody 11K2 was cloned and sequenced according to the following procedure. Total cellular RNA from 11K2 murine hybridoma cells was prepared using the Qiagen RNeasy mini kit according to the manufacturer's recommended protocol.

cDNAs encoding the variable regions of the heavy and light chains were cloned by RT-PCR from total cellular RNA. Following the manufacturers recommended protocols, first-strand cDNAs (prepared with the Amersham First-Strand cDNA Synthesis Kit) were amplified by PCR using the Clontech Advantage 2 PCR Kit. The following primers were used for first-strand synthesis of the 11K2 heavy and light chain cDNAs (Y=C/T, and R=A/G): 11K2 Heavy Chain cDNA Primer: 5'-AGG TCT AGA AYC TCC ACA CAC AGG RRC CAG TGG ATA GAC-3' (SEQ ID NO: 19) and 11K2 Light Chain cDNA Primer: 5'-GCG TCT AGA ACT GGA TGG TGG GAG ATG GA-3' (SEQ ID NO: 20).

The primers used for PCR amplification of the murine 11K2 immunoglobulin heavy chain variable domain were: 5'-GGG GAT ATC CAC CAT GGR ATG SAG CTG KGT MAT SCT CTT-3' (SEQ ID NO: 21) and 5'AGG TCT AGA AYC TCC ACA CAC AGG RRC CAG TGG ATA GAC-3' (SEQ ID NO: 22) (R=A/G, S=C/G, K=G/T, M=A/C, and Y=C/T). The primers used for PCR amplification of the murine 11K2 immunoglobulin light chain variable domain were: 5'-GAY ATH CAR ATG ACN CAG-3' (SEQ ID NO: 23) and 5'-GCG TCT AGA ACT GGA TGG TGG GAG ATG GA-3' (SEQ ID NO: 24) (Y=C/T, H=A/C/T, R=A/G, and N=A/C/G/T).

The PCR was performed at 30 cycles using Clontech's Advantage 2 PCR Kit under the following PCR conditions: denature 0.5 min at 94° C., anneal 1 min at 50° C., and elongate 1 min at 72° C. The PCR products were gel-purified using the Qiagen Qiaquick gel extraction kit following the manufacturer's recommended protocol. Purified 11K2 heavy and light chain PCR products were subcloned into Invitrogen's pCR2.1-TOPO vector using their TOPO TA Cloning kit according to the manufacturer's recommended protocol (pCR-008=11K2 heavy chain, pcr-033=11K2 light chain. Inserts from multiple independent subclones were sequenced according to methods known in the art and those described in Sanger et al., *PNAS* 74, 5463-5467, incorporated herein by reference, and the subclones were found to be identical.

The variable light and heavy chains were compared with the consensus sequences for mouse and human subgroups (Kabat et al, 1991) using the program FASTA and a database of consensus sequences, which are publicly available (see http://people.cryst.bbk.ac.uk/~ubcg07s/). The variable light chain is a member of mouse subgroup Kappa 5 with a 68.8% identity in 113 aa overlap and the variable heavy chain is a member of mouse subgroup 2C with a 85.6% identity in 125 aa overlap. The variable light chain corresponds to human subgroup Kappa 1 with a 69.9% identity in 113 aa overlap. The variable heavy chain corresponds to human subgroup 1 with a 59.7% identity in 129 aa overlap. The predicted amino acid sequences of the mature 11K2 murine variable domains, as well as the determined nucleotide sequences, are shown below in Tables 12 and 13.

TABLE 12

Nucleotide sequence of mu11K2 variable domains

11K2 Heavy Chain Variable Region (SEQ ID NO: 25)
```
  1 GAGGTTCAGCTGCAGCAGTCTGGGGCAGAGCTTGTGAAGGCAGGGGCCTCAGTCAAGTTG  60
 61 TCCTGCCCAGCTTCTGGCCTCAACATTAAAGACACCTATATGCACTGGGTGAAGCAGAGG 120
121 CCTGAACAGGGCCTGGAGTGGATTGGAAGGATTGATCCTGCGAATGGTAATACTAAATTT 180
```

TABLE 12-continued

Nucleotide sequence of mu11K2 variable domains

```
181 GACCCGAAGTTCCAGGGCAAGGCCACTATAACAGCAGACACATCCTCCAACACAGCCTAC 240
241 CTGCAGCTCAGCAGCCTGACATCTGAGGACACTGCCGTCTATTACTGTGCTAGAGGCGTC 300
301 TTTGGCTTTTTTGACTACTGGGGCCAAGGCACCACTCTCACAGTCTCCTCA          351
```

11K2 Light Chain Variable Region (SEQ ID NO: 26)
```
  1 GACATTCAGATGACTCAGTCTTCATCCTCCTTTTCTGTATCTCTAGGAGACAGAGTCACC  60
 61 ATTACTTGCAAGGCAACTGAGGACATATATAATCGATTAGCCTGGTATCAGCAGAAACCA 120
121 GGAAGTGCTCCTAGGCTCTTAATTTCTGGTGCAACCAGTTTGGAGACTGGGGTTCCTTCA 180
181 AGATTCAGTGGCAGTGGATCTGGAAAAGATTACACTCTCAGCATTACCAGTCTTCAGACT 240
241 GAGGATGTTGCTACTTATTACTGTCAACAGTTTTGGAGTGCTCCGTACACGTTCGGAGGG 300
301 GGGACCAAGCTGGAGATCAAA                                        321
```

TABLE 13

Amino acid sequence of 11K2 variable domains
(CDR regions underlined)

11K2 heavy chain variable region (SEQ ID NO: 27)
EVQLQQSGAELVKAGASVKLSCPASGLNIK<u>DTYMH</u>WVKQRPEQGLEWIG<u>RIDPANGNTKFDPK</u>
                             CDR1                 CDR2

<u>FQG</u>KATITADTSSNTAYLQLSSLTSEDTAVYYCAR<u>GVFGFFDY</u>WGQGTTLTVSS
                                  CDR3

11K2 light chain variable region (SEQ ID NO: 28)
DIQMTQSSSSFSVSLGDRVTITC<u>KATEDIYNRLA</u>WYQQKPGSAPRLLIS<u>GATSLET</u>GVPSRFS
                       CDR1                     CDR2

GSGSGKDYTLSITSLQTEDVATYYC<u>QQFWSAPYT</u>FGGGTKLEIK
                         CDR3

Nucleotide and amino acid comparisons of the 11K2 variable heavy and light chains are also shown in FIG. 8. The sequence of the CDR regions of the 11K2 antibody were determined to be as follows:

TABLE 14

CDRs of 11K2 Antibody

11K2 Heavy Chain Variable Region

| | | |
|---|---|---|
| CDR1: DTYMH | (SEQ ID NO: 29) |
| CDR2: RIDPANGNTKFDPKFQG | (SEQ ID NO: 30) |
| CDR3: GVFGFFDY | (SEQ ID NO: 31) |

11K2 Light Chain Variable Region

| | | |
|---|---|---|
| CDR1: KATEDIYNRLA | (SEQ ID NO: 32) |
| CDR2: GATSLET | (SEQ ID NO: 33) |
| CDR3: QQFWSAPYT | (SEQ ID NO: 34) |

Based on the results described above, particularly Tables 3 and 5, antibodies were grouped according to their antigen-binding specificity. The CDR region of mAbs which could recognize MCP-1, MCP-2, and MCP-3, including 4N4, 5A13, 6D21, 615, 7H1, 11K2, and 1A1 were determined as described above. Sequencing revealed that mAbs 4N4, 5A13, 6D21, 615, 7H1, and 11K2 all had identical sequences. Monoclonal antibody 1A1 had a different sequence. Thus, based on CDR cloning, as well as N-terminal sequencing, two distinct pan-MCP monoclonals antibodies were found to exist.

Example 11

PEGylated 11K2 Fab

Figure 13:
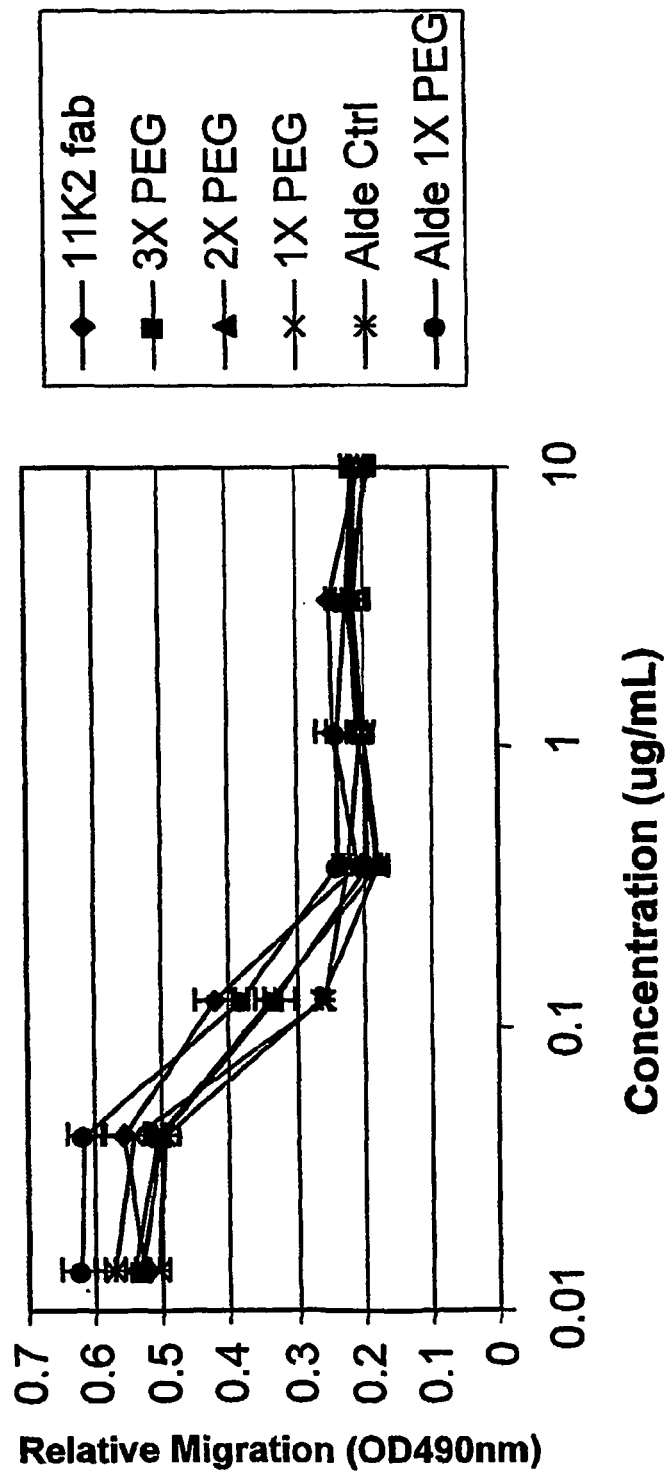
FIG. 13 graphically depicts results from an experiment which demonstrates that PEGylation of 11K2 Fab retains in vitro activity.

As depicted in FIG. 13, PEGylation of the 11K2 Fab fragment does not interfere with 11K2's in vitro activity. PEGylated 11K2 fragments were tested in a chemotaxis inhibition assay (as described previously), using 20 ng·ml of MCP-1. PEGylated 11K2 fragments were as effective as the 11K2 Fab alone at inhibiting migration of the cells.

Example 12

Chimeric 11K2 Antibody

The nucleotide and amino acid sequences of the 11K2 heavy chain chimeric antibody are shown in FIG. 9A. The variable region is defined as nucleotides 1-351 (amino acids 1-117) of the heavy chain. The nucleotide and amino acid sequences of the 11K2 light chain chimeric antibody are shown in FIG. 9B, where the variable region is defined as nucleotides 1-321 and amino acids 1-107.

IV. Humanized 11K2 Antibody

Example 13

11K2 Humanization

Modeling the Structure of the Variable Regions
In order to identify key structural framework residues in the murine 11K2 antibody, a three-dimensional model was generated based on the closest murine antibodies for the heavy and light chains. The 11K2 light and heavy chains were aligned against a local copy of the most recent PDB database to determine structural frames to be used to construct three dimensional models of the light and heavy chains. Using FASTA the light chain was found to have 90.7% sequence identity to monoclonal murine antibody Fab 184.1 (1OSP; 1.8 Å), and the heavy chain was found to have 89.7% sequence identity to murine E8 Fab fragment (1WEJ; 1.8 Å).

Using the molecular modeling package Modeler 5.0 (Accelrys Inc.) the three dimensional structures of the light and heavy chains were built using antibodies 184.1 and E8, respectively. Five homology models were created, and the best one in terms of Modeler energy was selected. Procheck analysis showed that 1 residue (A51, light chain) was in a disallowed region of the phi/psi map, but by comparing phi/psi maps of the different models, the lowest energy model was also the best in phi/psi map violations.

Design of the Reshaped Variable Regions

Human germline sequences were used as the acceptor frameworks for humanized 11K2. To find the closest germline sequences, the NCBI NR database and the Kabat database were searched for the most homologous expressed human frameworks in. In this search the CDR sequences were masked. The selection of the most suitable expressed sequence includes checking for sequence identity of the canonical and interface residues, and checking for the similarity in CDR loop lengths. The source of the antibody was also a determining factor. Previously humanized antibodies were excluded. For the NCBI NR database search, a BLAST was used, and for the Kabat database search, FASTA was used.

The most similar expressed light chain was found in the nr database (GI-486875; Griffiths et al. (1993), supra), and the most similar heavy chain was found in the Kabat database Kabat ID 000054; Kipps. & Duffy (1991), supra). Both sequences were searched against the database of germine sequences (http://www.ncbi.nlm.nih.gov/igblast/), and resulted in the following selected germlines: L11 for the light chain, and 1-69 for the heavy chain.

As noted supra, the humanized antibodies of the invention comprise variable framework regions substantially from a human immunoglobulin (acceptor immunoglobulin) and complementarity determining regions substantially from a mouse immunoglobulin (donor immunoglobulin) termed 11K2. Having identified the complementarity determining regions of 11K2 and appropriate human acceptor immunoglobulins, the next step was to determine which, if any, residues from these components to substitute to optimize the properties of the resulting humanized antibody. The criteria described supra were used to select residues for substitution. A summary of the backmutations is shown below in Table 15:

TABLE 15

Summary of backmutations of humanized 11K2

Backmutations in Reshaped VL - Human germline L11

| | |
|---|---|
| 49 Y → S | This residue is close to a hypervariable loop and it retained in both versions |
| 69 T → K | This residue is close to a hypervariable loop but the sidechain is solvent exposed. Only retained in the first version. |
| 71 F → Y | This is a canonical residue and is retained in both versions |

TABLE 15-continued

Summary of backmutations of humanized 11K2

Backmutations in Reshaped VH - Human germline 1-69

| | |
|---|---|
| 27 G → L | This is a canonical residue. Retained in both versions. |
| 28 T → N | This residue is close to a hypervariable loop. Retained in first version. |
| 29 F → I | This residue is close to a hypervariable loop. Retained in both versions. |
| 30 S → K | This residue is close to a hypervariable loop. Retained in first version. |
| 48 M → I | This residue is close to a hypervariable loop but is a fairly conservative change. Retained in first version. |
| 67 V → A | This residue is close to a hypervariable loop, and is close to residue 48. Retained in first version. |
| 73 K → T | This residue is close to a hypervariable loop. Moreover, the human and mouse consensus is T. Retained in both versions. |

FIG. 12 depicts alignments of the chimeric 11K2 VL and VH, respectively (same as the original murine 11K2 sequence), with the versions 1 and 2 of the humanized 11K2 antibody. Two versions of the variable light reshaped chain and two versions of the variable heavy reshaped chain were designed. The first version contains the most backmutations and the second version contains the fewest (i.e. the most "humanized"). The sequences of the two versions of each variable and heavy chains of humanized 11K2 are shown below:

Humanized 11K2 Heavy Chain (backmutations shown in lower case):

Version 1 (H1) (7 backmutations)
(SEQ ID NO: 47)
QVQLVQSGAEVKKPGSSVKVSCKASGlnikDTYMHWVRQAPGQGLEWiGR IDPANGNTKFDPKFQGRaTITADtSTSTAYMELSSLRSEDTAVYYCARGV

FGFFDYWGQGTTVTVSS

Version 2 (H2) (3 backmutations)
(SEQ ID NO: 48)
QVQLVQSGAEVKKPGSSVKVSCKASGlTiSDTYMHWVRQAPGQGLEWMGR IDPANGNTKFDPKFQGRVTITADtSTSTAYMELSSLRSEDTAVYYCARGV

FGFFDYWGQGTTVTVSS

Humanized 11K2 Light Chain (backmutations shown in lower case):

Version 1 (L1) (3 backmutations)
(SEQ ID NO: 49)
DIQMTQSPSSLSASAVGDRVTITCKATEDIYNRLAWYQQKPGKAPKLLIs GATSLETGVPSRFSGSGSGkDyTLTISSLQPEDFATYYCQQFWSAPYTFG

GGTKVEIK

Version 2 (L2) (2 backmutations)
(SEQ ID NO: 50)
DIQMTQSPSSLSASVGDRVTITCKATEDIYNRLAWYQQKPGKAPKLLIsG ATSLETGVPSRFSGSGSGTDyTLTISSLQPEDFATYYCQQFWSAPYTFGG

GTKVEIK

Tables 16 and 17 set forth Kabat numbering keys for the various light and heavy chains of 11K2, respectively.

TABLE 16

Key to Kabat Numbering for 11K2 Heavy Chain Variable Region

| Kabat # | AA # | Type | Mouse 11K2 | KABID 000054 | Hum. 11K2, v1 | Hum. 11K2, v2 | Comment |
|---|---|---|---|---|---|---|---|
| 1 | 1 | FR1 | E | Q | Q | Q | |
| 2 | 2 | | V | V | V | V | |
| 3 | 3 | | Q | Q | Q | Q | |
| 4 | 4 | | L | L | L | L | |
| 5 | 5 | | Q | V | V | V | |
| 6 | 6 | | Q | Q | Q | Q | |
| 7 | 7 | | S | S | S | S | |
| 8 | 8 | | G | G | G | G | |
| 9 | 9 | | A | A | A | A | |
| 10 | 10 | | E | E | E | E | |
| 11 | 11 | | L | V | V | V | |
| 12 | 12 | | V | K | K | K | |
| 13 | 13 | | K | K | K | K | |
| 14 | 14 | | A | P | P | P | |
| 15 | 15 | | G | G | G | G | |
| 16 | 16 | | A | S | S | S | |
| 17 | 17 | | S | S | S | S | |
| 18 | 18 | | V | V | V | V | |
| 19 | 19 | | K | K | K | K | |
| 20 | 20 | | L | V | V | V | |
| 21 | 21 | | S | S | S | S | |
| 22 | 22 | | C | C | C | C | |
| 23 | 23 | | P | K | K | K | |
| 24 | 24 | | A | A | A | A | |
| 25 | 25 | | S | S | S | S | |
| 26 | 26 | | G | G | G | G | |
| 27 | 27 | | L | G | L | L | Canonical residue, retained |
| 28 | 28 | | N | T | N | T | Residue close to hypervariable loop, retained in v1 (H1) |
| 29 | 29 | | I | F | I | I | Residue close to hypervariable loop, retained |
| 30 | 30 | | K | S | K | S | Residue close to hypervariable loop, retained in v1 (H1) |
| 31 | 31 | CDR1 | D | S | D | D | |
| 32 | 32 | | T | Y | T | T | |
| 33 | 33 | | Y | A | Y | Y | |
| 34 | 34 | | M | I | M | M | |
| 35 | 35 | | H | S | H | H | |
| 36 | 36 | FR2 | W | W | W | W | |
| 37 | 37 | | V | V | V | V | |
| 38 | 38 | | K | R | R | R | |
| 39 | 39 | | Q | Q | Q | Q | |
| 40 | 40 | | R | A | A | A | |
| 41 | 41 | | P | P | P | P | |
| 42 | 42 | | E | G | G | G | |
| 43 | 43 | | Q | Q | Q | Q | |
| 44 | 44 | | G | G | G | G | |
| 45 | 45 | | L | L | L | L | |
| 46 | 46 | | E | E | E | E | |
| 47 | 47 | | W | W | W | W | |
| 48 | 48 | | I | M | I | M | Residue close to hypervariable loop, retained in v1 (H1) |
| 49 | 49 | | G | G | G | G | |
| 50 | 50 | CDR2 | R | G | R | R | |
| 51 | 51 | | I | I | I | I | |
| 52 | 52 | | D | I | D | D | |
| 52A | 53 | | P | P | P | P | |
| 53 | 54 | | A | I | A | A | |
| 54 | 55 | | N | F | N | N | |
| 55 | 56 | | G | G | G | G | |
| 56 | 57 | | N | T | N | N | |
| 57 | 58 | | T | A | T | T | |
| 58 | 59 | | K | N | K | K | |
| 59 | 60 | | F | Y | F | F | |
| 60 | 61 | | D | A | D | D | |
| 61 | 62 | | P | Q | P | P | |
| 62 | 63 | | K | K | K | K | |
| 63 | 64 | | F | F | F | F | |
| 64 | 65 | | Q | Q | Q | Q | |

TABLE 16-continued

Key to Kabat Numbering for 11K2 Heavy Chain Variable Region

| Kabat # | AA # | Type | Mouse 11K2 | KABID 000054 | Hum. 11K2, v1 | Hum. 11K2, v2 | Comment |
|---|---|---|---|---|---|---|---|
| 65 | 66 | | G | G | G | G | |
| 66 | 67 | FR3 | K | R | R | R | |
| 67 | 68 | | A | V | A | V | Residue close to hypervariable loop, retained in v1 (H1) |
| 68 | 69 | | T | T | T | T | |
| 69 | 70 | | I | I | I | I | |
| 70 | 71 | | T | T | T | T | |
| 71 | 72 | | A | A | A | A | |
| 72 | 73 | | D | D | D | D | |
| 73 | 74 | | T | E | T | T | Residue close to hypervariable loop, retained |
| 74 | 75 | | S | S | S | S | |
| 75 | 76 | | S | T | T | T | |
| 76 | 77 | | N | S | S | S | |
| 77 | 78 | | T | T | T | T | |
| 78 | 79 | | A | A | A | A | |
| 79 | 80 | | Y | Y | Y | Y | |
| 80 | 81 | | L | M | M | M | |
| 81 | 82 | | Q | E | E | E | |
| 82 | 83 | | L | L | L | L | |
| 82A | 84 | | S | S | S | S | |
| 82B | 85 | | S | S | S | S | |
| 82C | 86 | | L | L | L | L | |
| 83 | 87 | | T | R | R | R | |
| 84 | 88 | | S | S | S | S | |
| 85 | 89 | | E | E | E | E | |
| 86 | 90 | | D | D | D | D | |
| 87 | 91 | | T | T | T | T | |
| 88 | 92 | | A | A | A | A | |
| 89 | 93 | | V | V | V | V | |
| 90 | 94 | | Y | Y | Y | Y | |
| 91 | 95 | | Y | Y | Y | Y | |
| 92 | 96 | | C | C | C | C | |
| 93 | 97 | | A | A | A | A | |
| 94 | 98 | | R | R | R | R | |
| 95 | 99 | CDR3 | G | G | G | G | |
| 96 | 100 | | V | S | V | V | |
| 97 | 101 | | F | S | F | F | |
| 98 | 102 | | G | W | G | G | |
| 99 | 103 | | F | T | F | F | |
| 100 | 104 | | F | F | F | F | |
| 101 | 105 | | D | D | D | D | |
| 102 | 106 | | Y | Y | Y | Y | |
| 103 | 107 | FR4 | W | W | W | W | |
| 104 | 108 | | G | G | G | G | |
| 105 | 109 | | Q | Q | Q | Q | |
| 106 | 110 | | G | G | G | G | |
| 107 | 111 | | T | T | T | T | |
| 108 | 112 | | T | L | T | T | |
| 109 | 113 | | L | V | V | V | |
| 110 | 114 | | T | T | T | T | |
| 111 | 115 | | V | V | V | V | |
| 112 | 116 | | S | S | S | S | |
| 113 | 117 | | S | S | S | S | |

TABLE 17

Key to Kabat Numbering for 11K2 Light Chain Variable Region

| Kabat # | AA # | Type | Mouse 11K2 | GI-486875 | Hum. 11K2, v1 | Hum. 11K2, v2 | Comment |
|---|---|---|---|---|---|---|---|
| 1 | 1 | FR1 | D | D | D | D | |
| 2 | 2 | | I | I | I | I | |
| 3 | 3 | | Q | Q | Q | Q | |
| 4 | 4 | | M | M | M | M | |
| 5 | 5 | | T | T | T | T | |
| 6 | 6 | | Q | Q | Q | Q | |
| 7 | 7 | | S | S | S | S | |

TABLE 17-continued

Key to Kabat Numbering for 11K2 Light Chain Variable Region

| Kabat # | AA # | Type | Mouse 11K2 | GI-486875 | Hum. 11K2, v1 | Hum. 11K2, v2 | Comment |
|---|---|---|---|---|---|---|---|
| 8 | 8 | | S | P | P | P | |
| 9 | 9 | | S | S | S | S | |
| 10 | 10 | | S | S | S | S | |
| 11 | 11 | | F | L | L | L | |
| 12 | 12 | | S | S | S | S | |
| 13 | 13 | | V | A | A | A | |
| 14 | 14 | | S | S | S | S | |
| 15 | 15 | | L | V | V | V | |
| 16 | 16 | | G | G | G | G | |
| 17 | 17 | | D | D | D | D | |
| 18 | 18 | | R | R | R | R | |
| 19 | 19 | | V | V | V | V | |
| 20 | 20 | | T | T | T | T | |
| 21 | 21 | | I | I | I | I | |
| 22 | 22 | | T | T | T | T | |
| 23 | 23 | | C | C | C | C | |
| 24 | 24 | CDR1 | K | R | K | K | |
| 25 | 25 | | A | E | A | A | |
| 26 | 25 | | T | S | T | T | |
| 27 | 27 | | E | Q | E | E | |
| 28 | 28 | | D | G | D | D | |
| 29 | 29 | | I | I | I | I | |
| 30 | 30 | | Y | R | Y | Y | |
| 31 | 31 | | N | N | N | N | |
| 32 | 32 | | R | D | R | R | |
| 33 | 33 | | L | L | L | L | |
| 34 | 34 | | A | G | A | A | |
| 35 | 35 | FR2 | W | W | W | W | |
| 36 | 36 | | Y | Y | Y | Y | |
| 37 | 37 | | Q | Q | Q | Q | |
| 38 | 38 | | Q | Q | Q | Q | |
| 39 | 39 | | K | K | K | K | |
| 40 | 40 | | P | P | P | P | |
| 41 | 41 | | G | G | G | G | |
| 42 | 42 | | S | K | K | K | |
| 43 | 43 | | A | A | A | A | |
| 44 | 44 | | P | P | P | P | |
| 45 | 45 | | R | K | K | K | |
| 46 | 46 | | L | L | L | L | |
| 47 | 47 | | L | L | L | L | |
| 48 | 48 | | I | I | I | I | |
| 49 | 49 | | S | Y | S | S | Residue close to hypervariable loop, retained. |
| 50 | 50 | CDR2 | G | G | G | G | |
| 51 | 51 | | A | T | A | A | |
| 52 | 52 | | T | S | T | T | |
| 53 | 53 | | S | S | S | S | |
| 54 | 54 | | L | L | L | L | |
| 55 | 55 | | E | Q | E | E | |
| 56 | 56 | | T | S | T | T | |
| 57 | 57 | FR3 | G | G | G | G | |
| 58 | 58 | | V | V | V | V | |
| 59 | 59 | | P | P | P | P | |
| 60 | 60 | | S | S | S | S | |
| 61 | 61 | | R | R | R | R | |
| 62 | 62 | | F | F | F | F | |
| 63 | 63 | | S | S | S | S | |
| 64 | 64 | | G | G | G | G | |
| 65 | 65 | | S | S | S | S | |
| 66 | 66 | | G | G | G | G | |
| 67 | 67 | | S | S | S | S | |
| 68 | 68 | | G | G | G | G | |
| 69 | 69 | | K | T | K | T | Residue close to hypervariable loop, retained in v1 (L1) |
| 70 | 70 | | D | D | D | D | |
| 71 | 71 | | Y | F | Y | Y | Canonical residue, retained. |
| 72 | 72 | | T | T | T | T | |
| 73 | 73 | | L | L | L | L | |
| 74 | 74 | | S | T | T | T | |
| 75 | 75 | | I | I | I | I | |
| 76 | 76 | | T | S | S | S | |

TABLE 17-continued

Key to Kabat Numbering for 11K2 Light Chain Variable Region

| Kabat # | AA # | Type | Mouse 11K2 | GI-486875 | Hum. 11K2, v1 | Hum. 11K2, v2 | Comment |
|---|---|---|---|---|---|---|---|
| 77 | 77 |  | S | S | S | S |  |
| 78 | 78 |  | L | L | L | L |  |
| 79 | 79 |  | Q | Q | Q | Q |  |
| 80 | 80 |  | T | P | P | P |  |
| 81 | 81 |  | E | E | E | E |  |
| 82 | 82 |  | D | D | D | D |  |
| 83 | 83 |  | V | F | F | F |  |
| 84 | 84 |  | A | A | A | A |  |
| 85 | 85 |  | T | T | T | T |  |
| 86 | 86 |  | Y | Y | Y | Y |  |
| 87 | 87 |  | Y | Y | Y | Y |  |
| 88 | 88 |  | C | C | C | C |  |
| 89 | 89 | CDR3 | Q | Q | Q | Q |  |
| 90 | 90 |  | Q | Q | Q | Q |  |
| 91 | 91 |  | F | T | F | F |  |
| 92 | 92 |  | W | T | W | W |  |
| 93 | 93 |  | S | S | S | S |  |
| 94 | 94 |  | A | F | A | A |  |
| 95 | 95 |  | P | P | P | P |  |
| 96 | 96 |  | Y | L | Y | Y |  |
| 97 | 97 |  | T | T | T | T |  |
| 98 | 98 | FR4 | F | F | F | F |  |
| 99 | 99 |  | G | G | G | G |  |
| 100 | 100 |  | G | G | G | G |  |
| 101 | 101 |  | G | G | G | G |  |
| 102 | 102 |  | T | T | T | T |  |
| 103 | 103 |  | K | K | K | K |  |
| 104 | 104 |  | L | V | V | V |  |
| 105 | 105 |  | E | E | E | E |  |
| 106 | 106 |  | I | I | I | I |  |
| 107 | 107 |  | K | K | K | K |  |

Example 14

Cloning and Sequencing of Humanized 11K2

Four different humanized versions of 11K2 were made based on combinations of two different humanized versions of the 11K2 heavy and light chains. Germline sequences were chosen as human acceptor frameworks, including VK L11 for the light chain, and VH 1-69 for the heavy chain. The four combinations of humanized antibodies were designated H1-L1, H1-L2, H2-L1, and H2-L2. Amino acid sequences of the humanized versions of the 11K2 heavy and light chains (nucleotide and amino acid) are shown in FIG. 10. An alignment of the heavy and light chains of the 11K2 chimeric antibody and the humanized 11K2 antibody (versions 1 and 2) is shown in FIG. 11. The first version contains the most backmutations to the murine donor sequences, while the second version contains the fewest (i.e., the most "humanized").

Hu11K2 variable regions were made by site-directed mutagenesis using chimeric 11K2 variable domain plasmids as starting templates. Following the manufacturer's recommended protocol, the QuikChange Site-Directed Mutagenesis Kit (Stratagene Cat. #200518) was used to systematically introduce (framework by framework) the residue changes outlined in above in Tables 16 and 17, as well as FIG. 11. The mutagenic primers for the framework (FR) changes are described below. The cDNA sequence of the human acceptor frameworks (germline VK L 11 for the light chain, and germline VH 1-69 for the heavy chain) were used, with silent mutations introduced to produce restriction site changes to facilitate identification of mutated plasmids. Mutated plasmids were identified by screening for the introduced restriction site changes. The variable region cDNA sequences in the resultant plasmids were confirmed by DNA sequencing.

Hu11K2 light chain mutagenesis was performed according to the following protocol. For the 11K2 version 1 light chain, plasmid pCR060 was used as template in a PCR reaction with the following primers: FR1 primer 5' CCC GCG GAG ACA TTC AGA TGA CTC AGT CTC CAT CCT CCC TGT CAG CAT CTG TGG GAG ACA GAG TCA CCA TTA CTT GCA AGG C3' (SEQ ID NO: 57), which added an A1wn1 site; FR2 primer 5' GGT ATC AGC AGA AAC CAG GAA AGG CCC CTA AGC TCT TAA TTT CTG GTG CAA CC 3' (SEQ ID NO: 58), which added an EcoO109 I site; FR3 primer 5' GGA AAA GAT TAC ACT CTC ACC ATT AGC AGT CTA CAG CCT GAG GAT TTT GCT ACT TAT TAC TGT CAA CAG 3' (SEQ ID NO: 59), which added an Accl site; and FR4 primer 5' CGT TCG GAG GGG GGA CCA AGG TGG AGA TCT AAA AAA AGG GCG AAT TCT G 3' (SEQ ID NO: 60), which added a StyI site. The resultant version 1 light chain plasmid was designated pCR067.

For the 11K2 version 2 light chain, plasmid pCR067 was used as template in a PCR reaction with the following primer: FR3 primer 5' GAT TCA GTG GCA GTG GAT CCG GAA CAG ATT ACA CTC TCA CCA TTA GC 3' (SEQ ID NO: 61), which introduced a BspeI site. The resultant version 2 light chain plasmid was designated pCR06.

Hu11K2 heavy chain mutagenesis was performed according to the following protocol. For the 11K2 version 1 heavy chain, plasmid pCR046 was used as template with the following primers: FR1 primers 5' GTG GTT ACA GGG GTC AAC TCA CAG GTT CAG CTG GTG CAG TCT GGG GCA GAG CTT G 3' (SEQ ID NO: 62), which added a Hinc2 site, and 5' GCA GTC TGG GGC AGA GGT GAA GAA GCC CGG GTC CTC AGT CAA GGT CTC CTG CAA GGC TTC TGG CCT CAA CAT TAA AGA C3' (SEQ ID NO: 63), which added a Sma1 site; FR2 primer 5' GAC ACC TAT ATG CAC TGG GTG CGA CAG GCG CCT GGA CAG GGC CTG GAG TGG ATT GG 3' (SEQ ID NO: 64), which added a NarI site; FR3 primer 5' CCC GAA GTT CCA GGG CAG AGC CAC TAT AAC AGC AGA CAC ATC CAC GAG CAC AGC CTA CAT GGA GCT CAG CAG CCT GAG ATC TGA GGA CAC TGC CG 3' (SEQ ID NO: 65), which added a SacI site; and FR4 primer 5' GGG GCC AAG GGA CCA CTG TGA CAG TCT CCT CAG GTG AGT CCT AAG CTT GGT ACC CGG G 3' (SEQ ID NO: 66), which added an Ava2 site. The resultant version 1 heavy chain plasmid was designated pCR066.

For the 11K2 version 2 heavy chain, plasmid pCR066 was used as template in a PCR reaction with the following primers: FR1 primer 5' GGT CTC CTG CAA GGC TTC AGG CCT CAC CAT TAG CGA CAC CTA TAT GCA CTG GG 3' (SEQ ID NO: 67), which added a StuI site; FR2 primer 5' GGC GCC TGG ACA GGG CCT CGA GTG GAT GGG AAG GAT TGA TCC TGC G 3' (SEQ ID NO: 68), which added an XhoI site; and FR3 primer 5' GAC CCG AAG TTC CAG GGC AGA GTC ACT ATA ACT GCA GAC ACA TCC ACG AGC ACA GCC 3' (SEQ ID NO: 69), which added a PstI site. The resultant version 2 heavy chain plasmid was designated pCR072.

Example 15

Expression of Humanized 11K2 Antibodies

Expression vectors for the hu11K2 light chains were made by subcloning the 0.40 kb NotI-BglII light chain variable domain fragments from pCR067, pCR069 or pCR037 (murine 11K2 light chain variable domain bulk pcr reaction), and the 0.68 kb BclI-NotI fragment from the plasmid pEAG963, containing a human kappa light chain constant domain, into the NotI site of the pCEP4 EBV expression vector-derived plasmid pCH274, producing light chain expression vectors pCR068 (version 1), pCR077 (version 2), and pCR045 (light chain chimera). NotI and BglII sites were engineered onto pCR032 prior to digestion.

Expression vectors for the hu11K2 heavy chains were made by subcloning the 0.49 kb NotI-HindIII heavy chain variable domain fragments from pCR066, pCR072 or pCR032* (murine 11K2 heavy chain variable domain), and the 1.21 kb HindIII-NotI fragment from the plasmid pEAG964, containing a human IgG1 constant region, into the NotI site of the pCEP4 EBV expression vector-derived plasmid pCH274, producing heavy chain expression vectors pCR073 (version 1), pCR075 (version 2) and pCR054 (heavy chain chimera). NotI and HindIII sites were engineered into plasmid pCR032 prior to digestion.

Hu11K2 heavy and light chain expression vectors were co-transfected in all four (4) combinations (i.e. H1-L1, H1-L2, H2-L1 and H2-L2) into 293-EBNA cells and transfected cells were tested for antibody secretion and specificity. Western blot analysis (developed with anti-human heavy and light chain antibodies) of whole cell lysates and the conditioned culture media indicated that hu11K2-transfected cells synthesized and efficiently secreted heavy and light chains at levels similar to chimeric 11K2-transfected cells. All combinations retained reactivity to MCP-1 (murine, primate, and human) and MCP-2 (human) immobilized on ELISA plates.

Example 16

Characterization of Humanized 11K2

ELISA Screening

Binding specificities of chimeric 11K2 and the four versions of humanized 11K2 (H1-L1, H1-L2, H2-L1, and H2-L2) were determined by ELISA, according to the protocol described in Example 1. Human, mouse, and primate MCP-1 were used as antigen, and antibody 3G9, which does not bind MCP-1, was used as a negative control.

ELISA plates (Corning, Inc. Cat#3369) were coated with 50 ng MCP-1 per well overnight at 4° C. Plates were washed then blocked with PBS/5% milk for 1.5 hrs at 25° C. Another wash was followed by incubation with the 11K2 mAbs (or 3G9 isotype control) at the concentrations indicated for 1 hr at 25° C. After washing, the plates were incubated with secondary antibody (anti-human IgG-HRP, Jackson Immunoresearch Cat#109-036-088) for 1 hr at 25° C. Plates were then washed and developed using the ABTS Peroxidase Substrate Kit (Vector Laboratories Cat#SK-4500). OD (405 nm) values were plotted as a function of 11K2 mAb concentration.

Figure 14A:
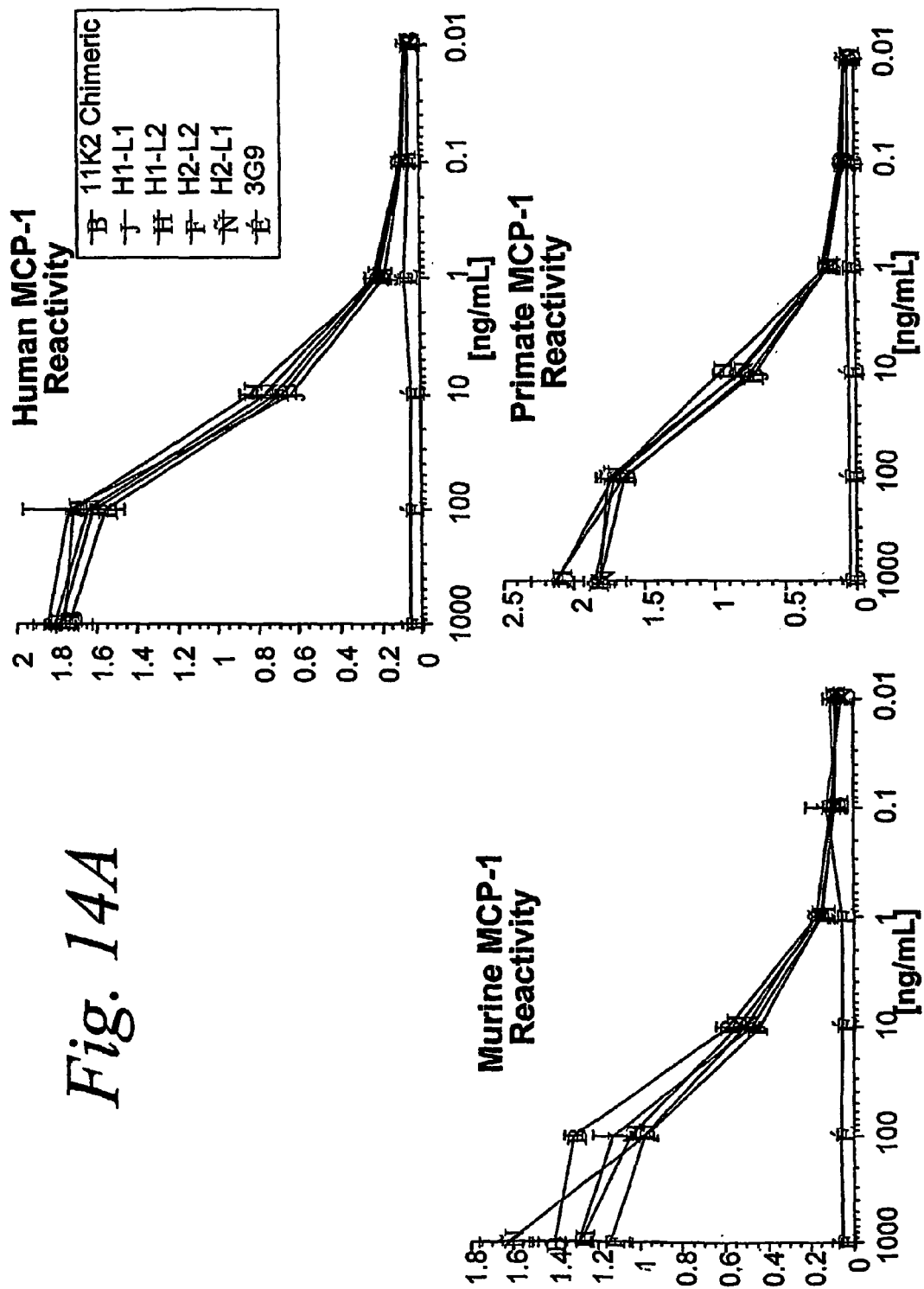
FIG. 14A graphically depicts results from an ELISA experiment, which show reactivity of the humanized and chimeric 11K2 antibodies with huMCP-1, primate MCP-1, and muMCP-1.
Figure 14B:
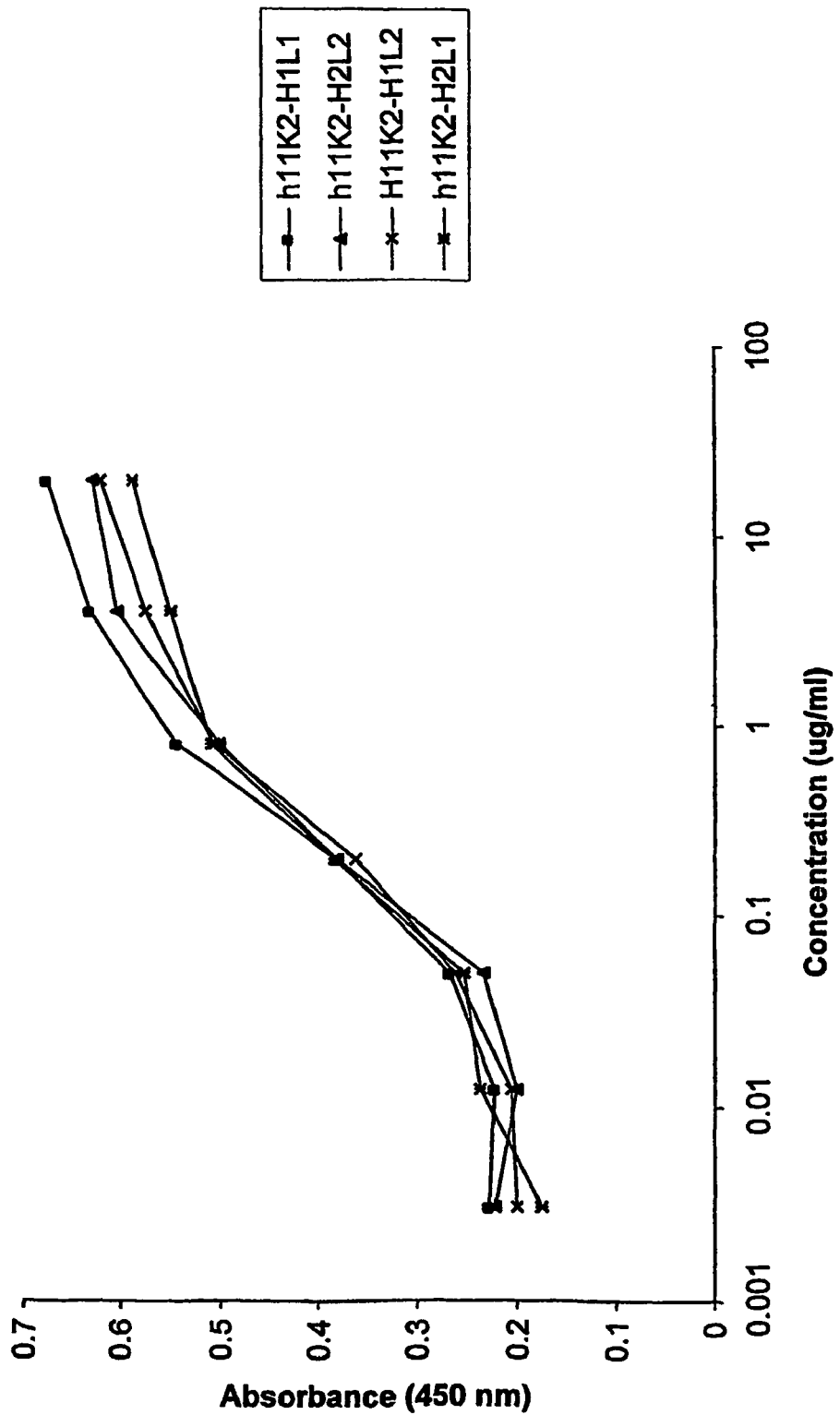
FIG. 14B graphically depicts results from an ELISA experiment, which show the reactivity of humanized and chimeric 11K2 antibodies with MCP-2.

Results from the ELISA experiment are shown below in Table 18 and FIGS. 14A and 14B. These results demonstrate that each of the humanized and chimeric antibodies retained MCP-1 reactivity for each of the species tested.

TABLE 18

Summary of humanised 11K2 reactivities

| | MCP-1 | | | MCP-2 | MCP-3 |
|---|---|---|---|---|---|
| | Human | Mouse | Monkey | Human | Human |
| Chimera | yes | yes | yes | yes | no |
| H1-L1 | yes | yes | yes | yes | no |
| H1-L2 | yes | yes | yes | yes | no |
| H2-L1 | yes | yes | yes | yes | no |
| H2-L2 | yes | yes | yes | yes | no |

Binding Affinity Measurement of Humanized 11K2

Binding affinity studies were performed in order to compare the four versions of the humanized 11K2 anti-MCP antibody to chimeric and murine 11K2 antibodies. KinExA experiments were performed, as previously described. Briefly, reagents that were used included the following. Recombinant human MCP-1 (catalog #279-MC) and MCP-2 (catalog #281-CP, R&D Systems, Inc.) were reconstituted to 100 µg/ml in PBS 0.1% BSA and stored at 4° C. for the duration of the experiment. mu11K2 was purified from hybridoma cell line supernatant. Humanized 11K2 was purified from 293 cell supernatant. All Fab fragments were generated according to standard methods. NHS Sepharose beads (catalog #17-0906-01), Amersham Biosciences (Uppsula, Sweden) were also used to determine affinity through the KinExA method. Goat anti-human Cy-5 conjugate (catalog #109-177-003, Jackson ImmunoResearch) was also used.

To determine the binding affinity of the hu11K2, NHS-Sepharose beads were washed six times in dH$_2$O and once in 50 mM NaHCO$_3$, pH 9.5. 1 ml of MCP-1 at a concentration of 10 µg/ml in NaHCO$_3$ was added to an amount of beads equivalent to 1 ml of the original slurry. The beads were rocked overnight at 4° C. Beads were spun down and washed once with 1M Tris, pH 8.0, then resuspended in 1M Tris pH 8.0 with 1% BSA, 0.02% azide. The beads were rocked at room temperature for one hour then stored at 4° C. in this buffer for the duration of the experiments.

The KinExA 3000 measures protein-protein interaction in solution, and is ideally suited for measuring affinities of antibodies to antigens. In the typical experiment, antigen (MCP) is immobilized on a bead, antibody is flowed over a column of these beads at a given concentration, and the antibody that binds to the beads is detected using a fluorescent secondary. Antibody at a fixed concentration is then incubated with different concentrations of antigen in solution and the amount of free antibody is measured by flowing the mixture over the bead column quickly enough that no re-equilibration occurs between solution and solid phase. The amount of antibody remaining free is plotted against the concentration of antigen added and the data are fit to a quadratic equation to determine the affinity of the interaction in solution.

In these experiments, the only difference to the typical experiment described above is that instead of using intact antibody, a Fab fragment of 11K2 was used. Earlier KimExA experiments using the intact murine 11K2 mAb binding to MCP-1 and MCP-2 gave biphasic curves that the software could not interpret. This may be due to these proteins acting as dimers, so to eliminate the dimer/dimer interaction we generated Fab fragments. The binding of the 11K2 Fab fragments to MCP-1 and MCP-2 produced curves that the KinExA software could fit. Results from the KinExA experiment are shown below in Table 19.

TABLE 19

MCP affinity measurements in solution of humanized 11K2 Fab variants

| Antibody | MCP-1 | MCP-2 | MCP-3 |
|---|---|---|---|
| mu11K2 Fab | 11 pM | 430 pM | >50 nM |
| Ch11K2 | 19.6 pM | 226 pM | ND |
| H1L1 | 36.4 pM | 725 pM* | ND |
| H2L2 | 77.5 pM* | 3.2 nM* | ND |
| H1L2 | 62.3 pM | 712 pM* | ND |
| H2L1 | 64.0 pM | 940 pM* | ND |
| 1A1 Fab | 12.9 pM | 320 pM | >50 nM |
| D9 mAb | 41.5 pM | ND | ND |
| S14 mAb (commercial) | <5.6 pM | ND | ND |

*significant difference from murine and chimeric

Example 17

Inhibition of THP-1 Chemotaxis by Chimeric and Humanized 11K2

Figure 12A:
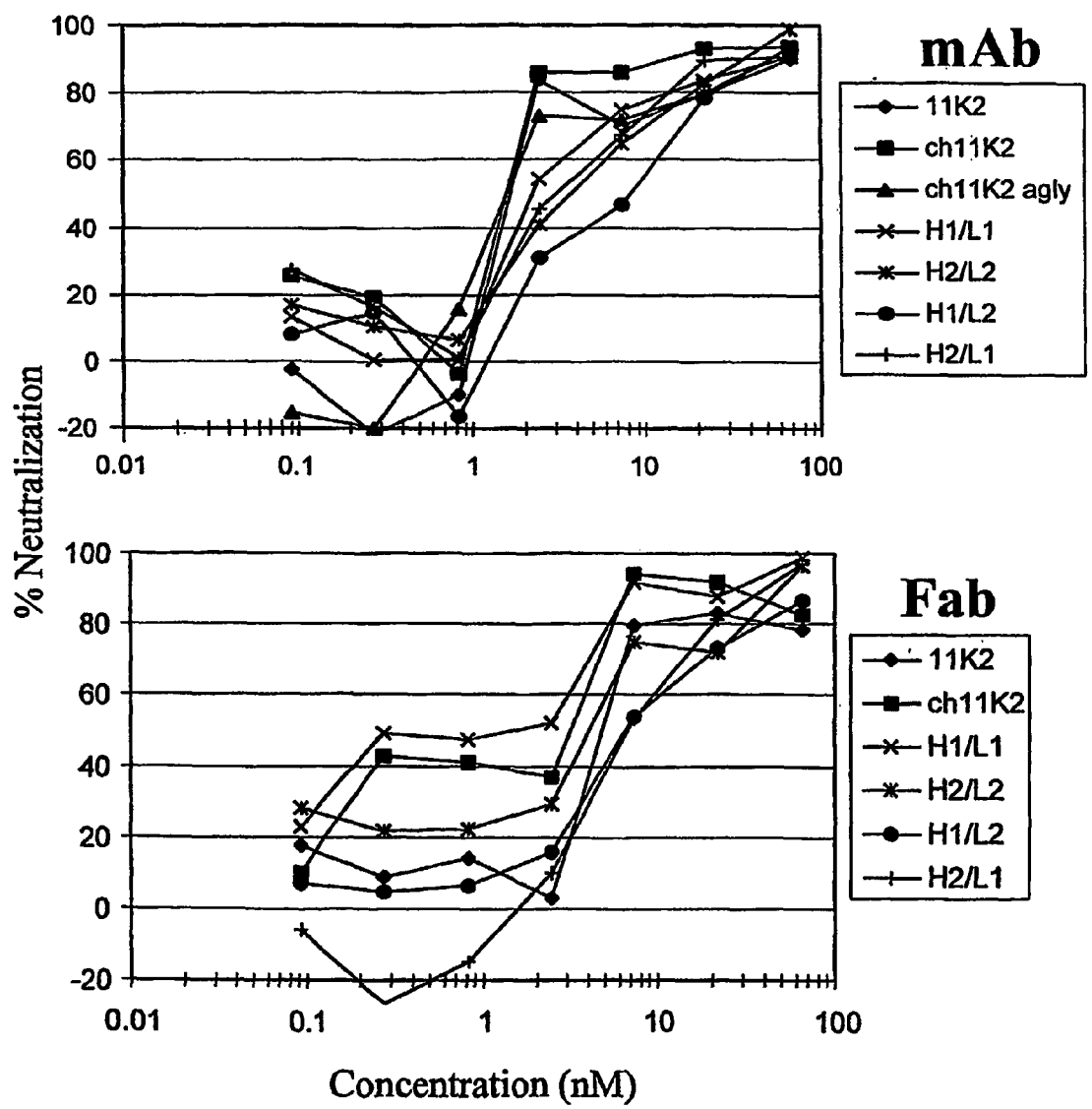
FIG. 12A graphically depicts results from a neutralization assay using 2.3 nM MCP-1.
Figure 12B:
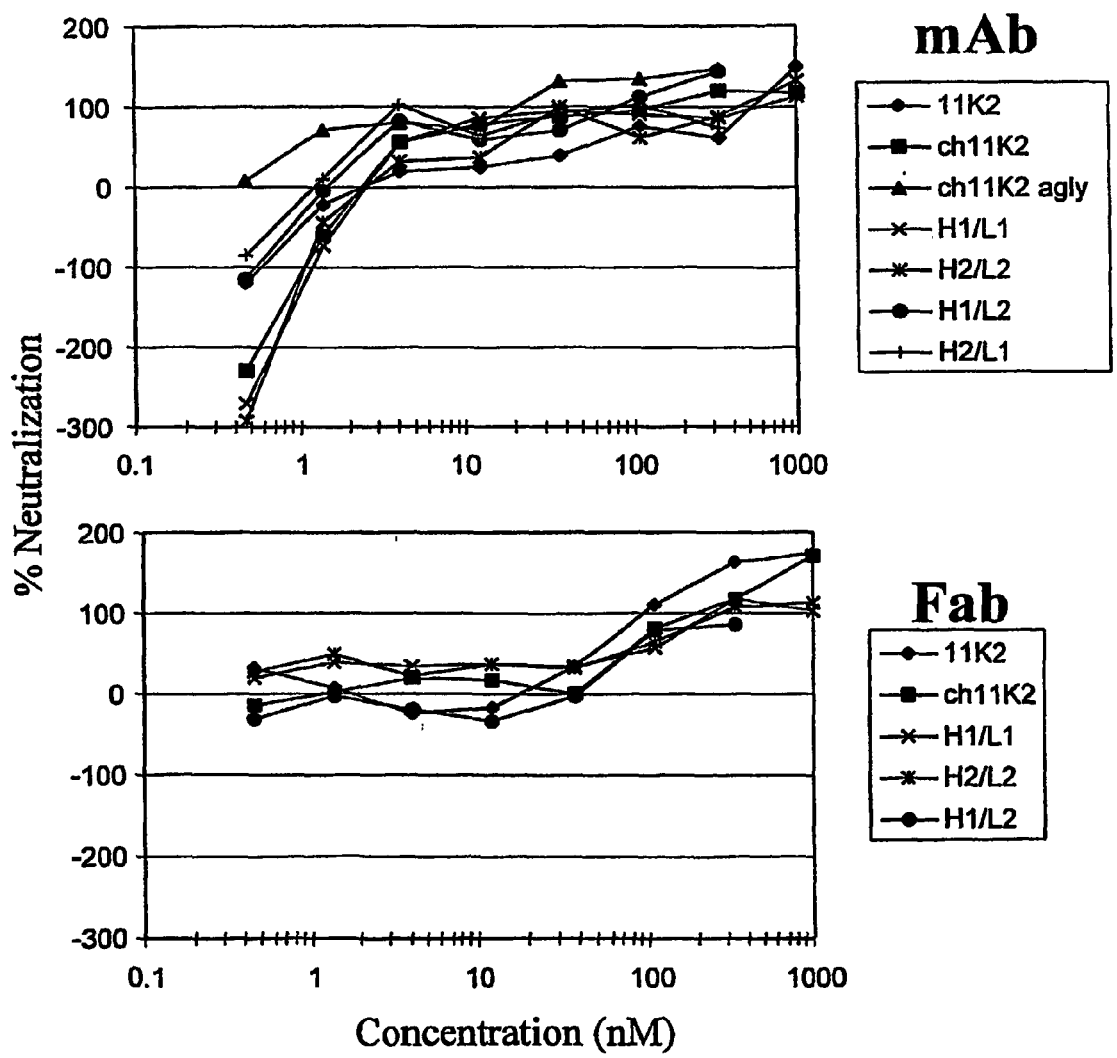
FIG. 12B graphically depicts results from a neutralization assay using 56 nM MCP-2. All of the antibodies tested exhibit an agonist activity for MCP-2 at low concentrations.

Chemotaxis inhibition assays were performed as previously described in Example 3, using MCP-1 to induce THP-1 cell migration. MCP-1 was used at a concentration of 2.3 nM. The results, shown in FIG. 12A, demonstrate that chimeric 11K2 and humanized versions were as effective as monoclonal 11K2 at inhibiting THP-1 cell chemotaxis. In additional experiments using MCP-2 (at a concentration of 56 nM) to induce THP-1 migration, chimeric and all humanized versions of 11K2 were effective at inhibiting chemotaxis (FIG. 12). Interestingly, the agonist effect observed with monoclonal 11K2 was also observed with chimeric and humanized 11K2 versions, as seen in FIG. 12B. In contrast to forms of 11K2 mAb having normal Fc region functionality, an aglycosylated form of the chimeric 11K2 mAb no longer demonstrates agonist activity towards human MCP-2. Thus, the aglycosylated form of 11K2 is acting as a complete antagonist of both human MCP-1 and MCP-2.

V. Humanized 1A1 Antibody

Example 18

1A1 Humanization

Modeling the structure of the variable regions

In order to identify key structural framework residues in the murine 1A1 antibody, a three-dimensional model was generated based on the closest murine antibodies for the heavy and light chains. The 1A1 light and heavy chains were aligned against a local copy of the most recent PDB database to determine structural frames to be used to construct three dimensional models of the light and heavy chains. Using FASTA the light chain was found to have 91.1% sequence identity to monoclonal murine antibody Fab1583 (1NLD; 2.9 Å), and have 87.4% sequence identity to the catalytic murine antibody D2.5 (1YEE; 2.2 Å). The heavy chain was found to have 85.7% sequence identity to murine 2E8 Fab fragment (12E8; 1.9 Å), and 68.1% sequence identity to the murine monoclonal antibody F9.13.7 (1FBI; 3.0 Å). The reason for including 1FBI with a relatively low sequence homology was that it has the same H3 loop length and also a relatively high sequence conservation in the H3 loop.

Two composite antibody structures were created by aligning the light chains of 1NLD and 1YEE onto the light chains of 12E8 and 1FBI, respectively. The atoms used to define the superposition were the Cα atoms of the light chain interface residues. The two full structural templates were obtained by saving the structural combinations of 1NLD(light)/12E8 (heavy) and 1YEE(light)/1FBI(heavy).

Using the molecular modeling package Modeler 5.0 (Accelrys Inc.) the three dimensional structures of the light and heavy chains were built using the two composite structures. Five homology models were created, and the best one in terms of Modeler energy was selected. Procheck analysis showed that no residues were in a disallowed region of the phi/psi map.

Design of the reshaped variable regions

Human germline sequences were used as the acceptor frameworks for humanized 1A1. To find the closest germline sequences, the NCBI NR database and the Kabat database were searched for the most homologous expressed human frameworks in. In this search the CDR sequences were masked. The selection of the most suitable expressed sequence included checking for sequence identity of the canonical and interface residues, and checking for the similarity in CDR loop lengths. The source of the antibody was also a determining factor. Previously humanized antibodies were excluded. BLAST was used for the NCBI NR database search, and the Kabat database was used for the FASTA search.

The most similar expressed light chain was found in the nr database (GI-284256; Kennedy (1991), supra), and the most similar heavy chain was found in the Kabat database (Kabat ID 037655; Bejcek et al. (1995) supra). Both sequences were searched against the database of germline sequences (available at world wide web ncbi.nlm.nih.gov/igblast/), which resulted in the following selected germlines: A17 for the light chain, and 5-51 for the heavy chain. The light chain germline A17 was identical to the expressed sequence GI-284256 in the framework regions. There were many sequence differences between the 5-51 germline and the Kabat ID 037655 expressed heavy chain, therefore the expressed sequence (25C1) was used instead of the closest germline for the heavy chain.

As noted supra, the humanized antibodies of the invention comprise variable framework regions substantially from a human immunoglobulin (acceptor immunoglobulin) and complementarity determining regions substantially from a mouse immunoglobulin (donor immunoglobulin) termed 1A1. Having identified the complementarity determining regions of 1A1 and appropriate human acceptor immunoglobulins, the next step was to determine which, if any, residues from these components to substitute to optimize the properties of the resulting humanized antibody. The criteria described supra were used to select residues for substitution. A summary of the backmutations is shown below in Table 20:

TABLE 20

Summary of backmutations of humanized 1A1

Backmutations in reshaped VL - Human germline A17

- 2 V -> I    This is a canonical residue and is retained in both versions.
- 36 F -> L   This is an interface residue and a significant change. Retained in both versions.
- 45 R -> K   This is a surface residue but is close to a hypervariable loop. Retained in first version.

Backmutations in reshaped VH - Expressed sequence 25C1 (closest germline 5-51)

- 27 Y → F   This is a canonical residue, but a conservative change. Retained in first version.
- 28 A → N   This residue is close to a hypervariable loop. Retained in first version.
- 29 F → I   This residue is a canonical residue. Retained in both versions.
- 30 S → K   This residue is close to a hypervariable loop. Retained in both versions.
- 66 Q → K   This residue is close to a hypervariable loop and interacts with an Asp. Retained in first version.
- 69 L → M   This residue is close to a hypervariable loop but is a conservative change. Retained in first version.
- 73 K → T   This residue is close to a hypervariable loop, contacting an acidic residue. Retained in both versions.
- 76 S → N   This residue is close to a hypervariable loop. Retained in first version.
- 91 S → Y   This residue is an interface residue and a big change. Retained in both versions.
- 93 A → N   This residue contacts a hypervariable loop. Retained in both versions.
- 94 R → T   This residue is a canonical residue. Retained in both versions.

Two versions of the variable light reshaped chain and two versions of the variable heavy reshaped chain were designed. The first version contains the most backmutations and the second version contains the fewest (i.e. the most "humanized"). The sequences of the two versions of each variable and heavy chains of humanized 1A1 are shown below:

Humanized 1A1 Heavy Chain (backmutations shown in lower case):

```
Version 1 (11 backmutations)
                                          (SEQ ID NO: 53)
QVQLLESGAELVRPGSSVKISCKASGfnikDNYMHWVKQRPGQGLEWIGW IDPENGDTEYAPKFQGkATmTADtSSnTAYMQLSGLTSEDSAVYyCntWA

YYGTSYGGFAYWGQGTTVT

Version 2 (6 backmutations)
                                          (SEQ ID NO: 54)
QVQLLESGAELVRPGSSVKISCKASGYAikDNYMHWVKQRPGQGLEWIGW IDPENGDTEYAPKFQGQATLTADtSSSTAYMQLSGLTSEDSAVYyCntWA

YYGTSYGGFAYWGQGTTVT
```

Humanized 1A1 Light Chain (backmutations shown in lower case):

```
Version 1 (3 backmutations)
                                          (SEQ ID NO: 55)
DiVMTQSPLSLPVTLGQPASISCKSSQSLLDSDGKTYLNWlQQRPGQSPk

RLIYLVSKLDSGVPDRFSGSGSGTDFTLKISRVEAEDVGVYYCWQGTHFP

QTFGQGTKLEIK

Version 2 (2 backmutations)
                                          (SEQ ID NO: 56)
DiVMTQSPLSLPVTLGQPASISCKSSQSLLDSDGKTYLNWlQQRPGQSPR

RLIYLVSKLDSGVPDRFSGSGSGTDFTLKISRVEAEDVGVYYCWQGTHFP

QTFGQGTKLEIK
```

Tables 21 and 22 set forth Kabat numbering keys for the various light and heavy chains of 1A1, respectively.

TABLE 21

Key to Kabat Numbering for 1A1 Heavy Chain Variable Region

| Kabat # | AA # | Type | Mouse 1A1 | 25C1 | Hum. 1A1, v1 | Hum. 1A1, v2 | Comment |
|---|---|---|---|---|---|---|---|
| 1 | 1 | FR1 | E | Q | Q | Q | |
| 2 | 2 | | V | V | V | V | |
| 3 | 3 | | Q | Q | Q | Q | |
| 4 | 4 | | L | L | L | L | |
| 5 | 5 | | Q | L | L | L | |
| 6 | 6 | | Q | E | E | E | |
| 7 | 7 | | S | S | S | S | |
| 8 | 8 | | G | G | G | G | |
| 9 | 9 | | A | A | A | A | |
| 10 | 10 | | E | E | E | E | |

TABLE 21-continued

Key to Kabat Numbering for 1A1 Heavy Chain Variable Region

| Kabat # | AA # | Type | Mouse 1A1 | 25C1 | Hum. 1A1, v1 | Hum. 1A1, v2 | Comment |
|---|---|---|---|---|---|---|---|
| 11 | 11 | | L | L | L | L | |
| 12 | 12 | | V | V | V | V | |
| 13 | 13 | | R | R | R | R | |
| 14 | 14 | | S | P | P | P | |
| 15 | 15 | | G | G | G | G | |
| 16 | 16 | | A | S | S | S | |
| 17 | 17 | | S | S | S | S | |
| 18 | 18 | | V | V | V | V | |
| 19 | 19 | | K | K | K | K | |
| 20 | 20 | | L | I | I | I | |
| 21 | 21 | | S | S | S | S | |
| 22 | 22 | | C | C | C | C | |
| 23 | 23 | | T | K | K | K | |
| 24 | 24 | | A | A | A | A | |
| 25 | 25 | | S | S | S | S | |
| 26 | 26 | | G | G | G | G | |
| 27 | 27 | | F | Y | Y | F | Canonical residue, retained in v1 (H1) |
| 28 | 28 | | N | A | A | N | Residue close to hypervariable loop, retained in v1 (H1) |
| 29 | 29 | | I | F | I | I | Canonical residue, retained |
| 30 | 30 | | K | S | K | K | Residue close to hypervariable loop, retained |
| 31 | 31 | CDR1 | D | S | D | D | |
| 32 | 32 | | N | Y | N | N | |
| 33 | 33 | | Y | W | Y | Y | |
| 34 | 34 | | M | M | M | M | |
| 35 | 35 | | H | N | H | H | |
| 36 | 36 | FR2 | W | W | W | W | |
| 37 | 37 | | V | V | V | V | |
| 38 | 38 | | K | K | K | K | |
| 39 | 39 | | Q | Q | Q | Q | |
| 40 | 40 | | R | R | R | R | |
| 41 | 41 | | P | P | P | P | |
| 42 | 42 | | E | G | G | G | |
| 43 | 43 | | Q | Q | Q | Q | |
| 44 | 44 | | G | G | G | G | |
| 45 | 45 | | L | L | L | L | |
| 46 | 46 | | E | E | E | E | |
| 47 | 47 | | W | W | W | W | |
| 48 | 48 | | I | I | I | I | |
| 49 | 49 | | G | G | G | G | |
| 50 | 50 | CDR2 | W | Q | W | W | |
| 51 | 51 | | I | I | I | I | |
| 52 | 52 | | D | Y | D | D | |
| 52A | 53 | | P | P | P | P | |
| 53 | 54 | | E | G | E | E | |
| 54 | 55 | | N | D | N | N | |
| 55 | 56 | | G | G | G | G | |
| 56 | 57 | | D | D | D | D | |
| 57 | 58 | | T | T | T | T | |
| 58 | 59 | | E | N | E | E | |
| 59 | 60 | | Y | Y | Y | Y | |
| 60 | 61 | | A | N | A | A | |
| 61 | 62 | | P | G | P | P | |
| 62 | 63 | | K | K | K | K | |
| 63 | 64 | | F | F | F | F | |
| 64 | 65 | | Q | K | Q | Q | |
| 65 | 66 | | G | G | G | G | |
| 66 | 67 | FR3 | K | Q | Q | K | Residue close to hypervariable loop, retained in v1 (H1) |
| 67 | 68 | | A | A | A | A | |
| 68 | 69 | | T | T | T | T | |
| 69 | 70 | | M | L | L | M | Residue close to hypervariable loop, retained in v1 (H1) |
| 70 | 71 | | T | T | T | T | |
| 71 | 72 | | A | A | A | A | |
| 72 | 73 | | D | D | D | D | |

TABLE 21-continued

Key to Kabat Numbering for 1A1 Heavy Chain Variable Region

| Kabat # | AA # | Type | Mouse 1A1 | 25C1 | Hum. 1A1, v1 | Hum. 1A1, v2 | Comment |
|---|---|---|---|---|---|---|---|
| 73 | 74 | | T | K | T | T | Residue close to hypervariable loop, retained |
| 74 | 75 | | S | S | S | S | |
| 75 | 76 | | S | S | S | S | |
| 76 | 77 | | N | S | S | N | Residue close to hypervariable loop, retained in v1 (H1) |
| 77 | 78 | | T | T | T | T | |
| 78 | 79 | | A | A | A | A | |
| 79 | 80 | | Y | Y | Y | Y | |
| 80 | 81 | | L | M | M | M | |
| 81 | 82 | | Q | Q | Q | Q | |
| 82 | 83 | | L | L | L | L | |
| 82A | 84 | | S | S | S | S | |
| 82B | 85 | | S | G | G | G | |
| 82C | 86 | | L | L | L | L | |
| 83 | 87 | | T | T | T | T | |
| 84 | 88 | | S | S | S | S | |
| 85 | 89 | | E | E | E | E | |
| 86 | 90 | | D | D | D | D | |
| 87 | 91 | | T | S | S | S | |
| 88 | 92 | | A | A | A | A | |
| 89 | 93 | | V | V | V | V | |
| 90 | 94 | | Y | Y | Y | Y | |
| 91 | 95 | | Y | S | Y | Y | Residue is an interface residue, retained. |
| 92 | 96 | | C | C | C | C | |
| 93 | 97 | | N | A | N | N | Residue contacts hypervariable loop, retained. |
| 94 | 98 | | T | R | T | T | Residue is canonical, retained |
| 95 | 99 | CDR3 | W | K | W | W | |
| 96 | 100 | | A | T | A | A | |
| 97 | 101 | | Y | I | Y | Y | |
| 98 | 102 | | Y | S | Y | Y | |
| 99 | 103 | | G | S | G | G | |
| 100 | 104 | | T | V | T | T | |
| 100A | 105 | | S | V | S | S | |
| 100B | 106 | | Y | D | Y | Y | |
| 100C | 107 | | G | F | G | G | |
| 100D | 108 | | G | Y | G | G | |
| 100E | 109 | | F | F | F | F | |
| 101 | 110 | | A | D | A | A | |
| 102 | 111 | | Y | Y | Y | Y | |
| 103 | 112 | FR4 | W | W | W | W | |
| 104 | 113 | | G | G | G | G | |
| 105 | 114 | | Q | Q | Q | Q | |
| 106 | 115 | | G | G | G | G | |
| 107 | 116 | | T | T | T | T | |
| 108 | 117 | | T | T | T | T | |
| 109 | 118 | | V | V | V | V | |
| 110 | 119 | | T | T | T | T | |

TABLE 22

Key to Kabat Numbering for 1A1 Light Chain Variable Region

| Kabat # | AA # | Type | Mouse 1A1 | GI-284256 | Hum. 1A1, v1 | Hum. 1A1, v2 | Comment |
|---|---|---|---|---|---|---|---|
| 1 | 1 | FR1 | D | D | D | D | |
| 2 | 2 | | I | V | I | I | Canonical residue, retained |
| 3 | 3 | | Q | V | V | V | |
| 4 | 4 | | M | M | M | M | |
| 5 | 5 | | T | T | T | T | |
| 6 | 6 | | Q | Q | Q | Q | |
| 7 | 7 | | S | S | S | S | |
| 8 | 8 | | S | P | P | P | |

TABLE 22-continued

Key to Kabat Numbering for 1A1 Light Chain Variable Region

| Kabat # | AA # | Type | Mouse 1A1 | GI-284256 | Hum. 1A1, v1 | Hum. 1A1, v2 | Comment |
|---|---|---|---|---|---|---|---|
| 9 | 9 | | S | L | L | L | |
| 10 | 10 | | S | S | S | S | |
| 11 | 11 | | F | L | L | L | |
| 12 | 12 | | S | P | P | P | |
| 13 | 13 | | V | V | V | V | |
| 14 | 14 | | S | T | T | T | |
| 15 | 15 | | L | L | L | L | |
| 16 | 16 | | G | G | G | G | |
| 17 | 17 | | Q | Q | Q | Q | |
| 18 | 18 | | P | P | P | P | |
| 19 | 19 | | A | A | A | A | |
| 20 | 20 | | S | S | S | S | |
| 21 | 21 | | I | I | I | I | |
| 22 | 22 | | S | S | S | S | |
| 23 | 23 | | C | C | C | C | |
| 24 | 24 | CDR1 | K | R | K | K | |
| 25 | 25 | | S | S | S | S | |
| 26 | 25 | | S | S | S | S | |
| 27 | 27 | | Q | Q | Q | Q | |
| 27A | 28 | | S | S | S | S | |
| 27B | 29 | | L | L | L | L | |
| 27C | 30 | | L | V | L | L | |
| 27D | 31 | | D | Y | D | D | |
| 27E | 32 | | S | S | S | S | |
| 28 | 33 | | D | D | D | D | |
| 29 | 34 | | G | G | G | G | |
| 30 | 35 | | K | N | K | K | |
| 31 | 36 | | T | T | T | T | |
| 32 | 37 | | Y | H | Y | Y | |
| 33 | 38 | | L | L | L | L | |
| 34 | 39 | | N | N | N | N | |
| 35 | 40 | FR2 | W | W | W | W | |
| 36 | 41 | | L | F | L | L | Interface residue, retained. |
| 37 | 42 | | L | Q | Q | Q | |
| 38 | 43 | | Q | Q | Q | Q | |
| 39 | 44 | | R | R | R | R | |
| 40 | 45 | | P | P | P | P | |
| 41 | 46 | | G | G | G | G | |
| 42 | 47 | | Q | Q | Q | Q | |
| 43 | 48 | | S | S | S | S | |
| 44 | 49 | | P | P | P | P | |
| 45 | 50 | | K | R | K | R | Surface residue close to hypervariable loop, retained in v1. |
| 46 | 51 | | R | R | R | R | |
| 47 | 52 | | L | L | L | L | |
| 48 | 53 | | I | I | I | I | |
| 49 | 54 | | Y | Y | Y | Y | |
| 50 | 55 | CDR2 | L | K | L | L | |
| 51 | 56 | | V | V | V | V | |
| 52 | 57 | | S | S | S | S | |
| 53 | 58 | | K | N | K | K | |
| 54 | 59 | | L | R | L | L | |
| 55 | 60 | | D | D | D | D | |
| 56 | 61 | | S | S | S | S | |
| 57 | 62 | FR3 | G | G | G | G | |
| 58 | 63 | | V | V | V | V | |
| 59 | 64 | | P | P | P | P | |
| 60 | 65 | | D | D | D | D | |
| 61 | 66 | | R | R | R | R | |
| 62 | 67 | | F | F | F | F | |
| 63 | 68 | | T | S | S | S | |
| 64 | 69 | | G | G | G | G | |
| 65 | 70 | | S | S | S | S | |
| 66 | 71 | | G | G | G | G | |
| 67 | 72 | | S | S | S | S | |
| 68 | 73 | | G | G | G | G | |
| 69 | 74 | | T | T | T | T | |
| 70 | 75 | | D | D | D | D | |
| 71 | 76 | | F | F | F | F | |
| 72 | 77 | | T | T | T | T | |
| 73 | 78 | | L | L | L | L | |

TABLE 22-continued

Key to Kabat Numbering for 1A1 Light Chain Variable Region

| Kabat # | AA # | Type | Mouse 1A1 | GI-284256 | Hum. 1A1, v1 | Hum. 1A1, v2 | Comment |
|---|---|---|---|---|---|---|---|
| 74 | 79 | | K | K | K | K | |
| 75 | 80 | | I | I | I | I | |
| 76 | 81 | | S | S | S | S | |
| 77 | 82 | | R | R | R | R | |
| 78 | 83 | | V | V | V | V | |
| 79 | 84 | | E | E | E | E | |
| 80 | 85 | | A | A | A | A | |
| 81 | 86 | | E | E | E | E | |
| 82 | 87 | | D | D | D | D | |
| 83 | 88 | | L | V | V | V | |
| 84 | 89 | | G | G | G | G | |
| 85 | 90 | | V | V | V | V | |
| 86 | 91 | | Y | Y | Y | Y | |
| 87 | 92 | | Y | Y | Y | Y | |
| 88 | 93 | | C | C | C | C | |
| 89 | 94 | CDR3 | W | M | W | W | |
| 90 | 95 | | Q | Q | Q | Q | |
| 91 | 96 | | G | G | G | G | |
| 92 | 97 | | T | T | T | T | |
| 93 | 98 | | H | H | H | H | |
| 94 | 99 | | F | W | F | F | |
| 95 | 100 | | P | P | P | P | |
| 96 | 101 | | Q | Y | Q | Q | |
| 97 | 102 | | T | T | T | T | |
| 98 | 103 | FR4 | F | F | F | F | |
| 99 | 104 | | G | G | G | G | |
| 100 | 105 | | G | Q | Q | Q | |
| 101 | 106 | | G | G | G | G | |
| 102 | 107 | | T | T | T | T | |
| 103 | 108 | | K | K | K | K | |
| 104 | 109 | | L | L | L | L | |
| 105 | 110 | | E | E | E | E | |
| 106 | 111 | | I | I | I | I | |
| 107 | 112 | | K | K | K | K | |

VI. In Vivo Efficacy of Anti-MCP Antibody

Example 19

Efficacy of Anti-MCP Antibody Treatment in TNBS-Induced Murine Colitis Model

To determine the efficacy of anti-MCP antibodies in treating inflammatory disorders, a mouse model of colitis was selected. Colitis was induced in Balb/c mice as previously described (Neurath et al. (1995) *J Exp Med.* 182(5):1281). Briefly, 6-8 week old female Balb/c mice (Charles River, Monza, Italy) were fasted for 1 day, anesthetized, and a 3.5 F catheter was inserted into the colon such that the tip was 4 cm proximal to the anus. To induce colitis in the experimental mice, 1.0 mg of TNBS (Sigma Chemical Co, St Louis, Mo.) in 50% ethanol was administered via catheter into the lumen using a 1 ml syringe (injection volume of 100 μl). Control mice received 50% ethanol alone.

Following induction of colitis, mice were monitored daily for appearance of diarrhea, loss of body weight, and survival. At the end of the experiment, surviving mice were sacrificed and blood samples collected by cardiac puncture. A 7 cm segment of colon was excised, weighed, and evaluated for macroscopic damage. Tissue segments were then used for immunohistochemical studies, or were homogenized in protein extraction buffer (Pierce, Rockford, Il USA) for use in cytokine and myeloperoxidase (MPO) activity measurements as described (Fiorucci et al. (2002) *Immunity* 17: 769). Chemokine measurements were performed using a commercially available ELISA assay for MCP-1 (R+D Systems, Minneapolis, Minn. USA).

TNBS-induced colitis mice receiving 11K2 were studied for physical changes (e.g., weight loss), reduction in proinflammatory mediators, and reduction in circulating MCP-1 to determine the efficacy of 11K2 at treating colitis. TNBS-induced colitis experiments using different forms of the 11K2 antibody were performed in parallel with control antibody mouse monoclonal antibody MOPC21.

Anti-MCP Antibody Treatment Prevents Weight Loss and Enhances Survival

Colitis was induced in experimental mice as described above. Intraperitoneal (IP) injection of monoclonal antibody 11K2 and the control antibody (IgG1b antisera MOPC21) was performed on days −1, 2 and 5. Mice were administered either 200 μg of mouse monoclonal antibody 11K2 or mouse control monoclonal antibody MOPC21. Mice were monitored for weight gain/loss and survival for seven days. On day 1, all mice were observed to weigh about 18 grams. Rapid weight gain was observed in control mice, which reached a plateau weight of about 23 grams by day 4 of the trial. While weight gain in colitis model mice administered monoclonal antibody 11K2 was initially not as rapid as for control mice (non-colitis induced mice), gradual weight gain was observed in the mice over the course of the trial, reaching about 22 grams by day 7. In contrast, TNBS-induced colitis model mice that received either control monoclonal antibody MOPC21 or no antibody failed to gain significant weight between days 1 and 7 of the trial, continuing to weigh about 18 grams on day 7. Thus, 11K2 treated mice showed significant weight gain.

Treatment of colitis-induced mice with 11K2 also improved survival over the seven day course of the trial, as compared to mice treated with TNBS alone or the combination of TNBS and the control monoclonal antibody MOPC21. As shown in FIG. 15, about 70% of colitis model mice treated with 11K2 survived the seven day trial, in contrast to a survival rate of about 40% for colitis model mice administered either the control monoclonal antibody or no antibody. Mouse monoclonal antibody 11K2 treatment therefore reduced lethality associated with TNBS-induced colitis in model mice.

Reduction of Proinflammatory Mediators in Anti-MCP Antibody-Treated Mice

To determine the effect of anti-MCP antibodies at reducing molecules associated with inflammation, colon tissues from TNBS-induced colitis mice were dissected and assayed for concentration of proinflammatory mediator cytokines, TNFα, IFN-γ, and IL-2 according to manufacturer's protocols (R+D Systems, Minneapolis, Minn. USA). Concentrations of the three cytokines were observed to be less than 100 pg/mg in control mice that were not administered TNBS. TNBS induction elevated colonic levels of all three assayed cytokines in TNBS-induced mice and mice administered the combination of TNBS and control monoclonal antibody MOPC21, wherein about 600 pg/mg TNFα, 750 pg/mg IFN-γ, and 500 pg/mg IL 2 was observed. Lower levels of TNFα, IFN-γ, and IL-2 (about 200 pg/mg, 300 pg/mg and 200 pg/mg, respectively) were observed in colon tissues obtained from TNBS-induced colitis mice injected with 11K2. Thus, 11K2 blockade of MCP-1 decreased production of proinflammatory mediators in the inflamed colon.

Reduction of Circulating MCP-1 Levels in Anti-MCP Antibody-Treated Mice

Figure 16:
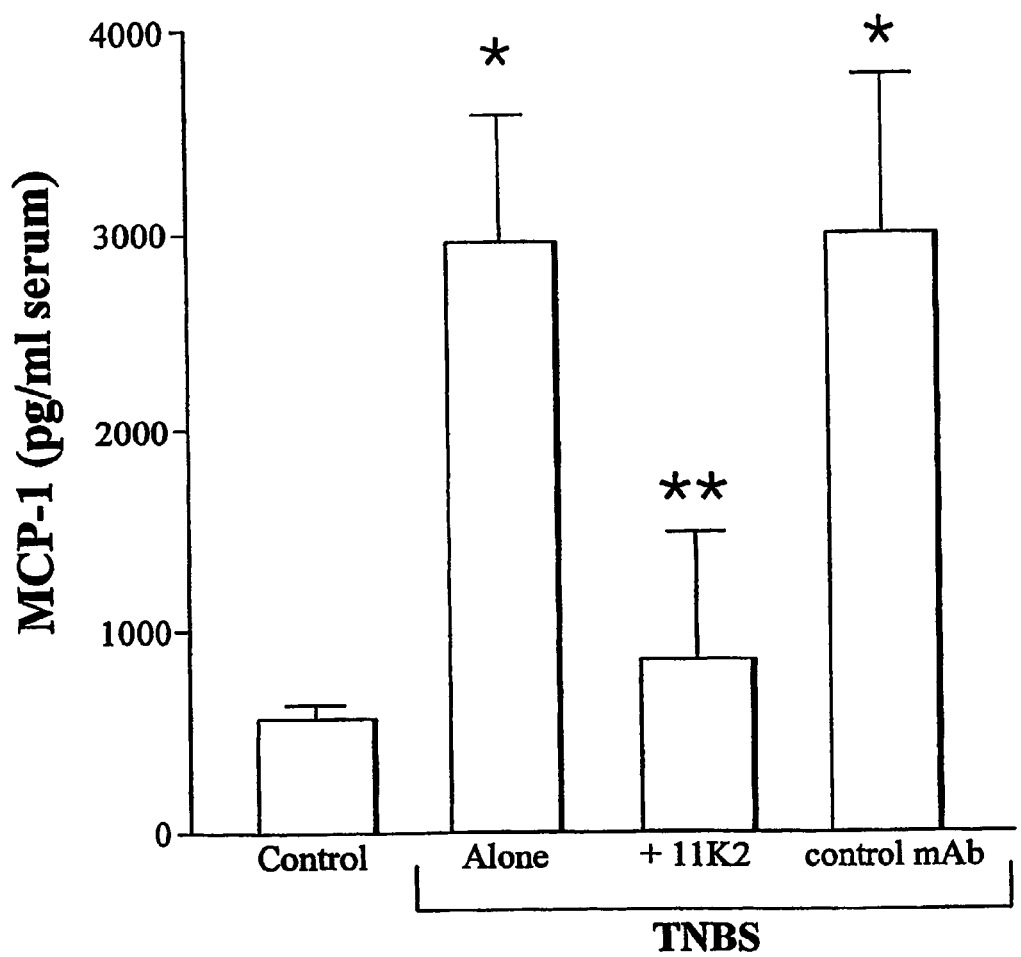
FIG. 16 graphically depicts the reduction of MCP-1 levels seen in TNBS-induced colitis mice treated with monoclonal antibody 11K2.

To determine the effect of 11K2 on MCP-1 in TNBS-induced colitis model mice, circulating levels of MCP-1 were analyzed according to manufacturer's protocols (R+D Systems, Minneapolis, Minn. USA). As shown in FIG. 16, MCP-1 was observed at about 500 pg/ml serum in control mice, whereas serum MCP-1 levels in TNBS-induced colitis mice administered control monoclonal antibody MOPC21 or no antibody were about 3000 pg/ml serum. MCP-1 levels in TNBS-induced colitis mice treated with 11K2 were observed to be about 1000 pg/ml serum, representing a significant reduction of circulating MCP-1 levels relative to TNBS-induced colitis mice administered the control monoclonal antibody or left untreated. Thus, 11K2 treatment significantly reduced the level of MCP-1 in circulation during colitis.

Dose-Dependent Analysis of Anti-MCP Antibody Treatment

Body weight was monitored for groups of TNBS-induced colitis mice injected with varying amounts of mouse 11K2 monoclonal antibody to determine dosage response. 11K2 was administered at doses of 2, 50, 100, and 200 μg/mouse three times a week, respectively. TNBS-induced colitis control mice that did not receive antibody injections or colitis mice receiving only 2 μg doses of 11K2 showed a decline in weight about 25% relative to starting weights over the course of the experiment. Improved body weights were observed for mice administered 50 μg doses of 11K2 (weight declines of about 15%), while improved body weights were observed for mice administered 100 μg and 200 μg doses (weights of these mice were observed to be about equal to starting weights, with slight weight gain observed for those mice treated with 200 μg of 11K2). Uninduced and untreated control mice gained about 15% of body weight over the course of the experiment.

The effect of various doses of 11K2 was also studied by analyzing myeloperoxidase (MPO) activity levels in TNBS-induced colitis mice. To assess MPO activity levels, 50 μl SureBlue TMB (Kirkegaard & Perry Laboratories, Inc.) was added to 50 μl sample, e.g., serum or colon homogenate. This mixture was allowed to incubate at room temperature for 5 minutes, with 100 μl 0.18M $H_2SO_4$ then added to the reaction mixture. Absorbance at 450 nm was detected on a plate reader for all samples, with a range of 0.25 to 1 activity unit per sample. A standard curve was generated using purified MPO (Sigma) in the peroxidase assay. MPO activity levels were ascribed to samples by comparing detected peroxidase activity values with the standard curve. MPO activity in uninduced, untreated control mice was observed to be about 15 U/mg. TNBS-induced mice left untreated exhibited about 35 U/mg MPO activity. Reduced levels of MPO activity were observed in TNBS-induced colitis model mice that had been treated with 50 μg, 100 μg and 200 μg doses of 11K2, with MPO activity levels observed to be about 25 U/mg, 18 U/mg, and 15 U/mg, respectively.

Efficacy of Humanized Anti-MCP Antibody and Pegylated Fab in Treating Colitis

Figure 17:
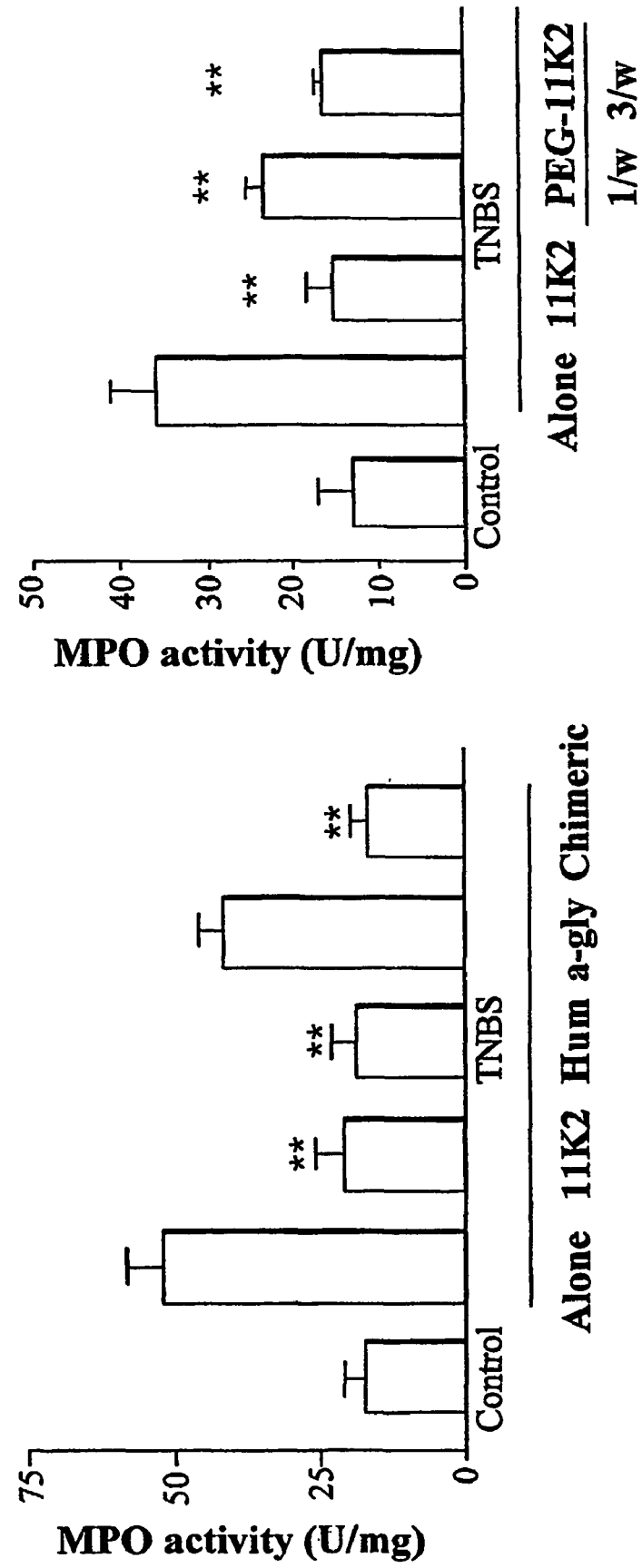
FIG. 17 graphically depicts the results of experiments demonstrating the efficacy of hu11K2 and pegylated 11K2-Fab (11K2 PEG-Fab) to inhibit colitis in a TNBS-induced mice.

To determine the efficacy of humanized 11K2 and 11K2 pegylated-Fab 11K2 PEG-Fab), TNBS-induced mice were treated via intraperitoneal (IP) injection with mouse monoclonal antibody 11K2, humanized 11K2 (hl 1K2) antibody, chimeric 11K2 antibody, aglycosylated 11K2, or no antibody as a control. TNBS-induced colitis model mice were monitored for MPO activity levels. As shown in FIG. 17, administration of either hu11K2 (FIG. 17A) or 11K2 PEG-Fab (FIG. 17B) to TNBS-induced colitis mice resulted in significantly lower MPO levels than TNBS-induced colitis control mice. Both hu11K2- and 11K2 PEG-Fab-treated mouse MPO levels were comparable to those observed for TNBS-induced colitis mice treated with the mouse monoclonal antibody 11K2.

Therapeutic Treatment of Colitis Model Mice by Anti-MCP Antibody

Figure 18:
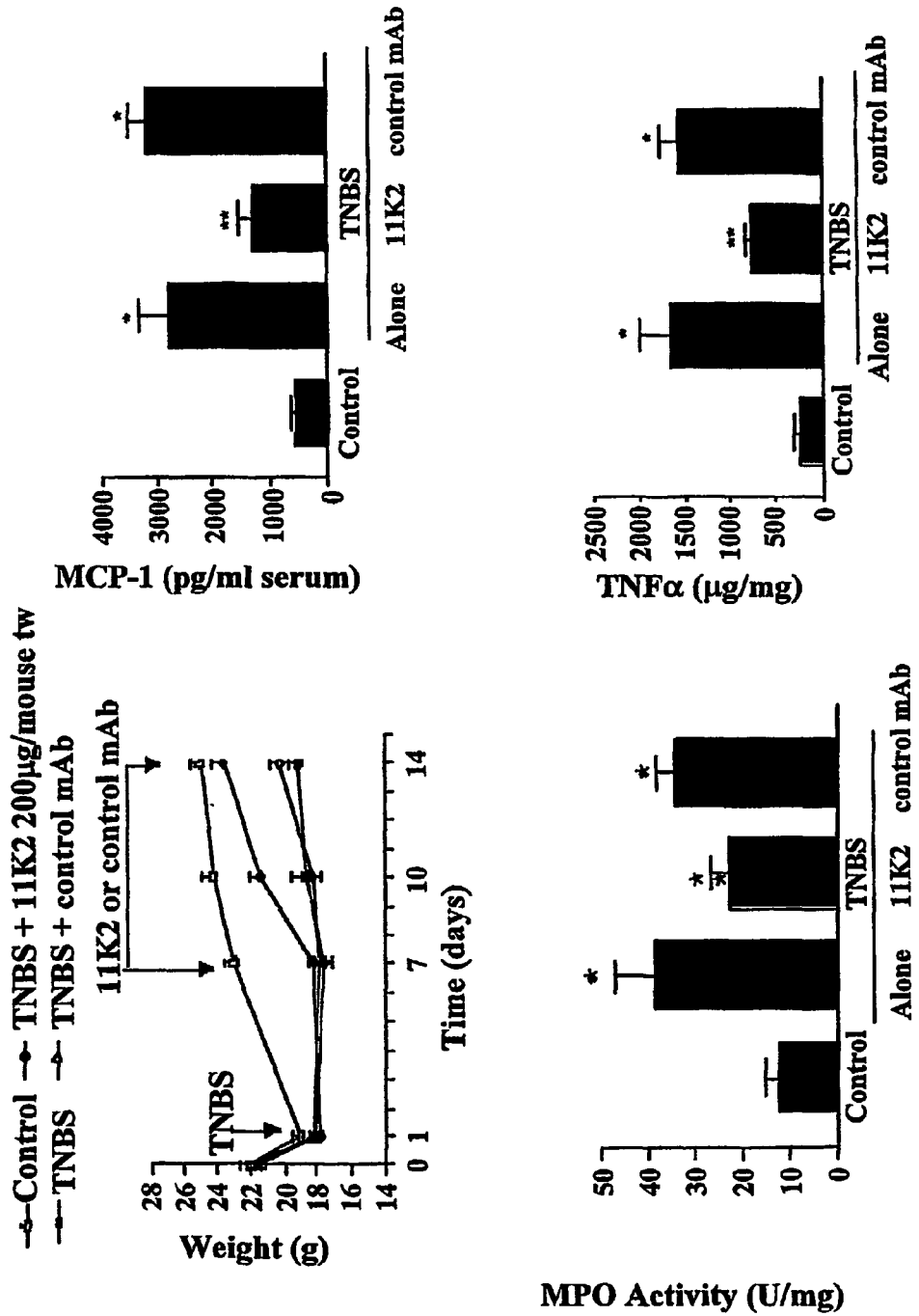
FIG. 18 graphically depicts the therapeutic effect of monoclonal antibody 11K2 administration to TNBS-induced mice. At day 7 post-TNBS-induction 11K2 treatment resulted in elevated body weight, reduced MCP and TNFα levels, and inhibition of myeloperoxidase (MPO) activity, as compared with untreated and control mAb-treated colitis model mice.

TNBS was administered to groups of mice and colitis was allowed to progress for seven days. Mouse monoclonal antibody 11K2 or a control monoclonal antibody were then administered via IP injection to the mice on day 7. Body weight was then measured on days 10 and 14. In addition, MCP-1, TNFα, and MPO activity levels were assessed on day 14 for all mice. Elevated body weight, and significantly inhibited levels of MCP-1, TNFα and MPO activity were all observed for colitis-induced mice that had been treated with 11K2 antibody (see FIG. 18), as compared to colitis model mice left untreated or administered the non-therapeutic control monoclonal antibody.

Example 20

Efficacy of Anti-MCP Antibodies in Atherosclerosis

To determine the efficacy of 11K2 at treating atherosclerosis, the murine ApoE-deficient model was used. Administration of mouse monoclonal antibody 11K2 to atherosclerotic model mice (apoE-deficient) was performed according to the methods of Lutgens et al. (2000) *Proc. Natl. Acad. Sci. USA*. 97:7464). ApoE−/− mice (Iffa Credo) were fed normal chow diet, and administered either 11K2 or a mouse control monoclonal antibody (IgG1b antisera MOPC21) at 200 μg per mouse by intraperitoneal injection twice a week for 12 weeks. Injection of the early treatment group started at 5 weeks of age (n=15 11K2 antibody, n=15 control antibody), when hardly any atherosclerotic lesions are observed to be present. Injections of the delayed treatment group (n=15 11K2 antibody; n=15 control antibody) started at 17 weeks of age, at which point advanced atherosclerotic plaques are known to have developed. Mice of both early and delayed treatment groups were sacrificed at the end of 12 weeks of treatment for examination of plaque development Atherosclerotic plaques were divided into initial and advanced lesions. Initial lesions were defined as fatty streaks containing macrophage-derived foam cells with intracellular lipid accumulation (AHA type II) or pools of extracellular lipid (AHA type III), whereas advanced lesions contained extracellular lipid, a lipid core (AHA type IV), and/or a fibrous cap (AHA type Va-c) (Stary et al. (1995) *Arterioscler. Thromb. Vasc. Biol.* 15:1512). Tissue processing, histological classification, and morphometry were performed as described previously (Lutgens et al. (1999) *Nat. Med.* 5:1313; Lutgens et al. (1999) *Circulation* 99:276). 11K2 antibody-treated apoE–/– mice were compared with control-treated apoE–/– mice. 11K2 antibody-treated apoE–/– mice of the delayed treatment group were also compared with control-treated 17-wk-old apoE–/– mice to investigate plaque progression after treatment. For all analyses, a nonparametric Mann Whitney U test was used. The level of statistical significance was set at P=0.05. As shown in FIG. 19, significant reduction of total plaque area in the aortic arch was observed for both early and advanced groups of mice treated with 11K2.

Quantities of atherosclerotic plaques classified as initial and advanced lesions were analyzed for all groups of mice. As shown in FIG. 19, treatment of atherosclerotic mice with 11K2 reduced the number of plaques. Reduction in the total number of plaques observed in the early treatment group was comparable between control and experimental groups. while about 5 plaques were observed in the aortic arches of both MOPC21 (IgG1b control antisera)- and 11K2-administered mice. Advanced lesion counts were lower for delayed treatment group mice treated with 11K2 (about 3 advanced lesions per aortic arch observed), as compared to delayed treatment group MOPC21-treated mice (about 4 advanced lesions per aortic arch observed). Too few advanced lesion plaques were observed in mice of the early treatment group to assess whether 11K2 treatment reduced advanced lesion formation in the early treatment groups of mice.

All mice were also examined for both macrophage content and CD45+ cell content. Sections were immunolabeled with ED-[20] (1:10) for the detection of macrophages or anti-CD45 antibody. Atherosclerosis model mice treated with 11K2 exhibited reductions in macrophage content of both initial and advanced lesions, among both early and delayed treatment groups of mice (about 75% versus about 85% macrophage content for initial lesions in the early treatment group; about 70% versus about 80% macrophage content for initial lesions of the delayed treatment group; and about 45% versus about 55% macrophage content for advanced lesions of the delayed treatment group). When CD45+ cell content was examined, advanced lesions of the delayed treatment group were significantly reduced for CD45+ cell content in 11K2-treated versus MOPC21 (IgG1b control antisera)-treated mice (50 cells/mm$^2$ versus about 120 cells/mm$^2$).

ApoE–/– mice treated with 11K2 showed systemic abnormalities with either early (5-17 weeks) or late treatment (17-29 weeks) with an anti-MCP antibody. On autopsy, mice treated with 11K2 antisera exhibited no abnormalities relative to control animals in the following tissues: heart, liver, kidneys, lung, lymph nodes, brain, bone, skin, stomach, intestines, colon, salivary glands, gall bladder, prostate, testis, thymus, adrenals, pancreas, bladder, duodenum. No significant differences in CD3+, CD4+ and CD8+ levels were observed in blood, spleen and lymph node tissues of experimental apoE–/– mice treated with 11K2 antisera relative to control-treated animals. Additionally, lipid profiles of 11K2-treated mice were essentially identical to control-treated mice when levels of total cholesterol, triglycerides, HDL cholesterol, and LDL cholesterol were examined.

Collagen and α-smooth muscle actin (ASMA) content were also assessed in plaques of 11K2-treated and control mice via immunolabelling. Plaques from mice in both the early and late treatment groups that were administered control antisera MOPC21 exhibited collagen content of about 3% for initial plaques, while advanced plaques of delayed treatment group mice showed collagen contents of about 30%. In contrast, plaques of early and late treatment mice administered 11K2 antisera showed significantly greater collagen content than control animals, as early and late treatment group initial plaques from 11K2-treated mice had about 6% collagen levels, and advanced plaques from delayed treatment group mice treated with 11K2 exhibited about 40% collagen levels. Similar effects were observed for α-smooth muscle actin (ASMA). Plaques from control-treated mice in both early and delayed treatment groups exhibited about 0.5% ASMA levels for initial plaques, and advanced plaques from control-treated mice in the delayed treatment group revealed about 2% ASMA content. In contrast, plaques dissected from 11K2-treated mice exhibited ASMA content of about 4% for early treatment mice, and about 3% ASMA content for both initial and advanced plaques dissected from delayed treatment mice.

Array-Based Detection of Differentially Expressed Genes in Atherosclerotic Mice

Gene array was used to examine the gene expression patterns of atheroclerotic mice. Groups of C57BL/6 apoE–/– mice fed a diet of normal chow for 3, 4.5, or 6 months, or a western type diet for 3, 4.5, or 6 months, were sacrificed at the end of the experimental period, Following sacrifice, vascular tissue was dissected and subjected to array-based expression profiling on mouse Unigene I arrays (Incyte Genomics, Inc.). Genes that were either upregulated or downregulated by greater than two-fold in comparisons of apoE–/– mice on varying diets to apoE–/– mice on normal chow diet for three months, were identified and examined. A preponderance of the differentially expressed genes identified were involved in inflammation and fibrosis, including: the small inducible cytokines, such as MCP-1, MCP-2 and MIP; complement factors; interleukins; cathepsins; MMP 2 and MMP 12; and TGF-β. A number of small inducible cytokines were examined in more detail, including Fractalike. (SIC D1), MIP 1 (SIC A3), MCP-1, MCP-2 (SIC A8), IL-8 like (SIC A6), MCP-3 (SIC A7), PDGF-inducible (SIC A2), and RANTES (SIC A5). When relative array-based expression data was examined for all of the supra listed cytokines, all cytokines other than RANTES exhibited increases in relative expression levels as atherosclerosis progressed in both normal chow diet and western type diet apoE–/– mice.

Analysis of MCP-1 RNA and protein levels revealed a marked increase in both levels in ApoE–/– mice fed Wester chow. Elevated MCP-1 transcript levels during atherosclerosis progression produced corresponding increases in levels of MCP-1 protein, as detected in aortic arch tissue. While MCP-1 protein was not detectable in serum for any mice examined via array-based expression profiling, MCP-1 levels of about 60 pg/ml were observed for apoE−/− mice fed a western type diet for 4.5 months, and about 100 pg/ml levels of MCP-1 protein were observed for apoE−/− mice fed a western type diet for six months.

VI. Crystallization and Structural Determination of MCP-1-11K2-Fab

Example 30

Crystal Structure of 11K2

A three-dimensional structure of acomplex of a Fab fragment of murine 11K2 antibody with MCP-1 was determined by X-ray crystallography. The Fab fragment was produced by proteolytic cleavage. 1 mg of human MCP-1 and 1 mg of murine 11K2 Fab was mixed and concentrated to 8 mg/ml. Equal volumes of protein and well solution ($10^{-15}$% PEG 4000, 100 mM HEPES pH=7.5, 30 mM glycl-glycl-glycine) were combined and placed at room temperature to equilibrate. Crystals appeared within 3 days and grew to full size within 2 weeks. Crystals were flash-frozen for data collection, using liquid nitrogen in a solution containing 100 mM HEPES pH=7.5, 15% PEG 4000, 30 mM glycl-glycl-glycine and 25% glycerol. Crystal transfer to the cryoprotection solution was necessary to preserve the crystal during cooling to −180° C. for data collection, and also to allow compounds to bind under low salt conditions, which is important to increase the solubility of the compounds and to remove the sulfate ion bound in the active site (placed by crystallization conditions, but removable upon soaking for several days).

Data collection was performed on a rotating anode X-ray generator for a duration of typically about 6 hours, using 1 degree of oscillation and 5 minute exposure times. An oscillation range of 60 degrees was required for a complete data set. The space group of the crystals was determined to be $C222_1$ with unit cell dimensions a=86.36 Å, b=89.10 Å, c=176.24 Å. In 22,774 unique reflections (542,403 total reflections), resolution limits were determined to be 50 to 2.5 Å (2.59-2.50 Å). Results from the data collection are described below in Table 23.

TABLE 23

Data collection - phasing and model refinement

Resolution limits: 50-2.5 Å (2.59-2.50 Å)
Number of total reflections: 542,403
Number of unique reflections: 22,774
Redundancy: 6.2
I/σ: 13.2 (3.3)
$R_{merge}$: 0.090 (0.436)
Completeness: 99.8% (99.9%)
R-factor/Rfree: 0.219/0.277
reflections for refinement: 23911

Structure was solved by molecular replacement with Fab model. After an initial round of refinement, MCP-1 was clearly visible in 2Fo-Fc maps. The final model contains residues 4-71 of MCP-1, 1-214 of the light chain of 11K2, 1-217 of the heavy chain of 11K2, and 43 water molecules. Crystal structure results revealed that the residue contacts of MCP-1 which the heavy chain of 11K2 binds include R30, T32, S34, K38, E39, V41, P55, K56, Q61, M64. Analysis of the crystal structure also revealed that the light chain of 11K2 contacts residues D65, D68, K69 of MCP-1. Thus, 11K2 binds a discontinuous sequence of MCP-1.

Forming part of the present disclosure is the appended Sequence Listing, the contents of which are summarized in the table below:

TABLE 24

Summary of sequences

| SEQ ID NO: | Description | Sequence Type |
|---|---|---|
| 1 | MCP-1 MRHAS motif | amino acid |
| 2 | MCP-3 MRHAS motif | amino acid |
| 3 | 1A1 Heavy Chain cDNA Primer | nucleic acid |
| 4 | 1A1 Light Chain cDNA Primer | nucleic acid |
| 5 | 1A1 Heavy Chain cDNA primer | nucleic acid |
| 6 | 1A1 Heavy Chain cDNA primer | nucleic acid |
| 7 | 1A1 Light Chain cDNA primer | nucleic acid |
| 8 | 1A1 Light Chain cDNA primer | nucleic acid |
| 9 | 1A1 Heavy chain variable region | nucleic acid |
| 10 | 1A1 Light chain variable region | nucleic acid |
| 11 | 1A1 Heavy chain variable region | amino acid |
| 12 | 1A1 Light chain variable region | amino acid |
| 13 | 1A1 Heavy Chain Variable Region CDR1 | amino acid |
| 14 | 1A1 Heavy Chain Variable Region CDR2 | amino acid |
| 15 | 1A1 Heavy Chain Variable Region CDR3 | amino acid |
| 16 | 1A1 Light Chain Variable Region CDR1 | amino acid |
| 17 | 1A1 Light Chain Variable Region CDR2 | amino acid |
| 18 | 1A1 Light Chain Variable Region CDR3 | amino acid |
| 19 | 11K2 Heavy Chain cDNA Primer | nucleic acid |
| 20 | 11K2 Light Chain cDNA Primer | nucleic acid |
| 21 | 11K2 Heavy Chain cDNA Primer | nucleic acid |
| 22 | 11K2 Heavy Chain cDNA Primer | nucleic acid |
| 23 | 11K2 Light Chain cDNA Primer | nucleic acid |
| 24 | 11K2 Light Chain cDNA Primer | nucleic acid |
| 25 | 11K2 Heavy Chain Variable Region | nucleic acid |
| 26 | 11K2 Light Chain Variable Region | nucleic acid |
| 27 | 11K2 heavy chain variable region | amino acid |
| 28 | 11K2 light chain variable region | amino acid |
| 29 | 11K2 Heavy Chain Variable Region CDR1 | amino acid |
| 30 | 11K2 Heavy Chain Variable Region CDR2 | amino acid |
| 31 | 11K2 Heavy Chain Variable Region CDR3 | amino acid |
| 32 | 11K2 Light Chain Variable Region CDR1 | amino acid |
| 33 | 11K2 Light Chain Variable Region CDR2 | amino acid |
| 34 | 11K2 Light Chain Variable Region CDR3 | amino acid |
| 35 | 11K2 heavy chain chimera | nucleic acid |
| 36 | 11K2 light chain chimera | nucleic acid |
| 37 | 11K2 heavy chain chimera | amino acid |
| 38 | 11K2 light chain chimera | amino acid |
| 39 | 11K2 humanized heavy chain, version 1 (includes constant region) | nucleic acid |
| 40 | 11K2 humanized heavy chain, version 1 (includes constant region) | amino acid |
| 41 | 11K2 humanized heavy chain, version 2 (includes constant region) | nucleic acid |
| 42 | 11K2 humanized heavy chain, version 2 (includes constant region) | amino acid |
| 43 | 11K2 humanized light chain, version 1 (includes constant region) | nucleic acid |
| 44 | 11K2 humanized light chain, version 1 (includes constant region) | amino acid |
| 45 | 11K2 humanized light chain, version 2 (includes constant region) | nucleic acid |
| 46 | 11K2 humanized light chain, version 2 (includes constant region) | amino acid |
| 47 | Humanized 11K2 heavy chain, variable, version 1 | amino acid |
| 48 | Humanized 11K2 heavy chain, variable, v2 | amino acid |
| 49 | Humanized 11K2 light chain, variable, v1 | amino acid |
| 50 | Humanized 11K2 light chain, variable, v2 | amino acid |
| 51 | Chimera, variable heavy chain 1A1 | amino acid |
| 52 | Chimera, variable light chain 1A1 | amino acid |
| 53 | Humanized 1A1 heavy chain, variable v1 | amino acid |
| 54 | Humanized 1A1 heavy chain, variable v2 | amino acid |
| 55 | Humanized 1A1 light chain, variable v1 | amino acid |
| 56 | Humanized 1A1 light chain, variable v2 | amino acid |

TABLE 24-continued

Summary of sequences

| SEQ ID NO: | Description | Sequence Type |
|---|---|---|
| 57 | v1 light chain primer | nucleic acid |
| 58 | v1 light chain primer | nucleic acid |
| 59 | v1 light chain primer | nucleic acid |
| 60 | v1 light chain primer | nucleic acid |
| 61 | v2 light chain primer | nucleic acid |
| 62 | v1 heavy chain primer | nucleic acid |
| 63 | v1 heavy chain primer | nucleic acid |
| 64 | v1 heavy chain primer | nucleic acid |
| 65 | v1 heavy chain primer | nucleic acid |
| 66 | v1 heavy chain primer | nucleic acid |
| 67 | v2 heavy chain primer | nucleic acid |
| 68 | v2 heavy chain primer | nucleic acid |
| 69 | v2 heavy chain primer | nucleic acid |

One of ordinary skill in the art will recognize that many variations and changes may be made to the invention as described in the Detailed Description without departing from the spirit and scope of the invention. The examples provided herein are merely illustrative, and should not be construed as limiting of the scope of the invention, which is set forth in the appended claims.

We claim:

1. A humanized immunoglobulin or antigen-binding fragment thereof comprising a) heavy chain complementarity determining regions as set forth in SEQ ID NO:29, SEQ ID NO:30, and SEQ ID NO:31, and b) light chain complementarity determining regions as set forth in SEQ ID NO:32, SEQ ID NO:33, and SEQ ID NO:34.

2. The humanized immunoglobulin or antigen-binding fragment of claim 1, wherein the heavy chain further comprises variable region framework residues L27, I29, and T73 (Kabat numbering convention) from the monoclonal antibody 11K2 heavy chain as set forth in SEQ ID NO:27.

3. The humanized immunoglobulin or antigen-binding fragment of claim 1, wherein the heavy chain further comprises least one variable region framework residue selected from the group consisting of N28, K30, I48, and A67 (Kabat numbering convention) from the monoclonal antibody 11K2 heavy chain as set forth in SEQ ID NO:27.

4. The humanized immunoglobulin or antigen-binding fragment of claim 1, wherein the heavy chain further comprises variable region framework residues N28, K30, I48, and A67 (Kabat numbering convention) from the monoclonal antibody 11K2 heavy chain as set forth in SEQ ID NO:27.

5. The humanized immunoglobulin or antigen-binding fragment of claim 1, wherein the light chain further comprises at least one variable region framework residue from the monoclonal antibody 11K2 light chain set forth as SEQ ID NO: 28, wherein the residue is selected from the group consisting of S49 and Y71 (Kabat numbering convention), and wherein the remainder of the light chain is from a human immunoglobulin.

6. The humanized immunoglobulin or antigen-binding fragment of claim 1, wherein the light chain further comprises variable region framework residues S49 and Y71 (Kabat numbering convention) from the monoclonal antibody 11K2 light chain as set forth in SEQ ID NO:28.

7. The humanized immunoglobulin or antigen-binding fragment of claim 6, wherein the light chain further comprises variable region framework residue K69 (Kabat numbering convention) from the monoclonal antibody 11K2 light chain as set forth in SEQ ID NO:28.

8. The humanized immunoglobulin or antigen-binding fragment of claim 1, wherein the heavy chain further comprises at least one variable region framework residue from the monoclonal antibody 11K2 heavy chain set forth as SEQ ID NO: 27, wherein the residue is selected from the group consisting of L27, N28, I29, K30, I48, A67, and T73 (Kabat numbering).

9. The humanized immunoglobulin or antigen-binding fragment of claim 8, wherein the heavy chain comprises variable region framework residues L27, N28, I29, K30, I48, A67, and T73 (Kabat numbering convention) from the monoclonal antibody 11K2 heavy chain as set forth in SEQ ID NO:27.

10. The humanized immunoglobulin or antigen-binding fragment of claim 6, wherein the heavy chain comprises at least one variable region framework residues L27, I29, and T73 (Kabat numbering convention) from the monoclonal antibody 11K2 heavy chain as set forth in SEQ ID NO:27.

11. The humanized immunoglobulin or antigen-binding fragment of claim 9, wherein the light chain comprises at least one variable region framework residue from the monoclonal antibody 11K2 light chain set forth as SEQ ID NO: 28, wherein the residue is selected from the group consisting of S49, K69, and Y71 (Kabat numbering).

12. The humanized immunoglobulin or antigen-binding fragment of claim 1, wherein the heavy chain comprises at least one variable region framework residue from the monoclonal antibody 11K2 heavy chain set forth as SEQ ID NO: 27, wherein the residue is selected from the group consisting of L27, N28, I29, K30, I48, A67 and T73 (Kabat numbering convention), and the light chain comprises at least one variable region framework residue from the monoclonal antibody 11K2 light chain set forth as SEQ ID NO: 28, wherein the residue is selected from the group consisting of S49, K69, and Y71 (Kabat numbering convention), wherein the remainder of the heavy and light chains are from a human immunoglobulin.

13. The humanized immunoglobulin or antigen-binding fragment of claim 12, wherein the heavy chain comprises variable region framework residues L27, I29, and T73, and the light chain comprises variable region framework residues S49 and Y71.

14. The humanized immunoglobulin or antigen-binding fragment of claim 12, wherein the heavy chain comprises variable region framework residues L27, I29, and T73, and the light chain comprises variable region framework residues S49, K69, and Y71.

15. The humanized immunoglobulin or antigen-binding fragment of claim 12, wherein the heavy chain comprises variable region framework residues L27, N28, I29, K30, I48, A67 and T73, and the light chain comprises variable region framework residues S49 and Y71.

16. A humanized immunoglobulin or antigen-binding fragment comprising a) heavy chain complementary determining regions as set forth in SEQ ID NO: 29, SEQ ID NO: 30, and SEQ ID NO: 31, and variable region framework residues L27, N28, I29, K30, I48, A67, and T73 (Kabat numbering) from the monoclonal antibody 11K2 heavy chain set forth as SEQ ID NO: 27, and b) light chain complementary determining regions as set forth in SEQ ID NO: 32, SEQ ID NO: 33, and SEQ ID NO: 34, and variable region framework residues S49, K69, and Y71 (Kabat numbering) from the monoclonal antibody 11K2 light chain set forth as SEQ ID NO: 28, wherein the remainder of the heavy and light chains are from a human immunoglobulin.

17. The immunoglobulin or antigen-binding fragment of claim 16, wherein the immunoglobulin is modified by reducing or eliminating at least one potential glycosylation site.

18. The immunoglobulin or antigen-binding fragment of claim 1, which binds to MCP-1.

19. The immunoglobulin or antigen-binding fragment of claim 1, which specifically binds to MCP-1 with a binding affinity of at least $10^{-9}$ M.

20. The immunoglobulin or antigen-binding fragment of claim 1, which specifically binds to MCP-1 with a binding affinity of at least $10^{-10}$ M.

21. The immunoglobulin or antigen-binding fragment of claim 1, which specifically binds to MCP-1 with a binding affinity of at least $10^{-11}$ M.

22. The immunoglobulin or antigen-binding fragment of claim 1, which further binds to MCP-2 with a binding affinity of at least $10^{-7}$ M.

23. The immunoglobulin or antigen-binding fragment of claim 1, which further binds to MCP-2 with a binding affinity of at least $10^{-8}$ M.

24. The immunoglobulin or antigen-binding fragment of claim 1, which further binds to MCP-2 with a binding affinity of at least $10^{-9}$ M.

25. The immunoglobulin or antigen-binding fragment of claim 1, which binds to MCP-2.

26. The immunoglobulin or antigen-binding fragment of claim 1, which specifically binds to MCP-2 with a binding affinity of at least $10^{-7}$ M.

27. The immunoglobulin or antigen-binding fragment of claim 1, which specifically binds to MCP-2 with a binding affinity of at least $10^{-8}$ M.

28. The immunoglobulin or antigen-binding fragment of claim 1, which specifically binds to MCP-2 with a binding affinity of at least $10^{-9}$ M.

29. The immunoglobulin or antigen-binding fragment of claim 1, which binds to MCP-1 and MCP-2.

30. The immunoglobulin or antigen-binding fragment of claim 1, which binds to an epitope within MCP-1, MCP-2, and MCP-3.

31. An antibody comprising the same heavy and light chain polypeptide sequences as an antibody produced by clone 3F2 (ATCC patent deposit designation PTA-5308).

32. An immunoglobulin or antigen-binding fragment of claim 1, wherein the heavy chain isotype is gamma 1.

33. An immunoglobulin or antigen-binding fragment of claim 1, wherein the antibody is modified by reducing or eliminating at least one potential glycosylation site.

34. An immunoglobulin or antigen-binding fragment of claim 1, wherein the antibody is modified by conjugation to a carrier selected from polyethylene glycol and albumen.

35. An antibody or antigen-binding fragment of claim 1, wherein the constant region of the antibody is modified to reduce at least one constant region-mediated biological effector function relative to an unmodified antibody.

36. A fragment of claim 1, wherein the fragment is a Fab fragment.

37. An immunoglobulin or antigen-binding fragment of claim 1, which inhibits MCP-induced chemotaxis.

38. An immunoglobulin or antigen-binding fragment of claim 37, wherein the immunoglobulin or antigen-binding fragment inhibits MCP-1-induced chemotaxis, MCP-2-induced chemotaxis, or both MCP-1-induced and MCP-2-induced chemotaxis.

39. An immunoglobulin or antigen-binding fragment of claim 1, which inhibits MCP-induced collagen expression.

40. An immunoglobulin or antigen-binding fragment of claim 39, wherein the immunoglobulin or antigen-binding fragment inhibits MCP-1-induced collagen expression, MCP-2-induced collagen expression, or both MCP-1-induced and MCP-2-induced collagen expression.

41. An immunoglobulin or antigen-binding fragment of claim 1, which inhibits MCP-1 induced angiogenesis.

42. An immunoglobulin or antigen-binding fragment of claim 41, wherein the immunoglobulin or antigen-binding fragment inhibits MCP-1-induced angiogenesis, MCP-2-induced angiogenesis, or both MCP-1-induced and MCP-2-induced angiogenesis.

43. An immunoglobulin or antigen-binding fragment of claim 1, which reduces inflammation in a subject.

44. The immunoglobulin or antigen-binding fragment of claim 43, wherein the inflammation is associated with a disorder selected from the group consisting of arthritis, multiple sclerosis, cirrhosis, atherosclerosis, and breast carcinoma.

45. An immunoglobulin or antigen-binding fragment of claim 1, which reduces fibrosis in a subject.

46. A pharmaceutical composition comprising the immunoglobulin or antigen-binding fragment of claim 1 and a pharmaceutical carrier.

* * * * *

UNITED STATES PATENT AND TRADEMARK OFFICE
CERTIFICATE OF CORRECTION

| | | |
|---|---|---|
| PATENT NO. | : 7,888,479 B2 | Page 1 of 1 |
| APPLICATION NO. | : 10/536067 | |
| DATED | : February 15, 2011 | |
| INVENTOR(S) | : Antonin R. De Fougerolles et al. | |

It is certified that error appears in the above-identified patent and that said Letters Patent is hereby corrected as shown below:

Title Page, item (54);
Title, change "Chemotactric" to "Chemotactic"

Signed and Sealed this
Third Day of May, 2011

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,888,479 B2 |
| APPLICATION NO. | : 10/536067 |
| DATED | : February 15, 2011 |
| INVENTOR(S) | : Antonin R. De Fougerolles et al. |

It is certified that error appears in the above-identified patent and that said Letters Patent is hereby corrected as shown below:

Title Page, item (54) and at Column 1, line 2;
Title, change "Chemotactric" to "Chemotactic"

This certificate supersedes the Certificate of Correction issued May 3, 2011.

Signed and Sealed this
Thirty-first Day of May, 2011

David J. Kappos
*Director of the United States Patent and Trademark Office*

SEQUENCE LISTING

```
<160> NUMBER OF SEQ ID NOS: 69

<210> SEQ ID NO 1
<211> LENGTH: 7
<212> TYPE: PRT
<213> ORGANISM: Homo sapiens

<400> SEQUENCE: 1

Gln Thr Gln Thr Pro Lys Thr
1               5

<210> SEQ ID NO 2
<211> LENGTH: 7
<212> TYPE: PRT
<213> ORGANISM: Homo sapiens

<400> SEQUENCE: 2

Lys Thr Gln Thr Pro Lys Leu
1               5

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
aggtctagaa yctccacaca caggrrccag tggatagac                           39

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
gcgtctagaa ctggatggtg ggagatgga                                      29

<210> SEQ ID NO 5
<211> LENGTH: 22
<212> TYPE: DNA
<213> ORGANISM: Artificial Sequence
<220> FEATURE:
<223> OTHER INFORMATION: Primer
```

<400> SEQUENCE: 5
aggtsmarct gcagsagtcw gg                                                    22

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
tgaggagacg gtgaccgtgg tcccttggcc cc                                         32

<210> SEQ ID NO 7
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 15
<223> OTHER INFORMATION: n = A,T,C or G

<400> SEQUENCE: 7
gayathcara tgacncag                                                         18

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
gcgtctagaa ctggatggtg ggagatgga                                             29

<210> SEQ ID NO 9
<211> LENGTH: 366
<212> TYPE: DNA
<213> ORGANISM: Mus musculus

<400> SEQUENCE: 9
gaggtccagc tgcagcagtc tggggcagaa cttgtgaggt caggggcctc agtcaagttg           60
tcctgcacag cttctggctt caacattaaa gacaactata tgcactgggt gaagcagagg          120
cctgaacagg gcctggagtg gattggatgg attgatcctg agaatggaga tactgaatat          180
gccccgaagt tccagggcaa ggccactatg actgcagaca catcctccaa cacagcctac          240
ctgcagctca gcagcctgac atctgaggac actgccgtct attactgtaa tacatgggct          300
tactacggta ctagctacgg gggatttgct tactggggcc aagggaccac ggtcaccgtc          360
tcctca                                                                    366

<210> SEQ ID NO 10
<211> LENGTH: 336
<212> TYPE: DNA
<213> ORGANISM: Mus musculus

<400> SEQUENCE: 10
gatatccaga tgactcagac tccactcact ttgtcggtta ccattggaca accagcctcc           60
atctcttgca agtcaagtca gagcctctta gatagtgatg gaaagacata tttgaattgg          120

```
tcgttacaga ggccaggcca gtctccaaag cgcctaatct atctggtgtc taaactggac      180
tctggagtcc ctgacaggtt cactggcagt ggatcaggga cagatttcac actgaaaatc      240
agcagagtgg aggctgagga tttgggagtt tattattgct ggcaaggtac acattttcct      300
cagacgttcg gtggaggcac caagctggag atcaaa                                336
```

```
<210> SEQ ID NO 11
<211> LENGTH: 122
<212> TYPE: PRT
<213> ORGANISM: Mus musculus

<400> SEQUENCE: 11

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Asn
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Thr Trp Ala Tyr Tyr Gly Ser Tyr Gly Gly Phe Ala Tyr Trp
            100                 105                 110

Gly Gln Gly Thr Thr Val Thr Val Ser Ser
        115                 120

<210> SEQ ID NO 12
<211> LENGTH: 112
<212> TYPE: PRT
<213> ORGANISM: Mus musculus

<400> SEQUENCE: 12

Asp Ile Gln Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Ser Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 13
<211> LENGTH: 5
<212> TYPE: PRT
<213> ORGANISM: Mus musculus

<400> SEQUENCE: 13

Asp Asn Tyr Met His
1               5
```

```
<210> SEQ ID NO 14
<211> LENGTH: 17
<212> TYPE: PRT
<213> ORGANISM: Mus musculus

<400> SEQUENCE: 14

Trp Ile Asp Pro Glu Asn Gly Asp Thr Glu Tyr Ala Pro Lys Phe Gln
 1               5                  10                  15
Gly

<210> SEQ ID NO 15
<211> LENGTH: 13
<212> TYPE: PRT
<213> ORGANISM: Mus musculus

<400> SEQUENCE: 15

Trp Ala Tyr Tyr Gly Thr Ser Tyr Gly Gly Phe Ala Tyr
 1               5                  10

<210> SEQ ID NO 16
<211> LENGTH: 16
<212> TYPE: PRT
<213> ORGANISM: Mus musculus

<400> SEQUENCE: 16

Lys Ser Ser Gln Ser Leu Leu Asp Ser Asp Gly Lys Thr Tyr Leu Asn
 1               5                  10                  15

<210> SEQ ID NO 17
<211> LENGTH: 7
<212> TYPE: PRT
<213> ORGANISM: Mus musculus

<400> SEQUENCE: 17

Leu Val Ser Lys Leu Asp Ser
 1               5

<210> SEQ ID NO 18
<211> LENGTH: 9
<212> TYPE: PRT
<213> ORGANISM: Mus musculus

<400> SEQUENCE: 18

Trp Gln Gly Thr His Phe Pro Gln Thr
 1               5

<210> SEQ ID NO 19
<211> LENGTH: 39
<212> TYPE: DNA
<213> ORGANISM: Artificial Sequence
<220> FEATURE:
<223> OTHER INFORMATION: Primer

<400> SEQUENCE: 19
aggtctagaa yctccacaca caggrrccag tggatagac                             39

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
```

```
gcgtctagaa ctggatggtg ggagatgga                                              29

<210> SEQ ID NO 21
<211> LENGTH: 39
<212> TYPE: DNA
<213> ORGANISM: Artificial Sequence
<220> FEATURE:
<223> OTHER INFORMATION: Primer

<400> SEQUENCE: 21
ggggatatcc accatggrat gsagctgkgt matsctctt                                   39

<210> SEQ ID NO 22
<211> LENGTH: 39
<212> TYPE: DNA
<213> ORGANISM: Artificial Sequence
<220> FEATURE:
<223> OTHER INFORMATION: Primer

<400> SEQUENCE: 22
aggtctagaa yctccacaca caggrrccag tggatagac                                   39

<210> SEQ ID NO 23
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 15
<223> OTHER INFORMATION: n = A,T,C or G

<400> SEQUENCE: 23
gayathcara tgacncag                                                          18

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
gcgtctagaa ctggatggtg ggagatgga                                              29

<210> SEQ ID NO 25
<211> LENGTH: 351
<212> TYPE: DNA
<213> ORGANISM: Mus musculus

<400> SEQUENCE: 25
gaggttcagc tgcagcagtc tggggcagag cttgtgaagg caggggcctc agtcaagttg            60
tcctgcccag cttctggcct caacattaaa gacacctata tgcactgggt gaagcagagg           120
cctgaacagg gcctggagtg gattggaagg attgatcctg cgaatggtaa tactaaattt           180 gaccccgaagt tccagggcaa ggccactata acagcagaca catcctccaa cacagcctac          240
ctgcagctca gcagcctgac atctgaggac actgccgtct attactgtgc tagaggcgtc           300
tttggctttt ttgactactg gggccaaggc accactctca cagtctcctc a                    351

<210> SEQ ID NO 26
<211> LENGTH: 321
<212> TYPE: DNA
```

<213> ORGANISM: Mus musculus

<400> SEQUENCE: 26

```
gacattcaga tgactcagtc ttcatcctcc ttttctgtat ctctaggaga cagagtcacc      60
attacttgca aggcaactga ggacatatat aatcgattag cctggtatca gcagaaacca     120
ggaagtgctc ctaggctctt aatttctggt gcaaccagtt tggagactgg ggttccttca     180
agattcagtg gcagtggatc tggaaaagat tacactctca gcattaccag tcttcagact     240
gaggatgttg ctacttatta ctgtcaacag ttttggagtg ctccgtacac gttcggaggg     300
gggaccaagc tggagatcaa a                                               321
```

<210> SEQ ID NO 27
<211> LENGTH: 117
<212> TYPE: PRT
<213> ORGANISM: Mus musculus

<400> SEQUENCE: 27

Glu Val Gln Leu Gln Gln Ser Gly Ala Glu Leu Val Lys Ala Gly Ala
1               5                   10                  15

Ser Val Lys Leu Ser Cys Pro Ala Ser Gly Leu Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Val Phe Gly Phe Phe Asp Tyr Trp Gly Gln Gly Thr Thr
            100                 105                 110

Leu Thr Val Ser Ser
        115

<210> SEQ ID NO 28
<211> LENGTH: 107
<212> TYPE: PRT
<213> ORGANISM: Mus musculus

<400> SEQUENCE: 28

Asp Ile Gln Met Thr Gln Ser Ser Ser Phe Ser Val Ser Leu Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Ser Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Phe Trp Ser Ala Pro Tyr
                85                  90                  95

Thr Phe Gly Gly Gly Thr Lys Leu Glu Ile Lys
            100                 105

<210> SEQ ID NO 29

```
<211> LENGTH: 5
<212> TYPE: PRT
<213> ORGANISM: Mus musculus

<400> SEQUENCE: 29

Asp Thr Tyr Met His
 1               5

<210> SEQ ID NO 30
<211> LENGTH: 17
<212> TYPE: PRT
<213> ORGANISM: Mus musculus

<400> SEQUENCE: 30

Arg Ile Asp Pro Ala Asn Gly Asn Thr Lys Phe Asp Pro Lys Phe Gln
 1               5                  10                  15

Gly

<210> SEQ ID NO 31
<211> LENGTH: 8
<212> TYPE: PRT
<213> ORGANISM: Mus musculus

<400> SEQUENCE: 31

Gly Val Phe Gly Phe Phe Asp Tyr
 1               5

<210> SEQ ID NO 32
<211> LENGTH: 11
<212> TYPE: PRT
<213> ORGANISM: Mus musculus

<400> SEQUENCE: 32

Lys Ala Thr Glu Asp Ile Tyr Asn Arg Leu Ala
 1               5                  10

<210> SEQ ID NO 33
<211> LENGTH: 7
<212> TYPE: PRT
<213> ORGANISM: Mus musculus

<400> SEQUENCE: 33

Gly Ala Thr Ser Leu Glu Thr
 1               5

<210> SEQ ID NO 34
<211> LENGTH: 9
<212> TYPE: PRT
<213> ORGANISM: Mus musculus

<400> SEQUENCE: 34

Gln Gln Phe Trp Ser Ala Pro Tyr Thr
 1               5

<210> SEQ ID NO 35
<211> LENGTH: 1344
<212> TYPE: DNA
<213> ORGANISM: Artificial Sequence
<220> FEATURE:
<223> OTHER INFORMATION: Chimeric sequence

<400> SEQUENCE: 35
gaggttcagc tgcagcagtc tggggcagag cttgtgaagg caggggcctc agtcaagttg     60
tcctgcccag cttctggcct caacattaaa gacacctata tgcactgggt gaagcagagg    120
```

```
cctgaacagg gcctggagtg gattggaagg attgatcctg cgaatggtaa tactaaattt     180
gacccgaagt tccagggcaa ggccactata acagcagaca catcctccaa cacagcctac     240
ctgcagctca gcagcctgac atctgaggac actgccgtct attactgtgc tagaggcgtc     300
tttggctttt ttgactactg gggccaaggt accactctca cagtctcctc agcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660 gacaagactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gttggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctcccgggaa atga                                           1344
```

<210> SEQ ID NO 36
<211> LENGTH: 645
<212> TYPE: DNA
<213> ORGANISM: Artificial Sequence
<220> FEATURE:
<223> OTHER INFORMATION: Chimeric sequence

<400> SEQUENCE: 36

```
gacattcaga tgactcagtc ttcatcctcc tttttctgtat ctctaggaga cagagtcacc     60
attacttgca aggcaactga ggacatatat aatcgattag cctggtatca gcagaaacca    120
ggaagtgctc ctaggctctt aatttctggt gcaaccagtt tggagactgg ggttccttca    180
agattcagtg gcagtggatc tggaaaagat tacactctca gcattaccag tcttcagact    240
gaggatgttg ctacttatta ctgtcaacag ttttggagtg ctccgtacac gttcggaggg    300
gggaccaagc tggagatcaa cgaactgtgc tgcaccat ctgtcttcat cttcccgcca     360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 37
<211> LENGTH: 447
<212> TYPE: PRT

<210> ORGANISM: Artificial Sequence
<220> FEATURE:
<223> OTHER INFORMATION: Chimeric sequence

<400> SEQUENCE: 37

```
Glu Val Gln Leu Gln Gln Ser Gly Ala Glu Leu Val Lys Ala Gly Ala
 1               5                  10                  15

Ser Val Lys Leu Ser Cys Pro Ala Ser Gly Leu Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Val Phe Gly Phe Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 38
<211> LENGTH: 214
<212> TYPE: PRT
<213> ORGANISM: Artificial Sequence
<220> FEATURE:
<223> OTHER INFORMATION: Chimeric sequence

<400> SEQUENCE: 38

Asp Ile Gln Met Thr Gln Ser Ser Ser Phe Ser Val Ser Leu Gly
 1               5                  10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Ser Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Phe Trp Ser Ala Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 1344
<212> TYPE: DNA
<213> ORGANISM: Artificial Sequence
<220> FEATURE:
<223> OTHER INFORMATION: humanized antibody

<400> SEQUENCE: 39
caggttcagc tggtgcagtc tggggcagag gtgaagaagc ccgggtcctc agtcaaggtc      60
tcctgcaagg cttctggcct caacattaaa gacacctata tgcactgggt gcgacaggcg     120
cctggacagg gcctggagtg gattggaagg attgatcctg cgaatggtaa tactaaattt     180
```

-continued

```
gacccgaagt tccagggcag agccactata acagcagaca catccacgag cacagcctac    240
atggagctca gcagcctgag atctgaggac actgccgtct attactgtgc tagaggcgtc    300
tttggctttt ttgactactg gggccaaggg accactgtga cagtctcctc agcctccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt     660 gacaagactc acacatgccc accgtgccca gcacctgaac tcctgggggg accgtcagtc    720
ttcctcttcc cccaaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc ccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gttggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggaaa atga                                         1344
```

<210> SEQ ID NO 40
<211> LENGTH: 447
<212> TYPE: PRT
<213> ORGANISM: Artificial Sequence
<220> FEATURE:
<223> OTHER INFORMATION: humanized antibody

<400> SEQUENCE: 40

```
Gln Val Gln Leu Val Gln Ser Gly Ala Glu Val Lys Lys Pro Gly Ser
  1               5                  10                  15

Ser Val Lys Val Ser Cys Lys Ala Ser Gly Leu Asn Ile Lys Asp Thr
             20                  25                  30

Tyr Met His Trp Val Arg Gln Ala Pro Gly Gln Gly Leu Glu Trp Ile
         35                  40                  45

Gly Arg Ile Asp Pro Ala Asn Gly Asn Thr Lys Phe Asp Pro Lys Phe
     50                  55                  60

Gln Gly Arg Ala Thr Ile Thr Ala Asp Thr Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Val Phe Gly Phe Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 1344
<212> TYPE: DNA
<213> ORGANISM: Artificial Sequence
<220> FEATURE:
<223> OTHER INFORMATION: humanized antibody

<400> SEQUENCE: 41
caggttcagc tggtgcagtc tggggcagag gtgaagaagc ccggggtcctc agtcaaggtc      60 tcctgcaagg cttcaggcct caccattagc gacacctata tgcactgggt gcgacaggcg     120
cctggacagg gcctcgagtg gatgggaagg attgatcctg cgaatggtaa tactaaattt     180
gacccgaagt tccagggcag agtcactata actgcagaca catccacgag cacagcctac     240
atggagctca gcagcctgag atctgaggac actgccgtct attactgtgc tagaggcgtc     300
tttggctttt ttgactactg gggccaaggg accactgtga cagtctcctc agcctccacc     360
aagggcccat cggtcttccc cctggcaccc tcctccaaga gcacctctgg gggcacagcg     420

-continued

```
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagccc caaatcttgt      660
gacaagactc acacatgccc accgtgccca gcacctgaac tcctgggggg accgtcagtc      720
ttcctcttcc cccaaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggatga gctgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gttggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctcccgggaa atga                                            1344
```

<210> SEQ ID NO 42
<211> LENGTH: 447
<212> TYPE: PRT
<213> ORGANISM: Artificial Sequence
<220> FEATURE:
<223> OTHER INFORMATION: humanized antibody

<400> SEQUENCE: 42

```
Gln Val Gln Leu Val Gln Ser Gly Ala Glu Val Lys Lys Pro Gly Ser
 1               5                   10                  15

Ser Val Lys Val Ser Cys Lys Ala Ser Gly Leu Thr Ile Ser Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Thr Lys Phe Asp Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
                195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 43
<211> LENGTH: 645
<212> TYPE: DNA
<213> ORGANISM: Artificial Sequence
<220> FEATURE:
<223> OTHER INFORMATION: humanized antibody

<400> SEQUENCE: 43
gacattcaga tgactcagtc tccatcctcc ctgtcagcat ctgtgggaga cagagtcacc      60
attacttgca aggcaactga ggacatatat aatcgattag cctggtatca gcagaaacca     120
ggaaaggccc ctaagctctt aatttctggt gcaaccagtt tggagactgg ggttccttca     180
agattcagtg gcagtggatc tggaaaagat tacactctca ccattagcag tctacagcct     240
gaggattttg ctacttatta ctgtcaacag ttttggagtg ctccgtacac gttcggaggg     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645
```

```
<210> SEQ ID NO 44
<211> LENGTH: 214
<212> TYPE: PRT
<213> ORGANISM: Artificial Sequence
<220> FEATURE:
<223> OTHER INFORMATION: humanized antibody

<400> SEQUENCE: 44
```

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |
| Asp | Arg | Val | Thr | Ile | Thr | Cys | Lys | Ala | Thr | Glu | Asp | Ile | Tyr | Asn | Arg |
| | | | 20 | | | | | 25 | | | | | 30 | | |
| Leu | Ala | Trp | Tyr | Gln | Gln | Lys | Pro | Gly | Lys | Ala | Pro | Lys | Leu | Leu | Ile |
| | | | 35 | | | | | 40 | | | | | 45 | | |
| Ser | Gly | Ala | Thr | Ser | Leu | Glu | Thr | Gly | Val | Pro | Ser | Arg | Phe | Ser | Gly |
| 50 | | | | | 55 | | | | | 60 | | | | | |
| Ser | Gly | Ser | Gly | Lys | Asp | Tyr | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | Phe | Trp | Ser | Ala | Pro | Tyr |
| | | | | 85 | | | | | 90 | | | | | 95 | |
| Thr | Phe | Gly | Gly | Gly | Thr | Lys | Val | Glu | Ile | Lys | Arg | Thr | Val | Ala | Ala |
| | | | | 100 | | | | | 105 | | | | | 110 | |
| Pro | Ser | Val | Phe | Ile | Phe | Pro | Pro | Ser | Asp | Glu | Gln | Leu | Lys | Ser | Gly |
| | | | 115 | | | | | 120 | | | | | 125 | | |
| Thr | Ala | Ser | Val | Val | Cys | Leu | Leu | Asn | Asn | Phe | Tyr | Pro | Arg | Glu | Ala |
| | | 130 | | | | | 135 | | | | | 140 | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |
| Ser | Thr | Leu | Thr | Leu | Ser | Lys | Ala | Asp | Tyr | Glu | Lys | His | Lys | Val | Tyr |
| | | | 180 | | | | | 185 | | | | | 190 | | |
| Ala | Cys | Glu | Val | Thr | His | Gln | Gly | Leu | Ser | Ser | Pro | Val | Thr | Lys | Ser |
| | | | 195 | | | | | 200 | | | | | 205 | | |
| Phe | Asn | Arg | Gly | Glu | Cys | | | | | | | | | | |
| 210 | | | | | | | | | | | | | | | |

```
<210> SEQ ID NO 45
<211> LENGTH: 645
<212> TYPE: DNA
<213> ORGANISM: Artificial Sequence
<220> FEATURE:
<223> OTHER INFORMATION: humanized antibody
<400> SEQUENCE: 45
gacattcaga tgactcagtc tccatcctcc ctgtcagcat ctgtgggaga cagagtcacc      60
attacttgca aggcaactga ggacatatat aatcgattag cctggtatca gcagaaacca     120
ggaaaggccc ctaagctctt aatttctggt gcaaccagtt tggagactgg ggttccttca     180
agattcagtg gcagtggatc tggaaaagat tacactctca ccattagcag tctacagcct     240
gaggattttg ctacttatta ctgtcaacag ttttggagtg ctccgtacac gttcggaggg     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacctgacg     540
```

```
ctgagcaaag cagactacga gaaacacaaa gtctacgcct gcgaagtcac ccatcagggc       600
ctgagctcgc ccgtcacaaa gagcttcaac aggggagagt gttag                      645
```

<210> SEQ ID NO 46
<211> LENGTH: 214
<212> TYPE: PRT
<213> ORGANISM: Artificial Sequence
<220> FEATURE:
<223> OTHER INFORMATION: humanized antibody

<400> SEQUENCE: 46

```
Asp Ile Gln Met Thr Gln Ser Pro Ser Ser Leu Ser Ala Ser Val Gly
  1               5                  10                  15

Asp Arg Val Thr Ile Thr Cys Lys Ala Thr Glu Asp Ile Tyr Asn Arg
             20                  25                  30

Leu Ala Trp Tyr Gln Gln Lys Pro Gly Lys Ala Pro Lys Leu Leu Ile
         35                  40                  45

Ser Gly Ala Thr Ser Leu Glu Thr Gly Val Pro Ser Arg Phe Ser Gly
     50                  55                  60

Ser Gly Ser Gly Lys Asp Tyr Thr Leu Thr Ile Ser Ser Leu Gln Pro
 65                  70                  75                  80

Glu Asp Phe Ala Thr Tyr Tyr Cys Gln Gln Phe Trp Ser Ala Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 47
<211> LENGTH: 117
<212> TYPE: PRT
<213> ORGANISM: Artificial Sequence
<220> FEATURE:
<223> OTHER INFORMATION: humanized 11k2 heavy chain

<400> SEQUENCE: 47

```
Gln Val Gln Leu Val Gln Ser Gly Ala Glu Val Lys Lys Pro Gly Ser
  1               5                  10                  15

Ser Val Lys Val Ser Cys Lys Ala Ser Gly Leu Asn Ile Lys Asp Thr
             20                  25                  30

Tyr Met His Trp Val Arg Gln Ala Pro Gly Gln Gly Leu Glu Trp Ile
         35                  40                  45

Gly Arg Ile Asp Pro Ala Asn Gly Asn Thr Lys Phe Asp Pro Lys Phe
     50                  55                  60
```

```
Gln Gly Arg Ala Thr Ile Thr Ala Asp Thr Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Val Phe Gly Phe Phe Asp Tyr Trp Gly Gln Gly Thr Thr
            100                 105                 110

Val Thr Val Ser Ser
        115

<210> SEQ ID NO 48
<211> LENGTH: 117
<212> TYPE: PRT
<213> ORGANISM: Artificial Sequence
<220> FEATURE:
<223> OTHER INFORMATION: humanized 11k2 heavy chain

<400> SEQUENCE: 48

Gln Val Gln Leu Val Gln Ser Gly Ala Glu Val Lys Lys Pro Gly Ser
  1               5                  10                  15

Ser Val Lys Val Ser Cys Lys Ala Ser Gly Leu Thr Ile Ser Asp Thr
                 20                  25                  30

Tyr Met His Trp Val Arg Gln Ala Pro Gly Gln Gly Leu Glu Trp Met
             35                  40                  45

Gly Arg Ile Asp Pro Ala Asn Gly Asn Thr Lys Phe Asp Pro Lys Phe
     50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Val Phe Gly Phe Phe Asp Tyr Trp Gly Gln Gly Thr Thr
            100                 105                 110

Val Thr Val Ser Ser
        115

<210> SEQ ID NO 49
<211> LENGTH: 107
<212> TYPE: PRT
<213> ORGANISM: Artificial Sequence
<220> FEATURE:
<223> OTHER INFORMATION: humanized 11k2 light chain

<400> SEQUENCE: 49

Asp Ile Gln Met Thr Gln Ser Pro Ser Ser Leu Ser Ala Ser Val Gly
  1               5                  10                  15

Asp Arg Val Thr Ile Thr Cys Lys Ala Thr Glu Asp Ile Tyr Asn Arg
                 20                  25                  30

Leu Ala Trp Tyr Gln Gln Lys Pro Gly Lys Ala Pro Lys Leu Leu Ile
             35                  40                  45

Ser Gly Ala Thr Ser Leu Glu Thr Gly Val Pro Ser Arg Phe Ser Gly
     50                  55                  60

Ser Gly Ser Gly Lys Asp Tyr Thr Leu Thr Ile Ser Ser Leu Gln Pro
 65                  70                  75                  80

Glu Asp Phe Ala Thr Tyr Tyr Cys Gln Gln Phe Trp Ser Ala Pro Tyr
                 85                  90                  95

Thr Phe Gly Gly Gly Thr Lys Val Glu Ile Lys
            100                 105

<210> SEQ ID NO 50
```

```
<211> LENGTH: 107
<212> TYPE: PRT
<213> ORGANISM: Artificial Sequence
<220> FEATURE:
<223> OTHER INFORMATION: humanized 11k2 light chain

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Trp Ser Ala Pro Tyr
                85                  90                  95

Thr Phe Gly Gly Gly Thr Lys Val Glu Ile Lys
            100                 105

<210> SEQ ID NO 51
<211> LENGTH: 122
<212> TYPE: PRT
<213> ORGANISM: Artificial Sequence
<220> FEATURE:
<223> OTHER INFORMATION: Chimeric sequence

<400> SEQUENCE: 51

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Asn
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Thr Trp Ala Tyr Tyr Gly Thr Ser Tyr Gly Gly Phe Ala Tyr Trp
            100                 105                 110

Gly Gln Gly Thr Thr Val Thr Arg Leu Leu
        115                 120

<210> SEQ ID NO 52
<211> LENGTH: 37
<212> TYPE: PRT
<213> ORGANISM: Artificial Sequence
<220> FEATURE:
<223> OTHER INFORMATION: chimeric sequence

<400> SEQUENCE: 52

Phe Thr Leu Lys Ile Ser Arg Val Glu Ala Glu Asp Leu Gly Val Tyr
1               5                   10                  15

Tyr Cys Trp Gln Gly Thr His Phe Pro Gln Thr Phe Gly Gly Gly Thr
            20                  25                  30
```

Lys Leu Glu Ile Lys
         35

<210> SEQ ID NO 53
<211> LENGTH: 119
<212> TYPE: PRT
<213> ORGANISM: Artificial Sequence
<220> FEATURE:
<223> OTHER INFORMATION: Humanized antibody

<400> SEQUENCE: 53

Gln Val Gln Leu Leu Glu Ser Gly Ala Glu Leu Val Arg Pro Gly Ser
 1               5                  10                  15

Ser Val Lys Ile Ser Cys Lys Ala Ser Gly Phe Asn Ile Lys Asp Asn
                20                  25                  30

Tyr Met His Trp Val Lys Gln Arg Pro Gly Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Gly Lys Ala Thr Met Thr Ala Asp Thr Ser Ser Asn Thr Ala Tyr
65                  70                  75                  80

Met Gln Leu Ser Gly Leu Thr Ser Glu Asp Ser Ala Val Tyr Tyr Cys
                85                  90                  95

Asn Thr Trp Ala Tyr Tyr Gly Thr Ser Tyr Gly Gly Phe Ala Tyr Trp
            100                 105                 110

Gly Gln Gly Thr Thr Val Thr
        115

<210> SEQ ID NO 54
<211> LENGTH: 119
<212> TYPE: PRT
<213> ORGANISM: Artificial Sequence
<220> FEATURE:
<223> OTHER INFORMATION: Humanized antibody

<400> SEQUENCE: 54

Gln Val Gln Leu Leu Glu Ser Gly Ala Glu Leu Val Arg Pro Gly Ser
 1               5                  10                  15

Ser Val Lys Ile Ser Cys Lys Ala Ser Gly Tyr Ala Ile Lys Asp Asn
                20                  25                  30

Tyr Met His Trp Val Lys Gln Arg Pro Gly Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Gly Gln Ala Thr Leu Thr Ala Asp Thr Ser Ser Ser Thr Ala Tyr
65                  70                  75                  80

Met Gln Leu Ser Gly Leu Thr Ser Glu Asp Ser Ala Val Tyr Tyr Cys
                85                  90                  95

Asn Thr Trp Ala Tyr Tyr Gly Thr Ser Tyr Gly Gly Phe Ala Tyr Trp
            100                 105                 110

Gly Gln Gly Thr Thr Val Thr
        115

<210> SEQ ID NO 55
<211> LENGTH: 112
<212> TYPE: PRT
<213> ORGANISM: Artificial Sequence
<220> FEATURE:
<223> OTHER INFORMATION: Humanized antibody

<400> SEQUENCE: 55

Asp Ile Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gln Gly Thr Lys Leu Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: Humanized antibody

<400> SEQUENCE: 56

Asp Ile Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gln Gly Thr Lys Leu Glu Ile Lys
            100                 105                 110

<210> SEQ ID NO 57
<211> LENGTH: 82
<212> TYPE: DNA
<213> ORGANISM: Artificial Sequence
<220> FEATURE:
<223> OTHER INFORMATION: synthetic oligonucleotide for mutagenesis
      of hu11k2

<400> SEQUENCE: 57
cccgcggaga cattcagatg actcagtctc catcctccct gtcagcatct gtgggagaca      60
gagtcaccat tacttgcaag gc                                              82

<210> SEQ ID NO 58
<211> LENGTH: 53
<212> TYPE: DNA
<213> ORGANISM: Artificial Sequence
<220> FEATURE:
<223> OTHER INFORMATION: synthetic oligonucleotide for mutagenesis
      of hu11k2

<400> SEQUENCE: 58
ggtatcagca gaaaccagga aaggcccta agctcttaat ttctggtgca acc     53

<210> SEQ ID NO 59
<211> LENGTH: 69
<212> TYPE: DNA
<213> ORGANISM: Artificial Sequence
<220> FEATURE:
<223> OTHER INFORMATION: synthetic oligonucleotide for mutagenesis
      of hu11k2

<400> SEQUENCE: 59
ggaaaagatt acactctcac cattagcagt ctacagcctg aggatttttgc tacttattac     60 tgtcaacag     69

<210> SEQ ID NO 60
<211> LENGTH: 49
<212> TYPE: DNA
<213> ORGANISM: Artificial Sequence
<220> FEATURE:
<223> OTHER INFORMATION: synthetic oligonucleotide for mutagenesis
      of hu11k2

<400> SEQUENCE: 60
cgttcggagg ggggaccaag gtggagatct aaaaaaggg cgaattctg     49

<210> SEQ ID NO 61
<211> LENGTH: 47
<212> TYPE: DNA
<213> ORGANISM: Artificial Sequence
<220> FEATURE:
<223> OTHER INFORMATION: synthetic oligonucleotide for mutagenesis
      of hu11k2

<400> SEQUENCE: 61
gattcagtgg cagtggatcc ggaacagatt acactctcac cattagc     47

<210> SEQ ID NO 62
<211> LENGTH: 55
<212> TYPE: DNA
<213> ORGANISM: Artificial Sequence
<220> FEATURE:
<223> OTHER INFORMATION: synthetic oligonucleotide for mutagenesis
      of hu11k2

<400> SEQUENCE: 62
gtggttacag gggtcaactc acaggttcag ctggtgcagt ctggggcaga gcttg     55

<210> SEQ ID NO 63
<211> LENGTH: 79
<212> TYPE: DNA
<213> ORGANISM: Artificial Sequence
<220> FEATURE:
<223> OTHER INFORMATION: synthetic oligonucleotide for mutagenesis
      of hu11k2

<400> SEQUENCE: 63
gcagtctggg gcagaggtga agaagcccgg gtcctcagtc aaggtctcct gcaaggcttc     60
tggcctcaac attaaagac     79

<210> SEQ ID NO 64
<211> LENGTH: 56
<212> TYPE: DNA
<213> ORGANISM: Artificial Sequence
<220> FEATURE:
<223> OTHER INFORMATION: synthetic oligonucleotide for mutagenesis of hu11k2

<210> SEQ ID NO 65
<211> LENGTH: 95
<212> TYPE: DNA
<213> ORGANISM: Artificial Sequence
<220> FEATURE:
<223> OTHER INFORMATION: synthetic oligonucleotide for mutagenesis
of hu11k2

<400> SEQUENCE: 65
cccgaagttc agggcagag ccactataac agcagacaca tccacgagca cagcctacat      60
ggagctcagc agcctgagat ctgaggacac tgccg                                95

<210> SEQ ID NO 66
<211> LENGTH: 58
<212> TYPE: DNA
<213> ORGANISM: Artificial Sequence
<220> FEATURE:
<223> OTHER INFORMATION: synthetic oligonucleotide for mutagenesis
of hu11k2

<400> SEQUENCE: 66
ggggccaagg gaccactgtg acagtctcct caggtgagtc ctaagcttgg tacccggg       58

<210> SEQ ID NO 67
<211> LENGTH: 53
<212> TYPE: DNA
<213> ORGANISM: Artificial Sequence
<220> FEATURE:
<223> OTHER INFORMATION: synthetic oligonucleotide for mutagenesis
of hu11k2

<400> SEQUENCE: 67
ggtctcctgc aaggcttcag gcctcaccat tagcgacacc tatatgcact ggg            53

<210> SEQ ID NO 68
<211> LENGTH: 46
<212> TYPE: DNA
<213> ORGANISM: Artificial Sequence
<220> FEATURE:
<223> OTHER INFORMATION: synthetic oligonucleotide for mutagenesis
of hu11k2

<400> SEQUENCE: 68
ggcgcctgga cagggcctcg agtggatggg aaggattgat cctgcg                    46

<210> SEQ ID NO 69
<211> LENGTH: 57
<212> TYPE: DNA
<213> ORGANISM: Artificial Sequence
<220> FEATURE:
<223> OTHER INFORMATION: Synthetic oligonucleotide for mutagenesis
of hu11k2

<400> SEQUENCE: 69
gacccgaagt tccagggcag agtcactata actgcagaca catccacgag cacagcc        57